US012774277B2

(12) United States Patent
Fiorelli et al.

(10) Patent No.: US 12,774,277 B2
(45) Date of Patent: Oct. 27, 2026

(54) AMINO QUINAZOLINE DERIVATIVES AS P2X3 INHIBITORS

(71) Applicant: CHIESI FARMACEUTICI S.P.A., Parma (IT)

(72) Inventors: Claudio Fiorelli, Parma (IT); Paolo Bruno, Parma (IT); Matteo Biagetti, Parma (IT); Daniela Pizzirani, Parma (IT); Daniele Pala, Parma (IT); Paolo Ronchi, Parma (IT); Sara Guariento, Parma (IT); Charles Baker-Glenn, Parma (IT); Hervé Van De Poël, Parma (IT); Kim Louise Hirst, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 671 days.

(21) Appl. No.: 18/038,744

(22) PCT Filed: Nov. 26, 2021

(86) PCT No.: PCT/EP2021/083141

§ 371 (c)(1),
(2) Date: May 25, 2023

(87) PCT Pub. No.: WO2022/112490

PCT Pub. Date: Jun. 2, 2022

(65) Prior Publication Data

US 2024/0025880 A1 Jan. 25, 2024

(30) Foreign Application Priority Data

Nov. 27, 2020 (EP) .................................... 20210189

(51) Int. Cl.

| | |
|---|---|
| ***C07D 403/12*** | (2006.01) |
| ***C07D 401/14*** | (2006.01) |
| ***C07D 403/14*** | (2006.01) |
| ***C07D 405/14*** | (2006.01) |
| ***C07D 413/12*** | (2006.01) |
| ***C07D 413/14*** | (2006.01) |
| ***C07D 417/12*** | (2006.01) |
| ***C07D 419/00*** | (2006.01) |

(52) U.S. Cl.
CPC ......... *C07D 403/12* (2013.01); *C07D 401/14* (2013.01); *C07D 403/14* (2013.01); *C07D 405/14* (2013.01); *C07D 413/12* (2013.01); *C07D 413/14* (2013.01); *C07D 417/12* (2013.01); *C07D 419/00* (2013.01)

(58) Field of Classification Search
CPC .. C07D 401/14; C07D 403/12; C07D 403/14; C07D 405/14; C07D 413/12; C07D 413/14; C07D 417/12; C07D 419/00
See application file for complete search history.

(56) References Cited

U.S. PATENT DOCUMENTS

2011/0009432 A1 1/2011 Wei et al.

FOREIGN PATENT DOCUMENTS

WO WO-2020239951 A1 12/2020
WO WO-2020239952 A1 12/2020

OTHER PUBLICATIONS

Rosenthal (Bioorganic & Medicinal Chemistry Letters 21 (2011) 3152-3158). (Year: 2011).*
Gabor Szanto et al., "New P2X3 receptor antagonists. Part 2: Identification and SAR of quinazolinones", Bioorganic & Medicinal Chemistry Letters, 26, 2016, pp. 3905-3912.
International Search Report and Written Opinion issued Feb. 1, 2022 in PCT/EP2021/083141, 11 pages.

* cited by examiner

*Primary Examiner* — Kortney L. Klinkel
*Assistant Examiner* — Richard Grant Peckham
(74) *Attorney, Agent, or Firm* — Element IP, PLC

(57) ABSTRACT

The present invention relates to compounds of formula I inhibiting P2X purinoceptor 3; particularly the invention relates to compounds that are amino quinazoline derivatives, methods of preparing such compounds, pharmaceutical compositions containing them and therapeutic use thereof. The compounds of the invention may be useful in the treatment of many disorders associated with $P2X_3$ receptors mechanisms, such as respiratory diseases including cough, asthma, idiopathic pulmonary fibrosis (IPF) and chronic obstructive pulmonary disease (COPD).

9 Claims, No Drawings

AMINO QUINAZOLINE DERIVATIVES AS P2X3 INHIBITORS

FIELD OF THE INVENTION

The present invention relates to compounds inhibiting P2X purinoceptor 3 (hereinafter $P2X_3$ inhibitors); particularly the invention relates to compounds that are amino quinazoline derivatives, methods of preparing such compounds, pharmaceutical compositions containing them and therapeutic use thereof.

The compounds of the invention may be useful in the treatment of many disorders associated with $P2X_3$ receptors mechanisms, such as respiratory diseases including cough, asthma, idiopathic pulmonary fibrosis (IPF) and chronic obstructive pulmonary disease (COPD).

BACKGROUND OF THE INVENTION

P2X receptors are cell surface ion channels activated by extracellular Adenosine 5-TriPhosphate (ATP). P2X receptor family are trimeric assemblies composed of seven distinct subunit subtypes (P2X1-7) that assemble as homomeric and heteromeric channels. All subunits share a common topology containing intracellular termini, two transmembrane helices forming the ion channels and a large extracellular domain containing the ATP binding site. Homomeric $P2X_1$, $P2X_2$, $P2X_3$, $P2X_4$, $P2X_5$, and $P2X_7$ channels and heteromeric $P2X_{2/3}$ and $P2X_{1/5}$ channels have been fully characterized following heterologous expression. P2X receptors are abundantly distributed, and functional responses are seen in neurons, glia, epithelia, endothelia, bone, muscle, and hemopoietic tissues. On smooth muscles, P2X receptors respond to ATP released from sympathetic motor nerves (e.g., in ejaculation). On sensory nerves, they are involved in the initiation of afferent signals in several viscera (e.g., bladder, intestine) and play a key role in sensing tissue-damaging and inflammatory stimuli. Paracrine roles for ATP signaling through P2X receptors are likely in neurohypophysis, ducted glands, airway epithelia, kidney, bone and hemopoietic tissues. (R A. North: Molecular Physiology of P2X Receptors; Physiol Rev, Vol 82, October 2002). All P2X receptors are non-selective cation channels permeable to Na+ and Ca+ ions and are activated by ATP; however, the pharmacology of the receptor subtypes varies with respect to sensitivity to ATP and to small molecules antagonists. (K Kaczmarek-Hajek et al: Molecular and functional properties of P2X receptors—recent progress and persisting challenges; Purinergic Signalling 8:375-417, 2012)

In humans, the $P2X_3$ receptor has been reported in heart and spinal cord at the mRNA level and in DRG, intestine (myenteric plexus neurons), urinary bladder (urothelium and suburothelium), and dental pulp at the protein level (Garcia-Guzman M et al: Molecular characterization and pharmacological properties of the human $P2X_3$ purinoceptor: Brain Res Mol Brain Res. 1997; 47(1-2):59-66).

The neurophysiological role of $P2X_3$ receptors in sensory nerve function in the airways is similar to that mediating somatic nociception (Undem B J and Nassenstein C: Airway nerves and dyspnea associated with inflammatory airway disease, Respir Physiol Nerobiol 167: 36-44, 2009). This similarity has driven hypotheses concerning the involvement of $P2X_3$ receptors in the symptoms of airway dysfunction including cough and bronchial hyper-reactivity (Ford A P: In pursuit of $P2X_3$ antagonists: novel therapeutics for chronic pain and afferent sensitization, Purinergic signal 8

(suppl 1):3-26, 2012; North R A, Jarvis M F P2X Receptors as Drug Targets; Mol Pharmacol, 83:759-769, 2013). $P2X_3$ subunits are also co-localized in many neurons, particularly within DRG, nodose ganglia, nucleus tractus solitarius, and taste buds (Cheung K K, Burnstock G: Localization of $P2X_3$ receptors and coexpression with P2X2 receptors during rat embryonic neurogenesis. J Comp Neurol 443(4):368-382 2002)

$P2X_3$ antagonists have been proposed for the treatment of diabetic neuropathic pain (Guo J et al: Contributions of purinergic $P2X_3$ receptors within the midbrain periaqueductal gray to diabetes-induced neuropathic pain, J Physiol Sci January; 65(1):99-104 2015).

$P2X_3$ and $P2X_{2/3}$ channels play an important role in the development of articular hyperalgesia of arthritic joints (Teixeira J M et al: $P2X_3$ and $P2X_{2/3}$ Receptors Play a Crucial Role in Articular Hyperalgesia Development Through Inflammatory Mechanisms in the Knee Joint Experimental Synovitis, Mol Neurobiol October; 54(8): 6174-6186, 2017).

$P2X_3$ are also a potential target for therapeutic treatment of bladder pain. They were also proposed to be analgesic targets to treat ureteral colicky pain and to facilitate ureteral stone passage (Canda A E et al: Physiology and pharmacology of the human ureter: basis for current and future treatments, Urol Int. 78(4):289-98, 2007).

$P2X_3$ over-expression is involved in poor recurrence-free survival in hepatocellular carcinoma patients and identifies the $P2X_3$ as a potential therapeutic target (Maynard J P et al: $P2X_3$ purinergic receptor overexpression is associated with poor recurrence-free survival in hepatocellular carcinoma patients Oncotarget December 1; 6(38):41162-79, 2015).

It has been suggested that $P2X_3$ antagonists may improve recovery of erectile function (Li C L et al: Effects of intracavernous injection of $P2X_3$ and NK1 receptor antagonists on erectile dysfunction induced by spinal cord transection in rats, Andrologia. February; 47(1):25-9, 2015).

ATP enhances citric acid-evoked and histamine-evoked cough in preclinical models, effects that can be attenuated by $P2X_3$ selective antagonists (Kamei J and Takahashi Y: Involvement of ionotropic purinergic receptors in the histamine-induced enhancement of the cough reflex sensitivity in guinea pigs, October 10; 547(1-3):160-4, 2006). In humans, local delivery of ATP initiates cough and bronchospasm (Basoglu O K et al: Effects of aerosolized adenosine 5'-triphosphate vs adenosine 5'-monophosphate on dyspnea and airway caliber in healthy nonsmokers and patients with asthma, Chest. October; 128(4):1905-9, 2005).

The therapeutic promise of $P2X_3$ antagonists for the treatment of chronic cough was first recognized by Ford and Undem (Ford A P, Undem B J: The therapeutic promise of ATP antagonism at $P2X_3$ receptors in respiratory and urological disorders, Front Cell Neurosci, December 19; 7:267, 2013). $P2X_3$ are expressed by airway afferent nerves and mediate hypersensitivity of the cough reflex, which is dramatically reduced by the oral $P2X_3$ antagonist, AF-219 (Abdulqawi et al: $P2X_3$ receptor antagonist (AF-219) in refractory chronic cough: a randomised, double-blind, placebo-controlled phase 2 study, Lancet 385, 1198-205, 2015).

ATP is a key neurotransmitter in the taste system, acting largely via $P2X_{2/3}$ heteromultimer receptors. Consequently, disruption of taste function may be an unintentional consequence of therapeutic trials of pain, chronic cough and other conditions using purinergic $P2X_3$ antagonists (Vandenbeuch A et al: Role of the ectonucleotidase NTPDase2 in taste bud function, Proc Natl Acad Sci USA, September 3; 110(36): 14789-94, 2013. Bo X et al: Localization of ATP-gated P2X2 and $P2X_3$ receptor immunoreactive nerves in rat taste buds, Neuroreport, 10(5):1107-11, 1999). Various compounds have been described in the literature as $P2X_3$ and/or $P2X_{2/3}$ Inhibitors.

WO2017058645 (Afferent Pharmaceuticals INC) discloses the use of diaminopyrimidine $P2X_3$/$P2X_{2/3}$ antagonists for the treatment of disorders including cough, chronic cough and urge to cough, including cough associated with a respiratory disease or disorder, administering an efficacious amount of the compound disclosed. However, amino quinazoline derivatives are not disclosed.

WO2017011729 (Patara Pharma LLC), discloses the use of cromolyn or a pharmaceutically acceptable salt thereof and $P2X_3$ and/or a $P2X_{2/3}$ receptor antagonist as antitussive agent, for the treatment of lung diseases and conditions.

WO2016091776, (Evotec AG), discloses 1,3-thiazol-2-yl substituted benzamide compounds that inhibit $P2X_3$ receptor and to pharmaceutical compositions containing such compounds, and the use of compounds for the treatment of several disorders, including the respiratory diseases.

WO2016088838 (Shionogi), discloses purine derivatives compounds having a novel $P2X_3$ and/or $P2X_{2/3}$ receptor antagonizing effect.

WO2016084922, (Shionogi), discloses triazine derivatives compounds having a novel $P2X_3$ and/or $P2X_{2/3}$ receptor antagonizing effect WO2008123963 (Renovis) relates to fused heterocyclic compounds of the class tetrahydropyrido [4,3-d]pyrimidines and pharmaceutical compositions comprising such compounds. Also provided are methods for preventing and/or treating several disorders, such as neurodegenerative disorders, pain, asthma, autoimmune disorders administering the disclosed compounds.

WO2008130481 (Renovis) discloses 2-cyanophenyl fused heterocyclic compounds of the class tetrahydropyrido [4,3-d]pyrimidines and pharmaceutical compositions comprising such compounds.

WO2010033168 (Renovis) discloses a series of benzamides substituted with phenyl or pyridyl which are stated to be useful for treatment of diseases associated with P2X purinergic receptors, and more particularly to $P2X_3$ receptor and/or $P2X_{2/3}$ receptor antagonists. However, amino quinazoline derivatives are not disclosed.

WO2009110985 (Renovis) relates to phenyl- and pyridyl-substituted benzamide compounds and pharmaceutical compositions comprising such compounds, but not thiazole-substituted benzamides, rendering said compounds different from the compounds of the present invention.

WO2008000645 (Roche) discloses tetrazole substituted arylamides compounds antagonists of $P2X_3$ and/or $P2X_{2/3}$ receptors, useful for the treatment of genitourinary, pain, gastrointestinal and respiratory diseases, conditions and disorders.

Despite the above cited prior art, there is still the need of novel amino quinazoline compounds for treatment of diseases associated with $P2X_3$ receptors in many therapeutic areas such as in particular the respiratory diseases, preferably having a selective action on the $P2X_3$ receptor.

Of note, the state of the art does not describe or suggest amino quinazoline derivatives compounds of general formula (I) of the present invention which represent a solution to the aforementioned need.

SUMMARY OF THE INVENTION

The present invention refers to compounds of formula (I)

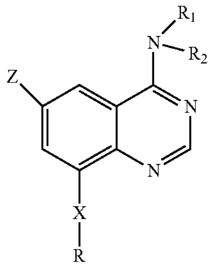

wherein

X is selected from S, $SO_2$, SO, or O;

Z is selected from the group consisting of heteroaryl and aryl, wherein any of such heteroaryl and aryl may be optionally substituted by one or more groups selected from $(C_1-C_3)$alkyl-, halo and $(C_1-C_6)$haloalkyl-;

$R_1$ is H or $(C_1-C_4)$alkyl;

$R_2$ is heteroaryl$(C_1-C_4)$alkyl-, wherein any of such alkyl and heteroaryl may be optionally substituted by one or more groups selected from $(C_1-C_3)$alkyl, $(C_1-C_6)$haloalkyl and halo;

R is selected from the group consisting of $(C_1-C_6)$alkyl-, $(C_1-C_6)$alkyl-CN, $(C_1-C_6)$haloalkyl, —$NR_AR_B$, $(C_3-C_8)$heterocycloalkyl-$(C_1-C_6)$alkyl-, $(C_3-C_8)$heterocycloalkyl-, $(C_3-C_8)$heteroaryl-$(C_1-C_6)$alkyl-, $(C_3-C_8)$cycloalkyl-$(C_1-C_6)$alkyl-, $(C_3-C_8)$cycloalkyl-, $R_A$O—$(C_1-C_6)$alkyl-O—$(C_1-C_6)$alkyl-, $R_A$NH—C(O)—$(C_1-C_4)$alkyl-, $R_AR_B$N—C(O)—$(C_1-C_4)$alkyl-, $R_A$O—C(O)$(C_1-C_6)$alkyl-, wherein any of such heterocycloalkyl is unsubstituted or substituted by one or more groups selected from OH, —C(O)$R_A$, —C(O)O$R_A$, $(C_1-C_6)$haloalkyl, —NH—C(O)$R_1$, and oxo; any of such cycloalkyl is substituted by one or more groups selected from —C(O)O$R_A$ and $(C_1-C_6)$haloalkyl-, any of such heteraryl may be optionally substituted by one or more groups selected from $(C_1-C_6)$alkyl-, —OH and $(C_3-C_6)$cycloalkyl-;

$R_A$ and $R_B$ are at each occurrence independently H or selected from the group consisting of $(C_1-C_6)$alkyl-, $(C_1-C_6)$haloalkyl-, —O$R_1$, —$SO_2R_C$ and $(C_3-C_6)$cycloalkyl wherein such cycloalkyl may be optionally substituted by one or more —C(O)O$R_1$, or alternatively $R_A$ and $R_B$ may form together with the nitrogen atom to which they are attached a 5 or 6 membered saturated heterocyclic monocyclic ring system optionally containing a further heteroatom which is nitrogen or oxygen, which may be optionally substituted by one or more groups selected from halo, —O$R_1$;

$R_C$ is aryl;

with the proviso that R is $(C_1-C_6)$alkyl- or unsubstituted $(C_3-C_8)$heterocycloalkyl- only when X is S or SO.

In a second aspect, the invention refers to a pharmaceutical composition comprising a compound of formula (I) or pharmaceutically acceptable salt thereof, either alone or in combination with another one or more active ingredient, in admixture with one or more pharmaceutically acceptable carrier or excipient.

In a third aspect, the invention provides a compound of formula (I) for the use as a medicament.

In a further aspect, the invention provides the use of a compound of formula (I) for use in treatment of any disease wherein the $P2X_3$ receptors are involved.

In a further aspect, the invention refers to a compound of formula (I) for use in the prevention and/or treatment of respiratory diseases including cough, sub-acute or chronic cough, treatment-resistant cough, idiopathic chronic cough, post-viral cough, iatrogenic cough, asthma, idiopathic pulmonary fibrosis (IPF), chronic obstructive pulmonary disease (COPD) and cough associated with respiratory diseases such as COPD, asthma and bronchospasm.

DETAILED DESCRIPTION OF THE INVENTION

Unless otherwise provided, the term compound of formula (I) comprises in its meaning stereoisomer, tautomer or pharmaceutically acceptable salt or solvate.

The term "pharmaceutically acceptable salts", as used herein, refers to derivatives of compounds of formula (I) wherein the parent compound is suitably modified by converting any of the free acid or basic group, if present, into the corresponding addition salt with any base or acid conventionally intended as being pharmaceutically acceptable.

Suitable examples of said salts may thus include mineral or organic acid addition salts of basic residues such as amino groups, as well as mineral or organic basic addition salts of acid residues such as carboxylic groups.

The term "halogen" or "halogen atoms" as used herein includes fluorine, chlorine, bromine, and iodine atom, preferably chlorine or fluorine.

The term "($C_x$-$C_y$) alkyl" wherein x and y are integers, refers to a straight or branched chain alkyl radical having from x to y carbon atoms. Thus, when x is 1 and y is 6, for example, the term includes methyl, ethyl, n-propyl, isopropyl, n-butyl, isobutyl, sec-butyl, t-butyl, n-pentyl and n-hexyl.

As used herein, the term "($C_x$-$C_y$)alkylene" wherein x and y are integers, refers to a $C_x$-$C_y$alkyl radical having in total two unsatisfied valencies, such as a divalent methylene radical.

The expressions "($C_x$-$C_y$) haloalkyl" wherein x and y are integers, refer to the above defined "$C_x$-$C_y$alkyl" groups wherein one or more hydrogen atoms are replaced by one or more halogen atoms, which can be the same or different.

Examples of said "($C_x$-$C_y$) haloalkyl" groups may thus include halogenated, poly-halogenated and fully halogenated alkyl groups wherein all of the hydrogen atoms are replaced by halogen atoms, e.g. trifluoromethyl or difluoro methyl, trifluoroethyl groups.

By way of analogy, the terms "($C_1$-$C_6$) hydroxyalkyl" or "($C_1$-$C_6$) aminoalkyl" refer to the above defined "($C_1$-$C_6$) alkyl" groups wherein one or more hydrogen atoms are replaced by one or more hydroxy (OH) or amino group respectively. Examples include respectively hydroxymethyl, aminomethyl, dimethylaminopropyl and the like.

In the present description, unless otherwise provided, the aminoalkyl encompasses alkyl groups (i.e. "($C_1$-$C_6$) alkyl" groups) substituted by one or more amino group ($-NR^AR^B$). Thus, an example of aminoalkyl is a monoaminoalkyl group such as $R^AR^BN$—($C_1$-$C_6$) alkyl.

The term "($C_x$-$C_y$) cycloalkyl" wherein x and y are integers, refers to saturated cyclic hydrocarbon groups containing the indicated number of ring carbon atoms. Examples include cyclopropyl, cyclobutyl, cyclopentyl, cyclohexyl, cycloheptyl.

The term "aryl" refers to mono cyclic carbon ring systems which have 6 ring atoms wherein the ring is aromatic. Examples of suitable aryl monocyclic ring systems include, for instance, phenyl.

The term "heteroaryl" refers to a mono- or bi-cyclic aromatic radical containing one or more heteroatoms selected from S, N and O, and includes radicals having two such monocyclic rings, or one such monocyclic ring and one monocyclic aryl ring, which are fused through a common bond. Examples of suitable 5,6-membered heteroaryl are: are thienyl, furyl, pyrrolyl, imidazolyl, thiazolyl, isothiazolyl, pyrazolyl, oxazolyl, isoxazolyl, isothiazolyl, triazolyl, thiadiazolyl, oxadiazolyl, pyridinyl, pyridazinyl, pyrimidinyl, pyrazinyl, tetrazolyl and triazinyl.

The term "heterocyclyl" or "heterocyclic" relate to a saturated mono-, bi- or tri-cyclic non-aromatic radical containing one or more heteroatoms selected from S, N and O. In the case of bicyclic heterocyclic systems, included within the scope of the term are fused, spiro and bridged bicyclic systems.

The term "($C_x$-$C_y$) heterocycloalkyl" wherein x and y are integers, refers to saturated or partially unsaturated monocyclic ($C_x$-$C_y$) cycloalkyl groups in which at least one ring carbon atom is replaced by at least one heteroatom (e.g. N, S or O) or may bear an -oxo (=O) substituent group. Said heterocycloalkyl (i.e. heterocyclic radical or group) may be further optionally substituted on the available positions in the ring, namely on a carbon atom, or on an heteroatom available for substitution. Substitution on a carbon atom includes spiro disubstitution as well as substitution on two adjacent carbon atoms, in both cases thus form additional condensed 5 to 6 membered heterocyclic ring. Examples of ($C_x$-$C_y$) heterocycloalkyl are represented by: pyrrolidinyl, imidazolidinyl, thiazolidinyl, piperazinyl, piperidinyl, morpholinyl, thiomorpholinyl, dihydro- or tetrahydro-pyridinyl, tetrahydrothiophenyl, azetidinyl, oxetanyl, tetrahydropyranyl, pyranyl, 2H- or 4H-pyranyl, dihydro- or tetrahydrofuranyl, dihydroisoxazolyl, pyrrolidin-2-one-yl, dihydropyrrolyl radicals and the like.

Specific examples of said heterocycle radicals are tetrahydrothiophene 1,1-dioxide, 3,3-difluoropyrrolidinyl, 1-pyrrolidinyl, 1-methyl-2-pyrrolidinyl, 1-piperidinyl, 1-piperazinyl, 4-morpholinyl.

The expressions "Aryloxyl" and "Aryl ($C_1$-$C_6$) alkoxyl" likewise "heteroAryloxyl" and "Heteroaryl ($C_1$-$C_6$) alkoxyl" refer to Aryl or Heteroaryl groups attached through an oxygen bridge and chained Aryl-alkoxyl or HeteroAryl-alkoxyl groups. Examples of such groups are phenyloxy, benzyloxy and pyridinyloxy respectively.

The term "aryl ($C_1$-$C_6$) alkyl" refers to an aryl ring linked to a straight-chained or branched alkyl groups wherein the number of carbon atoms is from 1 to 6, e.g. phenylmethyl (i.e. benzyl), phenylethyl or phenylpropyl.

The term ($C_z$-$C_k$)heterocycloalkyl-($C_x$-$C_y$)alkyl wherein z and k are integers, refers to an heterocyclic ring linked to a straight-chained or branched alkyl groups having from x to y carbon atoms.

Likewise, the term "heteroaryl ($C_x$-$C_y$)alkyl" or "aryl ($C_x$-$C_y$)alkyl" refers to an heteroaryl or aryl ring linked to a straight-chained or branched alkyl groups having from x to y carbon atoms.

The expression "ring system" refers to mono- or bicyclic or polycyclic ring systems which may be saturated, partially unsaturated or unsaturated, such as aryl, ($C_3$-$C_{10}$) cycloalkyl, ($C_3$-$C_6$)heterocycloalkyl or heteroaryl.

The terms "group", "radical" or "fragment" or "substituent" are synonymous and are intended to indicate functional groups or fragments of molecules attachable to a bond or other fragments or molecules. Thus, as an example, a "heterocyclic radical" herein refers to a mono- or bi-cyclic saturated or partially saturated heterocyclic moiety (group, radical), preferably a 4 to 11 membered monocyclic radical, at least one further ring carbon atom in the said heterocyclic radical is optionally replaced by at least one further heteroatom independently selected from N, S or O and/or may bear an -oxo (=O) substituent group, said heterocyclic radical is further optionally including spiro disubstitution as well as substitution on two adjacent or vicinal atoms forming an additional 5 to 6 membered cyclic or heterocyclic, saturated, partially saturated or aromatic ring. Examples of said heterocycle radicals are 1-pyrrolidinyl, 1-piperidinyl, 1-piperazinyl, 4-morpholinyl and the like.

A dash ("-") that is not between two letters or symbols is meant to represent the point of attachment for a substituent. When graphically represented the point of attachment in a cyclic functional group is indicated with a dot ("•") localized in one of the available ring atom where the functional group is attachable to a bond or other fragment of molecules.

An oxo moiety is represented by (O) as an alternative to the other common representation, e.g. (=O). Thus, in terms of general formula, the carbonyl group is herein represented as —C(O)—, in general, the bracketed group is a lateral group, not included into the chain, and brackets are used, when deemed useful, to help disambiguating linear chemical formulas; e.g. the sulfonyl group $—SO_2—$ might be also represented as $—S(O)_2—$ to disambiguate e.g. with respect to the sulfinic group —S(O)O—.

Whenever basic amino or quaternary ammonium groups are present in the compounds of formula I, physiologically acceptable anions may be present, selected among chloride, bromide, iodide, trifluoroacetate, formate, sulfate, phosphate, methanesulfonate, nitrate, maleate, acetate, citrate, fumarate, tartrate, oxalate, succinate, benzoate, p-toluenesulfonate, pamoate and naphthalene disulfonate. Likewise, in the presence of acidic groups such as COOH groups, corresponding physiological cation salts may be present as well, for instance including alkaline or alkaline earth metal ions.

It will be apparent that compounds of formula (I) when contain one or more stereogenic center, may exist as optical stereoisomers.

Where the compounds according to the invention have at least one stereogenic center, they may accordingly exist as enantiomers. Where the compounds according to the invention possess two or more stereogenic centers, they may additionally exist as diastereoisomers. All such single enantiomers, diastereoisomers and mixtures thereof in any proportion are encompassed within the scope of the present invention. The absolute configuration (R) or (S) for carbon bearing a stereogenic center is assigned on the basis of Cahn-Ingold-Prelog nomenclature rules based on groups' priorities.

The invention further concerns the corresponding deuterated derivatives of compounds of formula (I).

All preferred groups or embodiments described above and herebelow for compounds of formula I may be combined among each other and apply as well mutatis mutandis.

As above indicated, the present invention refers to a series of compounds represented by the general formula (I) as herein below described in details, which are endowed with an antagonist property versus receptor $P2X_3$.

Differently from similar compounds of the prior art, the compounds of formula (I) of the present invention are able to act as antagonist $P2X_3$ in a substantive and effective way, particularly appreciated by the skilled person when looking at a suitable and efficacious compounds useful for the treatment of respiratory disease, in particular chronic cough.

As indicated in the experimental part, the compounds of formula (I) have an activity as shown in Table 2, wherein for each compound is reported the potency expressed as half maximal inhibitory concentration ($pIC_{50}$) on receptors.

As further advantage, the compound of formula (I) have surprisingly been found to effectively and selectively inhibit mainly the $P2X_3$ receptor and said compounds are useful for the treatment of respiratory disease avoiding adverse effect, such as loss of taste response. In fact, as it can be appreciated in Table 3, the compounds of formula (I) show a greater activity versus the receptor $P2X_3$ in comparison to the receptor $P2X_{2/3}$.

Thus, in one aspect the present invention relates to a compound of general formula (I) as $P2X_3$ antagonist

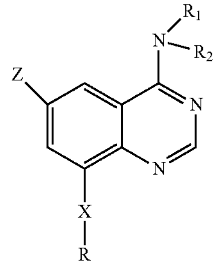

wherein

X is selected from S, $SO_2$, SO, or O;

Z is selected from the group consisting of heteroaryl and aryl, wherein any of such heteroaryl and aryl may be optionally substituted by one or more groups selected from $(C_1-C_3)$alkyl-, halo and $(C_1-C_6)$haloalkyl-;

$R_1$ is H or $(C_1-C_4)$alkyl;

$R_2$ is heteroaryl$(C_1-C_4)$alkyl-, wherein any of such alkyl and heteroaryl may be optionally substituted by one or more groups selected from $(C_1-C_3)$alkyl, $(C_1-C_6)$haloalkyl and halo;

R is selected from the group consisting of $(C_1-C_6)$alkyl-, $(C_1-C_6)$alkyl-CN, $(C_1-C_6)$haloalkyl, $—NR_AR_B$, $(C_3-C_8)$heterocycloalkyl-$(C_1-C_6)$alkyl-, $(C_3-C_8)$heterocycloalkyl-, $(C_3-C_8)$heteroaryl-$(C_1-C_6)$alkyl-, $(C_3-C_8)$cycloalkyl-$(C_1-C_6)$alkyl-, $(C_3-C_8)$cycloalkyl-, $R_AO—(C_1-C_6)$alkyl-O—$(C_1-C_6)$alkyl-, $R_ANH—C(O)—(C_1-C_4)$alkyl-, $R_AR_BN—C(O)—(C_1-C_4)$alkyl-, $R_AO—C(O)(C_1-C_6)$alkyl-, wherein any of such heterocycloalkyl is unsubstituted or substituted by one or more groups selected from OH, $—C(O)R_A$, $—C(O)OR_A$, $(C_1-C_6)$haloalkyl, —NH—C(O)$R_1$, and oxo; any of such cycloalkyl is substituted by one or more groups selected from $—C(O)OR_A$ and $(C_1-C_6)$haloalkyl-, any of such heteraryl may be optionally substituted by one or more groups selected from $(C_1-C_6)$alkyl-, —OH and $(C_3-C_6)$cycloalkyl-;

$R_A$ and $R_B$ are at each occurrence independently H or selected from the group consisting of $(C_1-C_6)$alkyl-, $(C_1-C_6)$haloalkyl-, $—OR_1$, $—SO_2R_C$ and $(C_3-C_6)$cycloalkyl wherein such cycloalkyl may be optionally substituted by one or more $—C(O)OR_1$, or alternatively $R_A$ and $R_B$ may form together with the nitrogen atom to which they are attached a 5 or 6 membered saturated heterocyclic monocyclic ring system optionally containing a further heteroatom which is nitrogen or oxygen, which may be optionally substituted by one or more groups selected from halo, $—OR_1$;

$R_C$ is aryl;

with the proviso that R is $(C_1-C_6)$alkyl- or unsubstituted $(C_3-C_8)$heterocycloalkyl- only when X is S or SO.

In a preferred embodiment Z is selected from the group consisting of heteroaryl and aryl wherein the heteroaryl is selected from pyridine and pyrimidine.

In a further preferred embodiment $R_2$ is heteroaryl$(C_1-C_4)$alkyl- wherein the hereroayl is selected from the group consisting of pyridazine, thiadiazole, pyrimidine and oxadiazole.

In a preferred embodiment, the invention refers to at least one of the compounds listed in the Table 1 below and pharmaceutical acceptable salts thereof.

TABLE 1

| List of preferred compounds of Formula (I) | | |
|---|---|---|
| Ex. N. | Structure | Chemical Name |
| Example 1 | 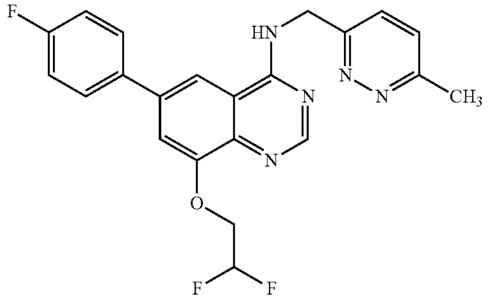 [SMILES: Cc1ccc(CNc2ncnc3c(OCC(F)F)cc(-c4ccc(F)cc4)cc23)nn1] | 8-(2,2-difluoroethoxy)-6-(4-fluorophenyl)-N-((6-methylpyridazin-3-yl)methyl)quinazolin-4-amine |
| Example 2 | 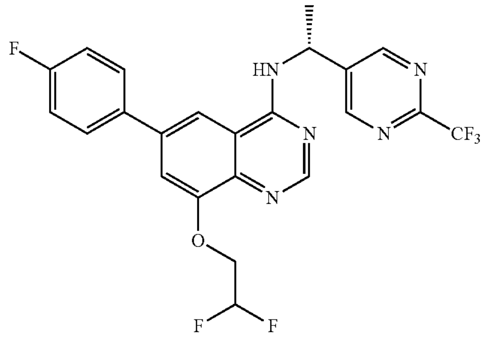 [SMILES: C[C@@H](Nc1ncnc2c(OCC(F)F)cc(-c3ccc(F)cc3)cc12)c1cnc(C(F)(F)F)nc1] | (R)-8-(2,2-difluoroethoxy)-6-(4-fluorophenyl)-N-(1-(2-(trifluoromethyl)pyrimidin-5-yl)ethyl)quinazolin-4-amine |
| Example 4 | 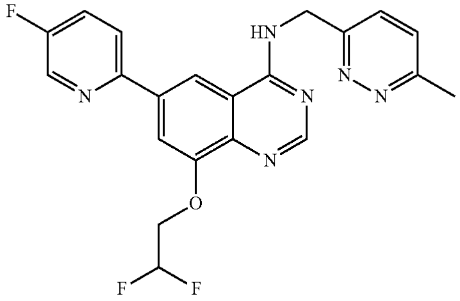 [SMILES: Cc1ccc(CNc2ncnc3c(OCC(F)F)cc(-c4ccc(F)cn4)cc23)nn1] | 8-(2,2-difluoroethoxy)-6-(5-fluoropyridin-2-yl)-N-((6-methylpyridazin-3-yl)methyl)quinazolin-4-amine |
| Example 5 | 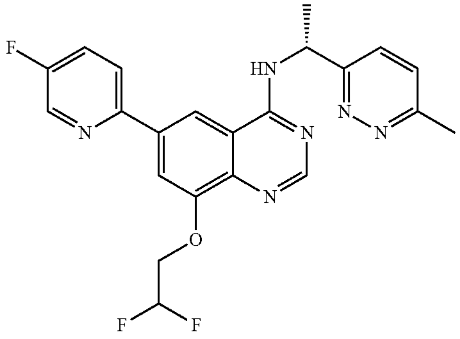 [SMILES: Cc1ccc([C@@H](C)Nc2ncnc3c(OCC(F)F)cc(-c4ccc(F)cn4)cc23)nn1] | (R)-8-(2,2-difluoroethoxy)-6-(5-fluoropyridin-2-yl)-N-(1-(6-methylpyridazin-3-yl)ethyl)quinazolin-4-amine |

TABLE 1-continued

| List of preferred compounds of Formula (I) | | |
|---|---|---|
| Ex. N. | Structure | Chemical Name |
| Example 6 | 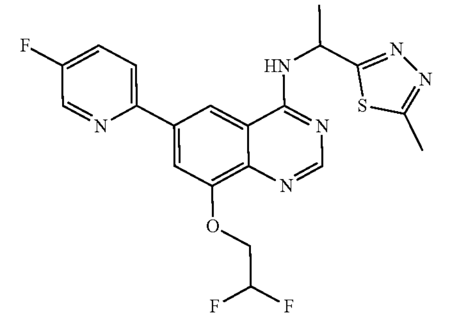 [SMILES: Cc1nnc(C(C)Nc2ncnc3c(OCC(F)F)cc(-c4ccc(F)cn4)cc23)s1] | Single enantiomer 1 of 8-(2,2-difluoroethoxy)-6-(5-fluoro-2-pyridyl)-N-[1-(5-methyl-1,3,4-thiadiazol-2-yl)ethyl]quinazolin-4-amine |
| Example 7 | 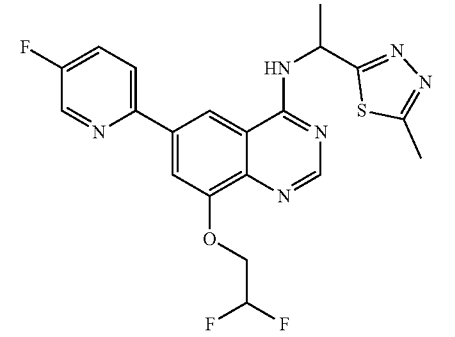 [SMILES: Cc1nnc(C(C)Nc2ncnc3c(OCC(F)F)cc(-c4ccc(F)cn4)cc23)s1] | Single enantiomer 2 of 8-(2,2-difluoroethoxy)-6-(5-fluoro-2-pyridyl)-N-[1-(5-methyl-1,3,4-thiadiazol-2-yl)ethyl]quinazolin-4-amine |
| Example 8 | 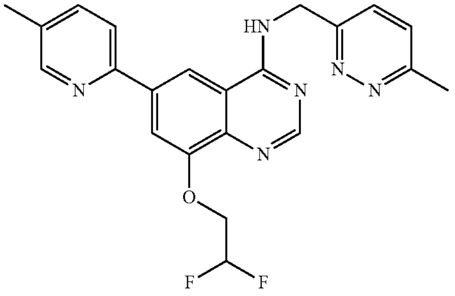 | 8-(2,2-Difluoroethoxy)-N-((6-methylpyridazin-3-yl)methyl)-6-(5-methylpyridin-2-yl)quinazolin-4-amine |
| Example 9 | 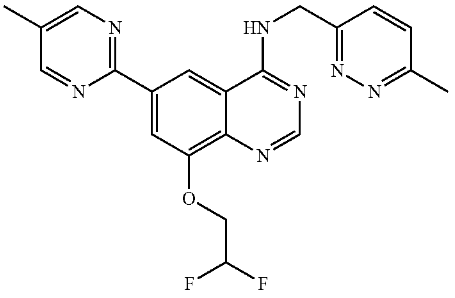 | 8-(2,2-difluoroethoxy)-N-[(6-methylpyridazin-3-yl)methyl]-6-(5-methylpyrimidin-2-yl)quinazolin-4-amine |
| Example 10 | 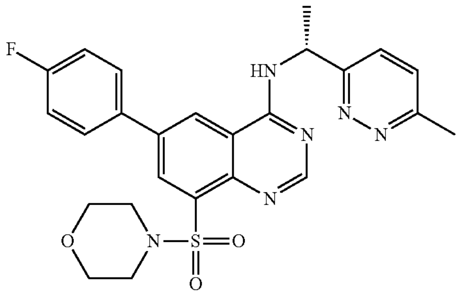 [SMILES: Cc1ccc([C@@H](C)Nc2ncnc3c(S(=O)(=O)N4CCOCC4)cc(-c4ccc(F)cc4)cc23)nn1] | (R)-6-(4-fluorophenyl)-N-(1-(6-methylpyridazin-3-yl)ethyl)-8-(morpholinosulfonyl)quinazolin-4-amine |

TABLE 1-continued

| List of preferred compounds of Formula (I) | | |
|---|---|---|
| Ex. N. | Structure | Chemical Name |
| Example 11 | 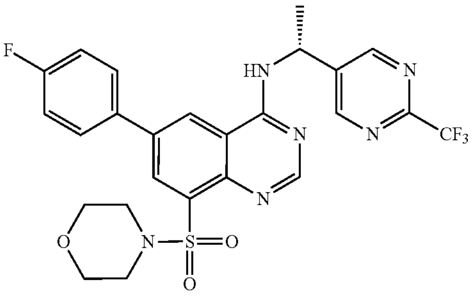 | ((R)-6-(4-fluorophenyl)-8-(morpholinosulfonyl)-N-(1-(2-(trifluoromethyl)pyrimidin-5-yl)ethyl)quinazolin-4-amine |
| Example 12 | 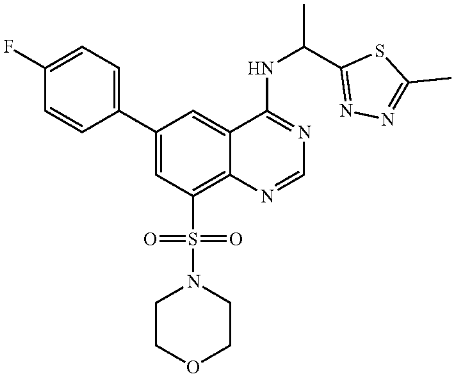 [SMILES: Cc1nnc(C(C)Nc2ncnc3c(S(=O)(=O)N4CCOCC4)cc(-c4ccc(F)cc4)cc23)s1] | (Rac)-6-(4-fluorophenyl)-N-(1-(5-methyl-1,3,4-thiadiazol-2-yl)ethyl)-8-(morpholinosulfonyl)quinazolin-4-amine |
| Example 13 | 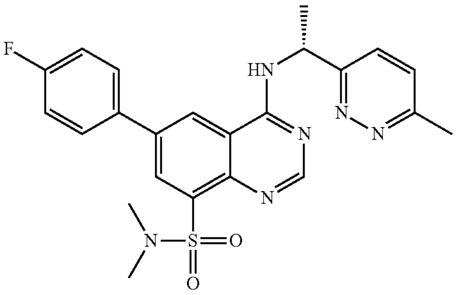 [SMILES: Cc1ccc([C@@H](C)Nc2ncnc3c(S(=O)(=O)N(C)C)cc(-c4ccc(F)cc4)cc23)nn1] | (R)-6-(4-fluorophenyl)-N,N-dimethyl-4-((1-(6-methylpyridazin-3-yl)ethyl)amino)quinazoline-8-sulfonamide |
| Example 14 | 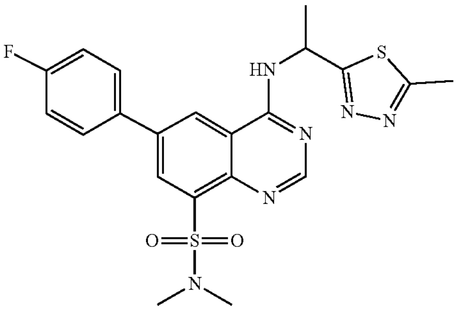 [SMILES: Cc1nnc(C(C)Nc2ncnc3c(S(=O)(=O)N(C)C)cc(-c4ccc(F)cc4)cc23)s1] | 6-(4-fluorophenyl)-N,N-dimethyl-4-((1-(5-methyl-1,3,4-thiadiazol-2-yl)ethyl)amino)quinazoline-8-sulfonamide |

TABLE 1-continued

List of preferred compounds of Formula (I)

| Ex. N. | Structure | Chemical Name |
|---|---|---|
| Example 15 | 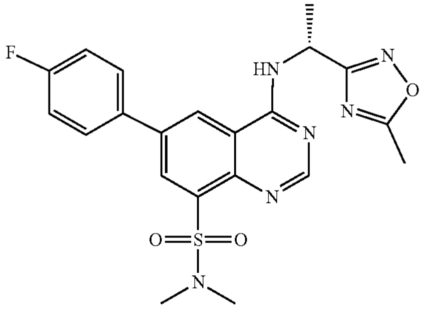 [SMILES: Cc1nc([C@@H](C)Nc2ncnc3c(S(=O)(=O)N(C)C)cc(-c4ccc(F)cc4)cc23)no1] | 6-(4-fluorophenyl)-N,N-dimethyl-4-((1-(5-methyl-1,2,4-oxadiazol-3-yl)ethyl)amino)quinazoline-8-sulfonamide |
| Example 16 | | (R)-8-((3,3-difluoropyrrolidin-1-yl) sulfonyl)-6-(4-fluorophenyl)-N-(1-(6-methylpyridazin-3-yl)ethyl)quinazolin-4-amide |
| Example 17 | 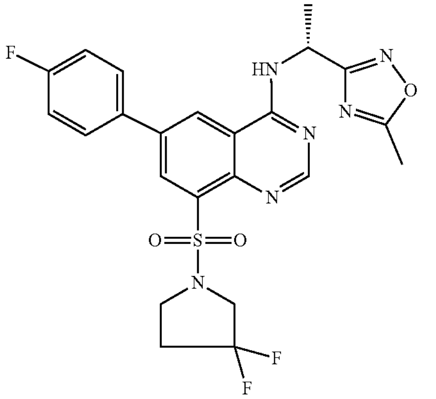 [SMILES: Cc1nc([C@@H](C)Nc2ncnc3c(S(=O)(=O)N4CCC(F)(F)C4)cc(-c4ccc(F)cc4)cc23)no1] | (R)-8-((3,3-difluoropyrrolidin-1-yl)sulfonyl)-6-(4-fluorophenyl)-N-(1-(5-methyl-1,2,4-oxadiazol-3-yl)ethyl)quinazolin-4-amine |
| Example 18 | 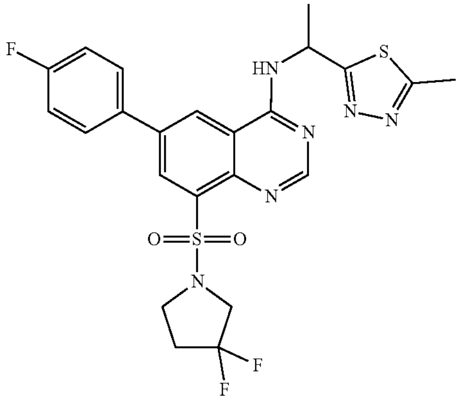 [SMILES: Cc1nnc(C(C)Nc2ncnc3c(S(=O)(=O)N4CCC(F)(F)C4)cc(-c4ccc(F)cc4)cc23)s1] | 8-((3,3-difluoropyrrolidin-1-yl)sulfonyl)-6-(4-fluorophenyl)-N-(1-(5-methyl-1,3,4-thiadiazol-2-yl)ethyl)quinazolin-4-amine |
| Example 19 | 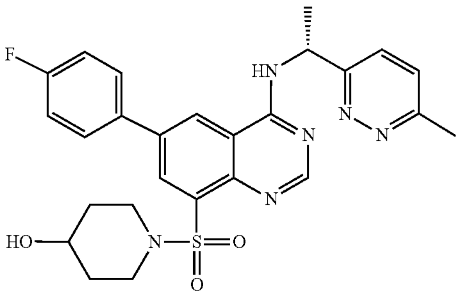 [SMILES: Cc1ccc([C@@H](C)Nc2ncnc3c(S(=O)(=O)N4CCC(O)CC4)cc(-c4ccc(F)cc4)cc23)nn1] | (R)-1-((6-(4-fluorophenyl)-4-((1-(6-methylpyridazin-3-yl)ethyl)amino)quinazolin-8-yl)sulfonyl)piperidin-4-ol |

TABLE 1-continued

List of preferred compounds of Formula (I)

| Ex. N. | Structure | Chemical Name |
|---|---|---|
| Example 20 | 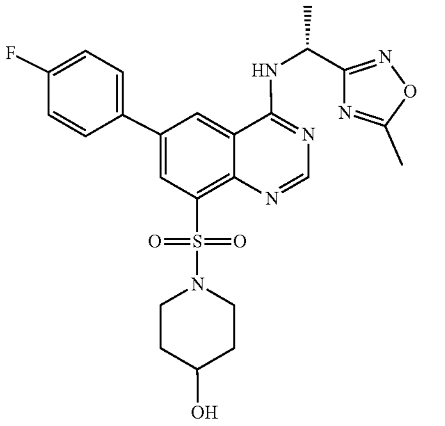 [SMILES: Cc1nc([C@@H](C)Nc2ncnc3c(S(=O)(=O)N4CCC(O)CC4)cc(-c4ccc(F)cc4)cc23)no1] | (R)-1-((6-(4-fluorophenyl)-4-((1-(5-methyl-1,2,4-oxadiazol-3-yl)ethyl)amino)quinazolin-8-yl)sulfonyl)piperidin-4-ol |
| Example 21 | 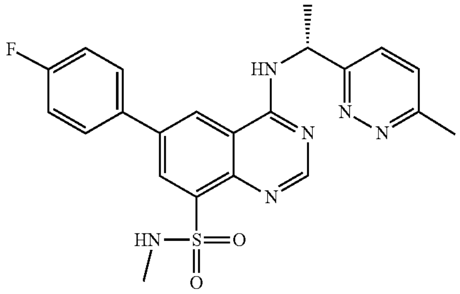 [SMILES: CNS(=O)(=O)c1cc(-c2ccc(F)cc2)cc2c(N[C@H](C)c3ccc(C)nn3)ncnc12] | (R)-6-(4-fluorophenyl)-N-methyl-4-((1-(6-methylpyridazin-3-yl)ethyl)amino)quinazoline-8-sulfonamide |
| Example 22 | 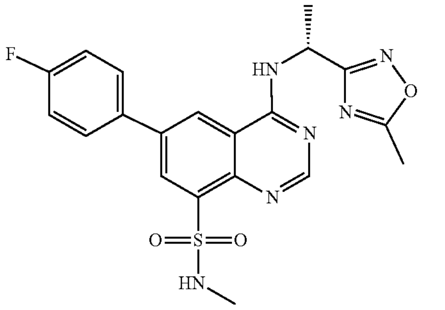 [SMILES: CNS(=O)(=O)c1cc(-c2ccc(F)cc2)cc2c(N[C@H](C)c3noc(C)n3)ncnc12] | (R)-6-(4-fluorophenyl)-N-methyl-4-((1-(5-methyl-1,2,4-oxadiazol-3-yl)ethyl)amino)quinazoline-8-sulfonamide |
| Example 23 | 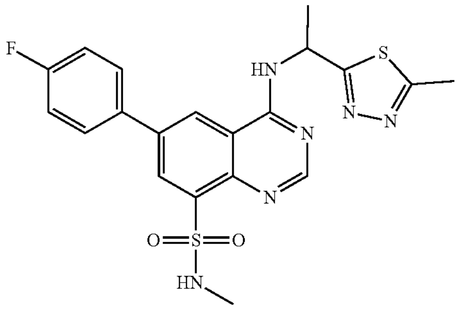 [SMILES: CNS(=O)(=O)c1cc(-c2ccc(F)cc2)cc2c(NC(C)c3nnc(C)s3)ncnc12] | (6-(4-fluorophenyl)-N-methyl-4-((1-(5-methyl-1,3,4-thiadiazol-2-yl)ethyl)amino)quinazoline-8-sulfonamide |

TABLE 1-continued

| List of preferred compounds of Formula (I) | | |
|---|---|---|
| Ex. N. | Structure | Chemical Name |
| Example 24 | 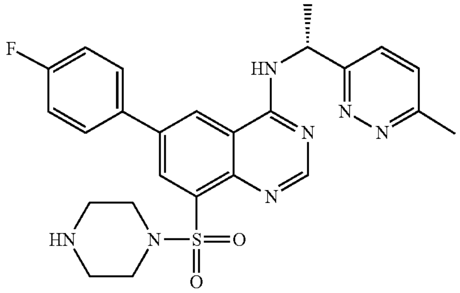 | (R)-6-(4-fluorophenyl)-N-(1-(6-methylpyridazin-3-yl)ethyl)-8-(piperazin-1-ylsulfonyl)quinazolin-4-amine |
| Example 25 | 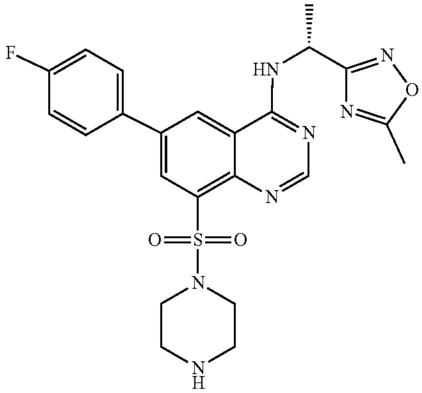 [SMILES: Cc1nc([C@@H](C)Nc2ncnc3c(S(=O)(=O)N4CCNCC4)cc(-c4ccc(F)cc4)cc23)no1] | (R)-6-(4-fluorophenyl)-N-(1-(5-methyl-1,2,4-oxadiazol-3-yl)ethyl)-8-(piperazin-1-ylsulfonyl)quinazolin-4-amine |
| Example 26 | 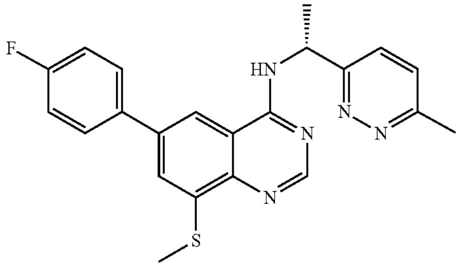 [SMILES: CSc1cc(-c2ccc(F)cc2)cc2c(N[C@H](C)c3ccc(C)nn3)ncnc12] | (R)-6-(4-fluorophenyl)-N-(1-(6-methylpyridazin-3-yl)ethyl)-8-(methylthio)quinazolin-4-amine |
| Example 27 | 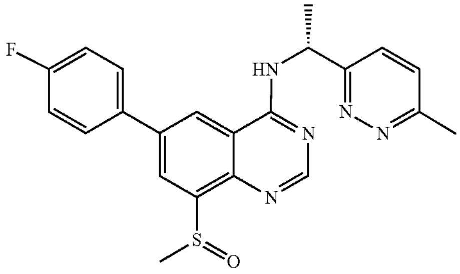 [SMILES: Cc1ccc([C@@H](C)Nc2ncnc3c(S(C)=O)cc(-c4ccc(F)cc4)cc23)nn1] | 6-(4-fluorophenyl)-N-((R)-1-(6-methylpyridazin-3-yl)ethyl)-8-(methylsulfinyl)quinazolin-4-amine |
| Example 28 | 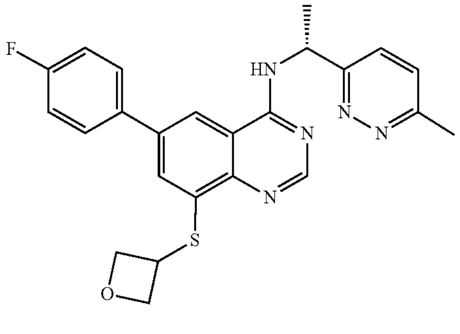 [SMILES: Cc1ccc([C@@H](C)Nc2ncnc3c(SC4COC4)cc(-c4ccc(F)cc4)cc23)nn1] | (R)-6-(4-fluorophenyl)-N-(1-(6-methylpyridazin-3-yl)ethyl)-8-(oxetan-3-ylthio)quinazolin-4-amine |

TABLE 1-continued

| List of preferred compounds of Formula (I) | | |
|---|---|---|
| Ex. N. | Structure | Chemical Name |
| Example 29 | 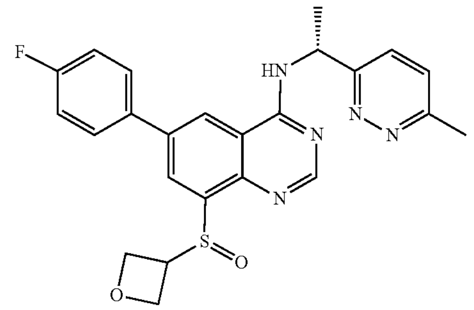 [SMILES: Cc1ccc([C@@H](C)Nc2ncnc3c(S(=O)C4COC4)cc(-c4ccc(F)cc4)cc23)nn1] | 6-(4-fluorophenyl)-N-((R)-1-(6-methylpyridazin-3-yl)ethyl)-8-(oxetan-3-ylsulfinyl)quinazolin-4-amine |
| Example 30 | 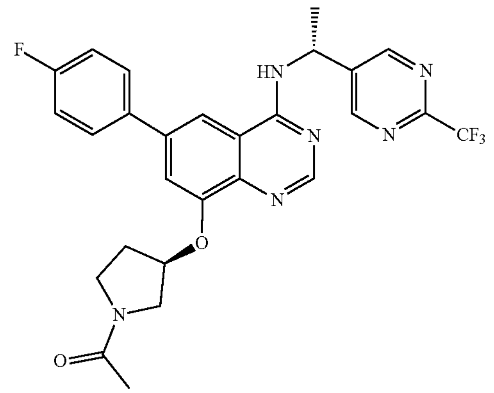 [SMILES: CC(=O)N1CC[C@@H](Oc2cc(-c3ccc(F)cc3)cc3c(N[C@H](C)c4cnc(C(F)(F)F)nc4)ncnc23)C1] | (1-((S)-3-((6-(4-fluorophenyl)-4-(((R)-1-(2-(trifluoromethyl)pyrimidin-5-yl)ethyl)amino)quinazolin-8-yl)oxy)pyrrolidin-1-yl)ethan-1-one |
| Example 31 | 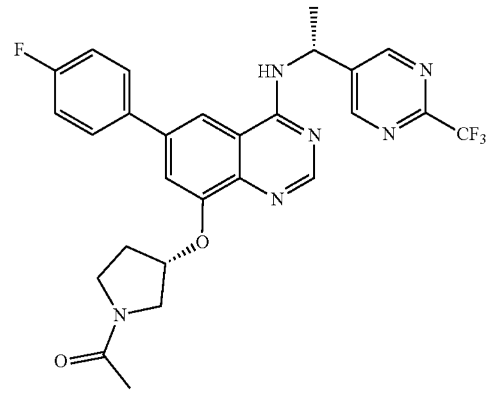 [SMILES: CC(=O)N1CC[C@H](Oc2cc(-c3ccc(F)cc3)cc3c(N[C@H](C)c4cnc(C(F)(F)F)nc4)ncnc23)C1] | (1-((R)-3-((6-(4-fluorophenyl)-4-(((R)-1-(2-(trifluoromethyl)pyrimidin-5-yl)ethyl)amino)quinazolin-8-yl)oxy)pyrrolidin-1-yl)ethan-1-one |
| Example 32 | 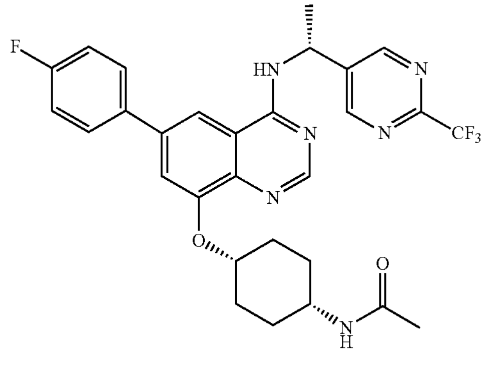 [SMILES: CC(=O)N[C@H]1CC[C@@H](Oc2cc(-c3ccc(F)cc3)cc3c(N[C@H](C)c4cnc(C(F)(F)F)nc4)ncnc23)CC1] | N-((1S,4s)-4-((6-(4-fluorophenyl)-4-(((R)-1-(2-(trifluoromethyl)pyrimidin-5-yl)ethyl)amino)quinazolin-8-yl)oxy)cyclohexyl)acetamide |

TABLE 1-continued

List of preferred compounds of Formula (I)

| Ex. N. | Structure | Chemical Name |
|---|---|---|
| Example 33 | 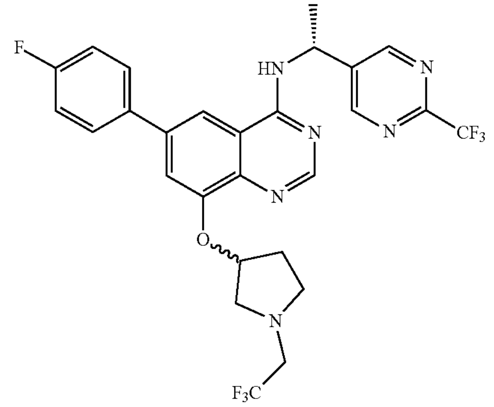 [SMILES: C[C@@H](Nc1ncnc2c(OC3CCN(CC(F)(F)F)C3)cc(-c3ccc(F)cc3)cc12)c1cnc(C(F)(F)F)nc1] | 6-(4-fluorophenyl)-8-((1-(2,2,2-trifluoroethyl)pyrrolidin-3-yl)oxy)-N-((R)-1-(2-(trifluoromethyl)pyrimidin-5-yl)ethyl)quinazolin-4-amine |
| Example 34 | 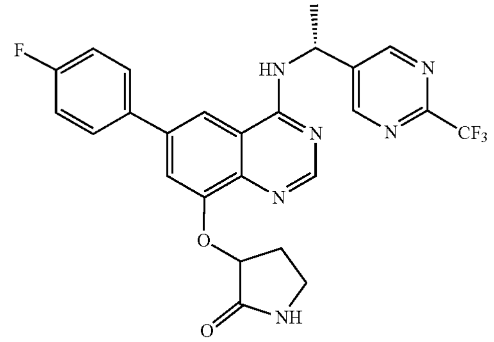 [SMILES: C[C@@H](Nc1ncnc2c(OC3CCNC3=O)cc(-c3ccc(F)cc3)cc12)c1cnc(C(F)(F)F)nc1] | 3-((6-(4-fluorophenyl)-4-(((R)-1-(2-(trifluoromethyl)pyrimidin-5-yl)ethyl)amino)quinazolin-8-yl)oxy)pyrrolidin-2-one |
| Example 35 | 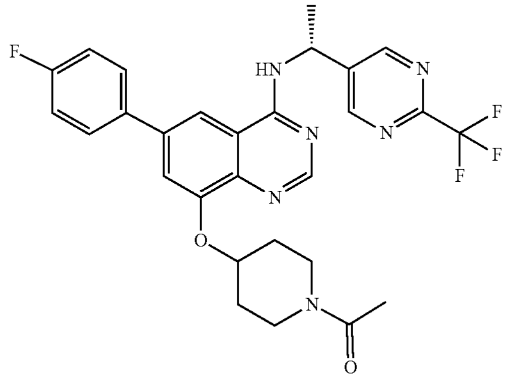 [SMILES: CC(=O)N1CCC(Oc2cc(-c3ccc(F)cc3)cc3c(N[C@H](C)c4cnc(C(F)(F)F)nc4)ncnc23)CC1] | (R)-1-(4-((6-(4-fluorophenyl)-4-((1-(2-(trifluoromethyl)pyrimidin-5-yl)ethyl)amino)quinazolin-8-yl)oxy)piperidin-1-yl)ethan-1-one |
| Example 36 | | (R)-6-(4-fluorophenyl)-8-((1-(2,2,2-trifluoroethyl)piperidin-4-yl)oxy)-N-(1-(2-(trifluoromethyl) pyrimidin-5-yl)ethyl) quinazolin-4-amine |

TABLE 1-continued

| List of preferred compounds of Formula (I) | | |
|---|---|---|
| Ex. N. | Structure | Chemical Name |
| Example 37 | 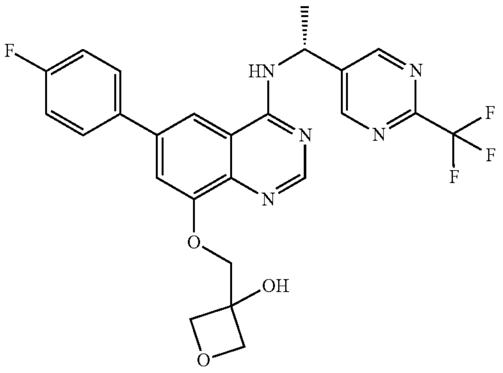 [SMILES: C[C@@H](Nc1ncnc2c(OCC3(O)COC3)cc(-c3ccc(F)cc3)cc12)c1cnc(C(F)(F)F)nc1] | (R)-3-(((6-(4-fluorophenyl)-4-((1-(2-(trifluoromethyl)pyrimidin-5-yl)ethyl)amino)quinazolin-8-yl)oxy)methyl)oxetan-3-ol |
| Example 38 | 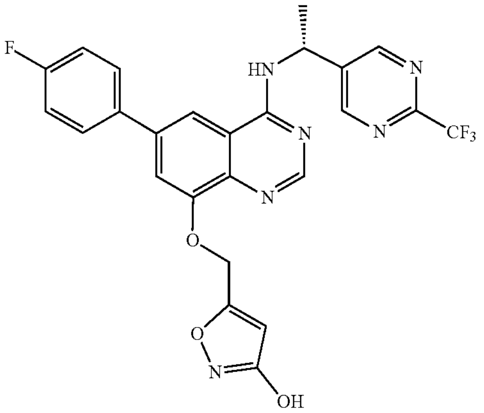 [SMILES: C[C@@H](Nc1ncnc2c(OCc3cc(O)no3)cc(-c3ccc(F)cc3)cc12)c1cnc(C(F)(F)F)nc1] | (R)-5-(((6-(4-fluorophenyl)-4-((1-(2-(trifluoromethyl)pyrimidin-5-yl)ethyl)amino)quinazolin-8-yl)oxy)methyl)isoxazol-3-ol |
| Example 39 | 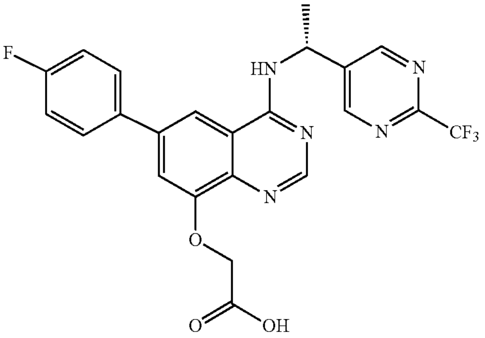 [SMILES: C[C@@H](Nc1ncnc2c(OCC(=O)O)cc(-c3ccc(F)cc3)cc12)c1cnc(C(F)(F)F)nc1] | (R)-2-((6-(4-fluorophenyl)-4-((1-(2-(trifluoromethyl)pyrimidin-5-yl)ethyl)amino)quinazolin-8-yl)oxy)acetic acid |
| Example 40 | 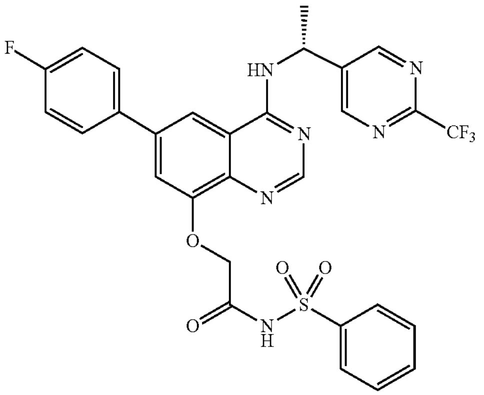 [SMILES: C[C@@H](Nc1ncnc2c(OCC(=O)NS(=O)(=O)c3ccccc3)cc(-c3ccc(F)cc3)cc12)c1cnc(C(F)(F)F)nc1] | (R)-2-((6-(4-fluorophenyl)-4-((1-(2-(trifluoromethyl)pyrimidin-5-yl)ethyl)amino)quinazolin-8-yl)oxy)-N-(phenylsulfonyl)acetamide |

TABLE 1-continued

| List of preferred compounds of Formula (I) | | |
|---|---|---|
| Ex. N. | Structure | Chemical Name |
| Example 41 | 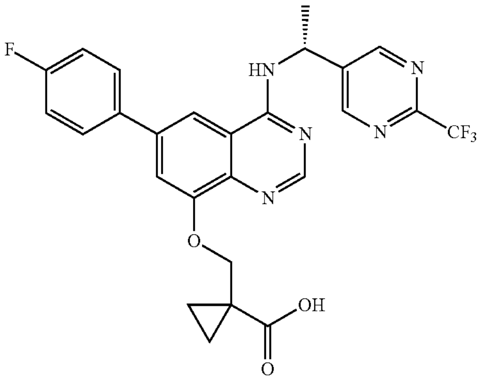 [SMILES: C[C@@H](Nc1ncnc2c(OCC3(C(=O)O)CC3)cc(-c3ccc(F)cc3)cc12)c1cnc(C(F)(F)F)nc1] | (R)-1-(((6-(4-fluorophenyl)-4-((1-(2-(trifluoromethyl)pyrimidin-5-yl)ethyl)amino)quinazolin-8-yl)oxy)methyl)cyclopropane-1-carboxylic acid |
| Example 42 | 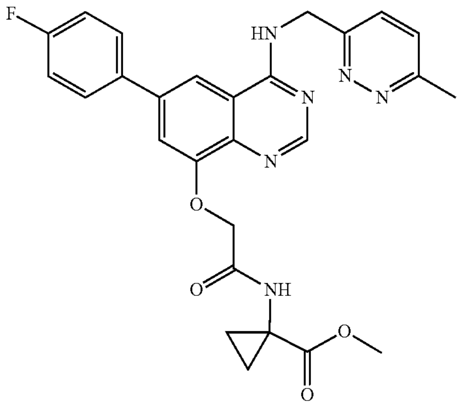 [SMILES: COC(=O)C1(NC(=O)COc2cc(-c3ccc(F)cc3)cc3c(NCc4ccc(C)nn4)ncnc23)CC1] | Methyl 1-(2-((6-(4-fluorophenyl)-4-(((6-methylpyridazin-3-yl)methyl)amino)quinazolin-8-yl)oxy)acetamido)cyclopropane-1-carboxylate |
| Example 43 | 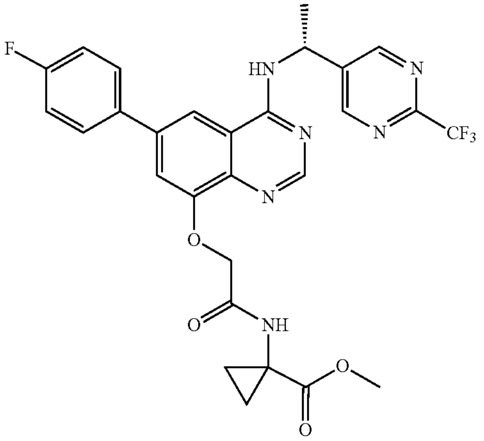 [SMILES: COC(=O)C1(NC(=O)COc2cc(-c3ccc(F)cc3)cc3c(N[C@H](C)c4cnc(C(F)(F)F)nc4)ncnc23)CC1] | Methyl (R)-1-(2-((6-(4-fluorophenyl)-4-((1-(2-(trifluoromethyl)pyrimidin-5-yl)ethyl)amino)quinazolin-8-yl)oxy)acetamido) cyclopropane-1-carboxylate |

TABLE 1-continued

| List of preferred compounds of Formula (I) | | |
|---|---|---|
| Ex. N. | Structure | Chemical Name |
| Example 44 | 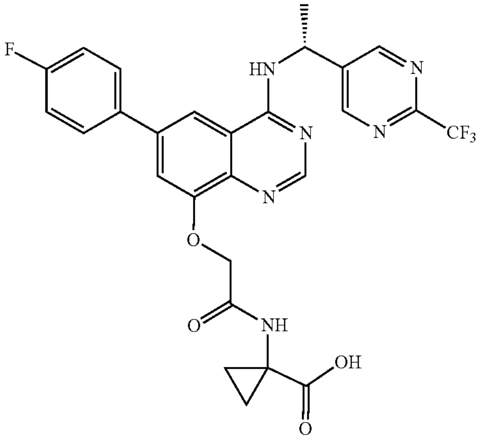 [SMILES: C[C@@H](Nc1ncnc2c(OCC(=O)NC3(C(=O)O)CC3)cc(-c3ccc(F)cc3)cc12)c1cnc(C(F)(F)F)nc1] | (R)-1-(2-((6-(4-fluorophenyl)-4-((1-(2-(trifluoromethyl)pyrimidin-5-yl)ethyl)amino)quinazolin-8-yl)oxy)acetamido)cyclopropane-1-carboxylic acid |
| Example 45 | 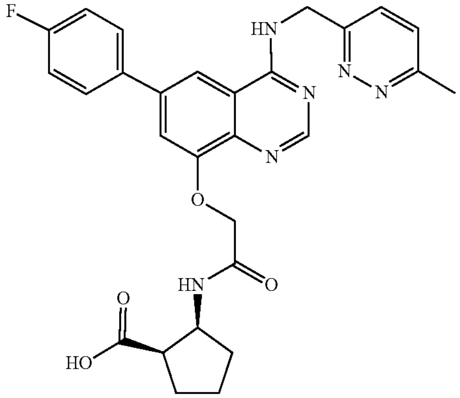 [SMILES: Cc1ccc(CNc2ncnc3c(OCC(=O)N[C@H]4CCC[C@H]4C(=O)O)cc(-c4ccc(F)cc4)cc23)nn1] | (1R,2S)-2-(2-((6-(4-fluorophenyl)-4-(((6-methylpyridazin-3-yl)methyl)amino)quinazolin-8-yl)oxy)acetamido)cyclopentane-1-carboxylic acid |
| Example 46 | 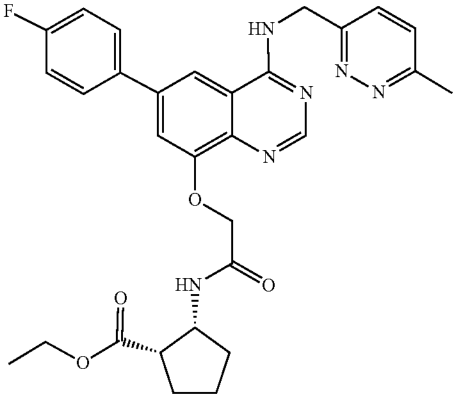 [SMILES: CCOC(=O)[C@H]1CCC[C@H]1NC(=O)COc1cc(-c2ccc(F)cc2)cc2c(NCc3ccc(C)nn3)ncnc12] | Ethyl (1S,2R)-2-(2-((6-(4-fluorophenyl)-4-(((6-methylpyridazin-3-yl)methyl)amino)quinazolin-8-yl)oxy)acetamido)cyclopentane-1-carboxylate |

TABLE 1-continued

| List of preferred compounds of Formula (I) | | |
|---|---|---|
| Ex. N. | Structure | Chemical Name |
| Example 47 | 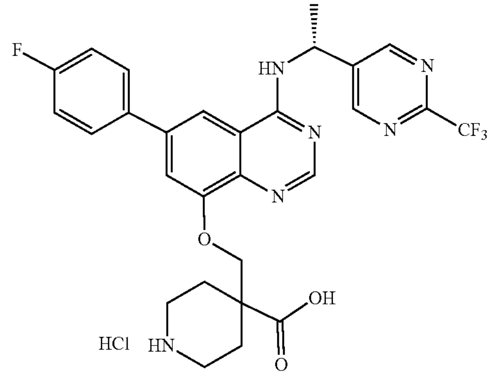 [SMILES: C[C@@H](Nc1ncnc2c(OCC3(C(=O)O)CCNCC3)cc(-c3ccc(F)cc3)cc12)c1cnc(C(F)(F)F)nc1 ; Cl] | (R)-4-(((6-(4-fluorophenyl)-4-((1-(2-(trifluoromethyl)pyrimidin-5-yl)ethyl)amino)quinazolin-8-yl)oxy)methyl)piperidine-4-carboxylic acid hydrochloride |
| Example 48 | 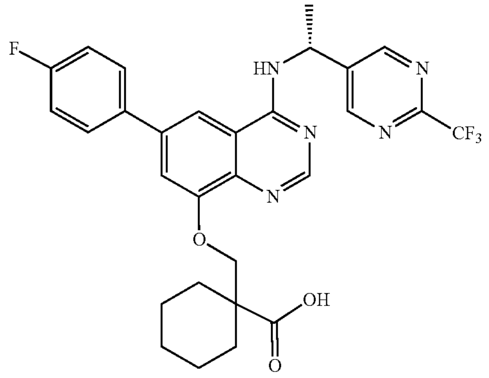 [SMILES: C[C@@H](Nc1ncnc2c(OCC3(C(=O)O)CCCCC3)cc(-c3ccc(F)cc3)cc12)c1cnc(C(F)(F)F)nc1] | (R)-1-(((6-(4-fluorophenyl)-4-((1-(2-(trifluoromethyl)pyrimidin-5-yl)ethyl)amino)quinazolin-8-yl)oxy)methyl)cyclohexane-1-carboxylic acid |
| Example 49 | 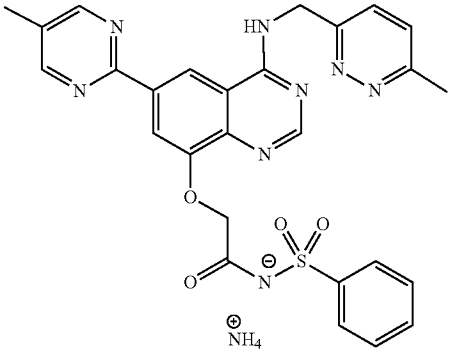 | Ammonium (2-((4-(((6-methylpyridazin-3-yl)methyl)amino)-6-(5-methylpyrimidin-2-yl)quinazolin-8-yl)oxy)acetyl)(phenylsulfonyl) amide |
| Example 50 | 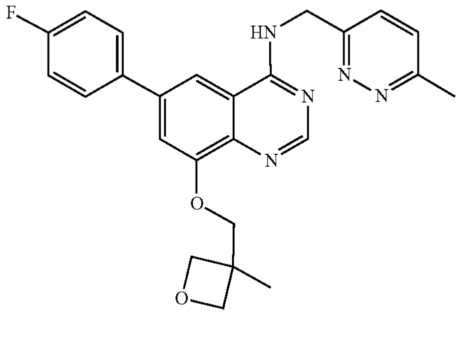 [SMILES: Cc1ccc(CNc2ncnc3c(OCC4(C)COC4)cc(-c4ccc(F)cc4)cc23)nn1] | 6-(4-fluorophenyl)-8-[(3-methyloxetan-3-yl)methoxy]-N-[(6-methylpyridazin-3-yl)methyl]quinazolin-4-amine |

TABLE 1-continued

| List of preferred compounds of Formula (I) | | |
|---|---|---|
| Ex. N. | Structure | Chemical Name |
| Example 51 | 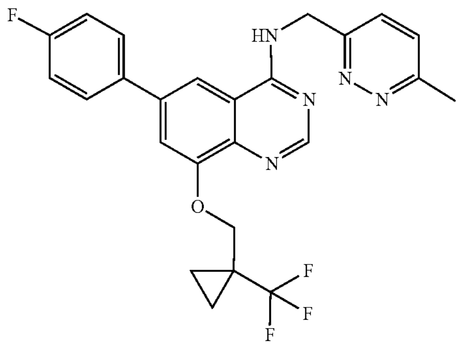 [SMILES: Cc1ccc(CNc2ncnc3c(OCC4(C(F)(F)F)CC4)cc(-c4ccc(F)cc4)cc23)nn1] | 6-(4-fluorophenyl)-N-[(6-methylpyridazin-3-yl)methyl]-8-[[1-(trifluoromethyl)cyclopropyl]methoxy]quinazolin-4-amine |
| Example 52 | 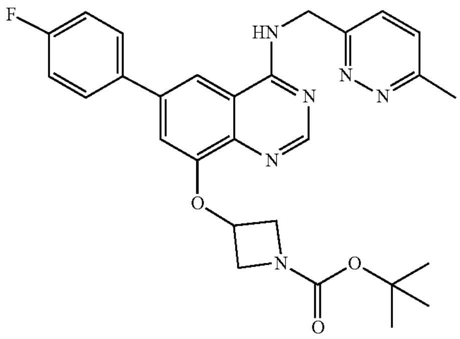 [SMILES: Cc1ccc(CNc2ncnc3c(OC4CN(C(=O)OC(C)(C)C)C4)cc(-c4ccc(F)cc4)cc23)nn1] | tert-butyl 3-[6-(4-fluorophenyl)-4-[(6-methylpyridazin-3-yl)methylamino]quinazolin-8-yl]oxyazetidine-1-carboxylate |
| Example 53 | 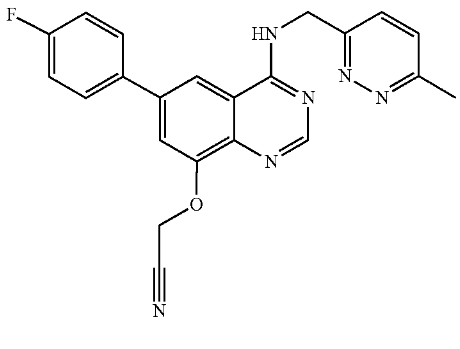 [SMILES: Cc1ccc(CNc2ncnc3c(OCC#N)cc(-c4ccc(F)cc4)cc23)nn1] | 2-[6-(4-fluorophenyl)-4-[(6-methylpyridazin-3-yl)methylamino]quinazolin-8-yl]oxyacetonitrile |
| Example 54 | 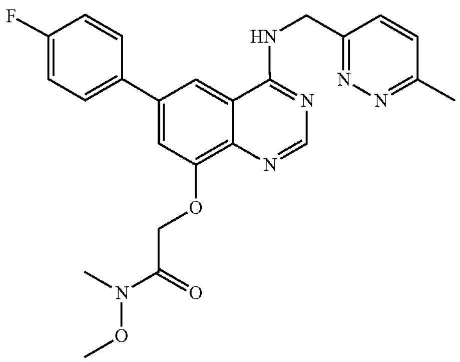 [SMILES: CON(C)C(=O)COc1cc(-c2ccc(F)cc2)cc2c(NCc3ccc(C)nn3)ncnc12] | 2-[6-(4-fluorophenyl)-4-[(6-methylpyridazin-3-yl)methylamino]quinazolin-8-yl]oxy-N-methoxy-N-methyl-acetamide |

TABLE 1-continued

List of preferred compounds of Formula (I)

| Ex. N. | Structure | Chemical Name |
|---|---|---|
| Example 55 | 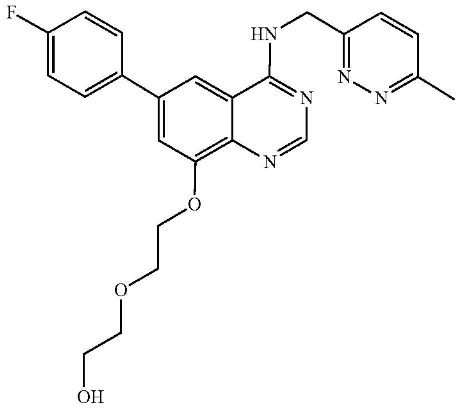 [SMILES: Cc1ccc(CNc2ncnc3c(OCCOCCO)cc(-c4ccc(F)cc4)cc23)nn1] | 2-[2-[6-(4-fluorophenyl)-4-[(6-methylpyridazin-3-yl)methylamino]quinazolin-8-yloxyethoxy]ethanol |
| Example 56 | 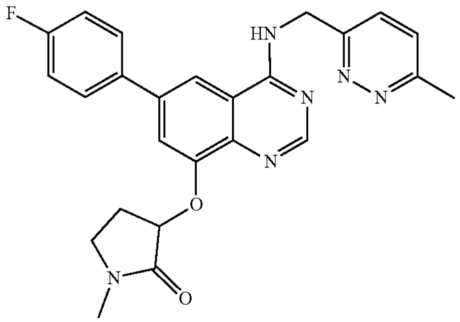 [SMILES: Cc1ccc(CNc2ncnc3c(OC4CCN(C)C4=O)cc(-c4ccc(F)cc4)cc23)nn1] | 3-[6-(4-fluorophenyl)-4-[(6-methylpyridazin-3-yl)methylamino]quinazolin-8-yl]oxy-1-methyl-pyrrolidin-2-one |
| Example 57 | 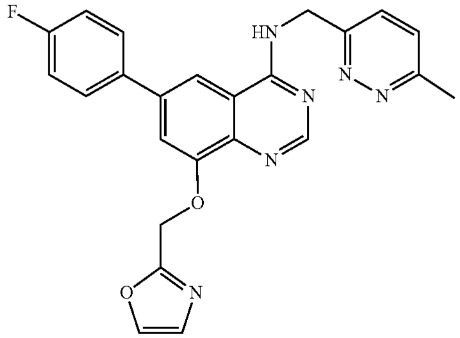 [SMILES: Cc1ccc(CNc2ncnc3c(OCc4ncco4)cc(-c4ccc(F)cc4)cc23)nn1] | 6-(4-fluorophenyl)-N-[(6-methylpyridazin-3-yl)methyl]-8-(oxazol-2-ylmethoxy)quinazolin-4-amine |
| Example 58 | 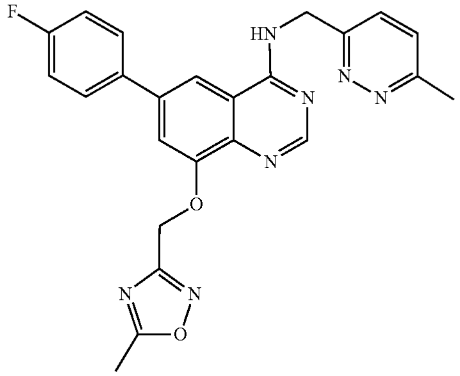 [SMILES: Cc1ccc(CNc2ncnc3c(OCc4noc(C)n4)cc(-c4ccc(F)cc4)cc23)nn1] | 6-(4-fluorophenyl)-8-[(5-methyl-1,2,4-oxadiazol-3-yl)methoxy]-N-[(6-methylpyridazin-3-yl)methyl]quinazolin-4-amine |

TABLE 1-continued

| List of preferred compounds of Formula (I) | | |
|---|---|---|
| Ex. N. | Structure | Chemical Name |
| Example 59 | 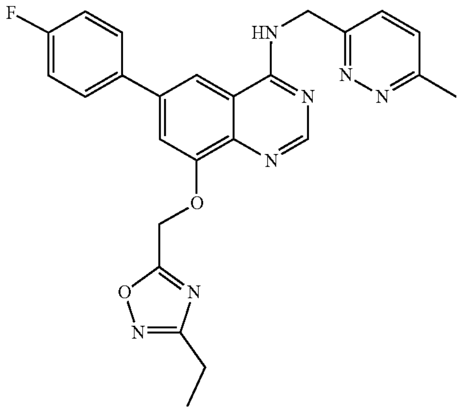 [SMILES: CCc1noc(COc2cc(-c3ccc(F)cc3)cc3c(NCc4ccc(C)nn4)ncnc23)n1] | 8-[(3-ethyl-1,2,4-oxadiazol-5-yl)methoxy]-6-(4-fluorophenyl)-N-[(6-methylpyridazin-3-yl)methyl]quinazolin-4-amine |
| Example 60 | 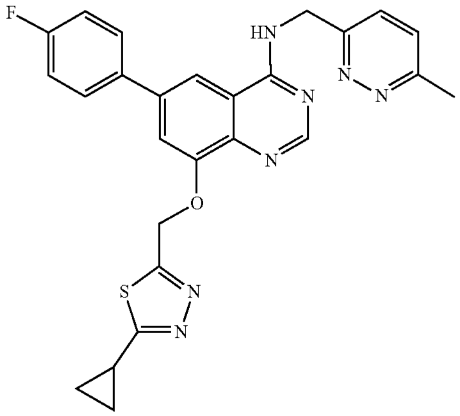 [SMILES: Cc1ccc(CNc2ncnc3c(OCc4nnc(C5CC5)s4)cc(-c4ccc(F)cc4)cc23)nn1] | 8-[(5-cyclopropyl-1,3,4-thiadiazol-2-yl)methoxy]-6-(4-fluorophenyl)-N-[(6-methylpyridazin-3-yl)methyl]quinazolin-4-amine |
| Example 61 | 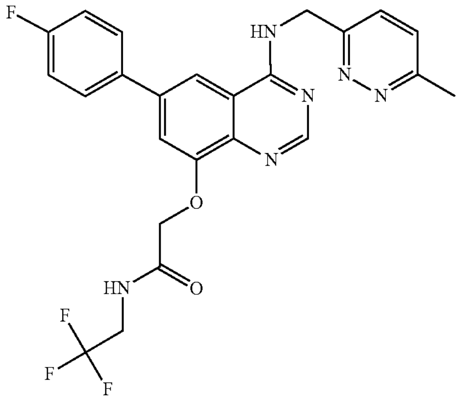 [SMILES: Cc1ccc(CNc2ncnc3c(OCC(=O)NCC(F)(F)F)cc(-c4ccc(F)cc4)cc23)nn1] | 2-[6-(4-fluorophenyl)-4-[(6-methylpyridazin-3-yl)methylamino]quinazolin-8-yl]oxy-N-(2,2,2-trifluoroethyl)acetamide |

TABLE 1-continued

| List of preferred compounds of Formula (I) | | |
|---|---|---|
| Ex. N. | Structure | Chemical Name |
| Example 62 | 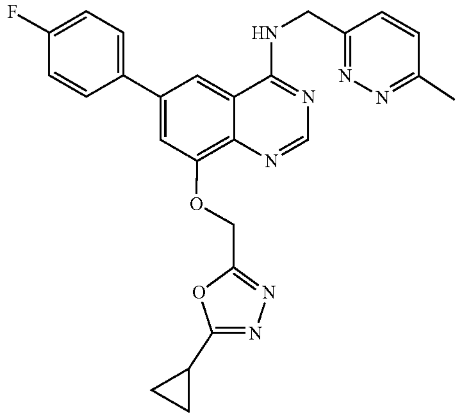 [SMILES: Cc1ccc(CNc2ncnc3c(OCc4nnc(C5CC5)o4)cc(-c4ccc(F)cc4)cc23)nn1] | 8-((5-cyclopropyl-1,3,4-oxadiazol-2-yl)methoxy)-6-(4-fluorophenyl)-N-((6-methylpyridazin-3-yl)methyl)quinazolin-4-amine |
| Example 63 | 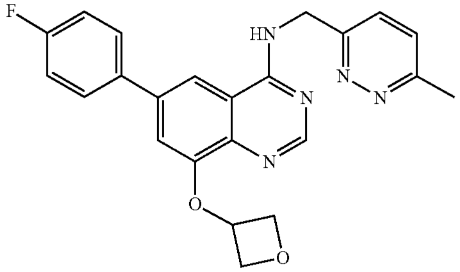 [SMILES: Cc1ccc(CNc2ncnc3c(OC4COC4)cc(-c4ccc(F)cc4)cc23)nn1] | 6-(4-fluorophenyl)-N-((6-methylpyridazin-3-yl)methyl)-8-(oxetan-3-yloxy)quinazolin-4-amine |
| Example 64 | 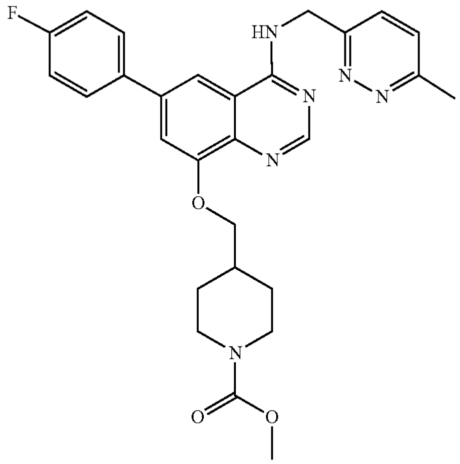 [SMILES: COC(=O)N1CCC(COc2cc(-c3ccc(F)cc3)cc3c(NCc4ccc(C)nn4)ncnc23)CC1] | Methyl 4-[[6-(4-fluorophenyl)-4-[(6-methylpyridazin-3-yl)methylamino]quinazolin-8-yl]oxymethyl]piperidine-1-carboxylate |
| Example 65 | 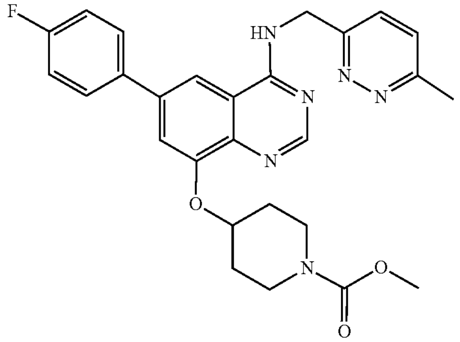 [SMILES: COC(=O)N1CCC(Oc2cc(-c3ccc(F)cc3)cc3c(NCc4ccc(C)nn4)ncnc23)CC1] | Methyl 4-[6-(4-fluorophenyl)-4-[(6-methylpyridazin-3-yl)methylamino]quinazolin-8-yl]oxypiperidine-1-carboxylate |

TABLE 1-continued

| List of preferred compounds of Formula (I) | | |
|---|---|---|
| Ex. N. | Structure | Chemical Name |
| Example 66 | 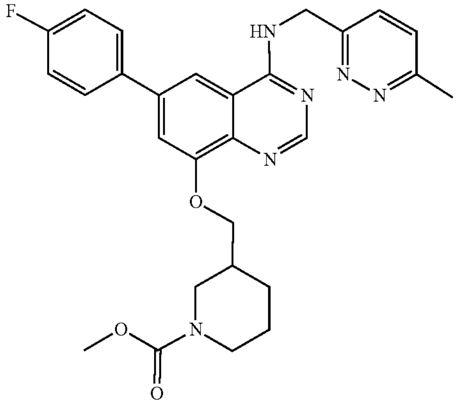 [SMILES: COC(=O)N1CCCC(COc2cc(-c3ccc(F)cc3)cc3c(NCc4ccc(C)nn4)ncnc23)C1] | Methyl 3-[6-(4-fluorophenyl)-4-[(6-methylpyridazin-3-yl)methylamino]quinazolin-8-yl]oxymethyl]piperidine-1-carboxylate |
| Example 67 | 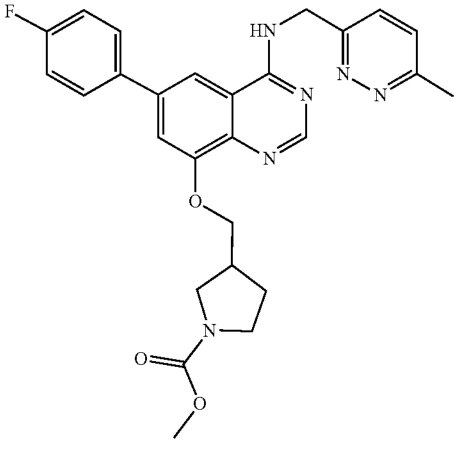 [SMILES: COC(=O)N1CCC(COc2cc(-c3ccc(F)cc3)cc3c(NCc4ccc(C)nn4)ncnc23)C1] | Methyl 3-[[6-(4-fluorophenyl)-4-[(6-methylpyridazin-3-yl)methylamino]quinazolin-8-yl]oxymethyl]pyrrolidine-1-carboxylate |
| Example 68 | 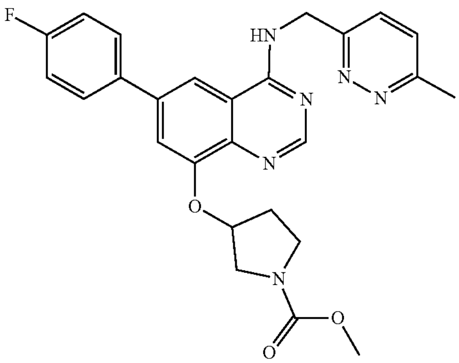 [SMILES: COC(=O)N1CCC(Oc2cc(-c3ccc(F)cc3)cc3c(NCc4ccc(C)nn4)ncnc23)C1] | Methyl 3-[6-(4-fluorophenyl)-4-[(6-methylpyridazin-3-yl)methylamino]quinazolin-8-yl]oxypyrrolidine-1-carboxylate |

In one preferred embodiment, the invention refers to a compound of formula (I),

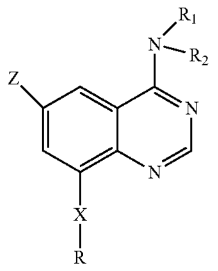

wherein

X is selected from S or SO;

Z is aryl, wherein such aryl may be optionally substituted by one or more groups selected from ($C_1$-$C_3$)alkyl-, halo and ($C_1$-$C_6$)haloalkyl-;

$R_1$ is H or ($C_1$-$C_4$)alkyl;

$R_2$ is heteroaryl($C_1$-$C_4$)alkyl-, wherein any of such alkyl and heteroaryl may be optionally substituted by one or more groups selected from ($C_1$-$C_3$)alkyl, ($C_1$-$C_6$)haloalkyl and halo;

R is selected from the group consisting of ($C_1$-$C_6$)alkyl- and ($C_3$-$C_8$)heterocycloalkyl-.

In one preferred embodiment, the invention refers to a compound of formula (I), wherein X is O, represented b the formula Ia (Ia)

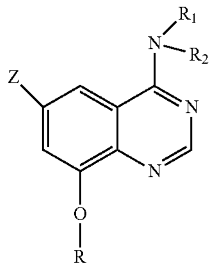

wherein

Z is selected from the group consisting of heteroaryl, aryl, wherein any of such heteroaryl and aryl may be optionally substituted by one or more groups selected from ($C_1$-$C_3$)alkyl-, halo and ($C_1$-$C_6$)haloalkyl-;

$R_1$ is H or ($C_1$-$C_4$)alkyl;

$R_2$ is heteroaryl($C_1$-$C_4$)alkyl-, wherein any of such alkyl and heteroaryl may be optionally substituted by one or more groups selected from ($C_1$-$C_3$)alkyl, ($C_1$-$C_6$)haloalkyl and halo;

R is selected from the group consisting of ($C_1$-$C_6$)alkyl-, ($C_1$-$C_6$)alkyl-CN, ($C_1$-$C_6$)haloalkyl, —$NR_AR_B$, ($C_3$-$C_8$)heterocycloalkyl-($C_1$-$C_6$)alkyl-, ($C_3$-$C_8$)heterocycloalkyl-, ($C_3$-$C_8$)heteroaryl-($C_1$-$C_6$)alkyl-, ($C_3$-$C_8$)cycloalkyl-($C_1$-$C_6$)alkyl-, ($C_3$-$C_8$)cycloalkyl-, $R_A$O—($C_1$-$C_6$)alkyl-O—($C_1$-$C_6$)alkyl-, $R_A$NH—C(O)—($C_1$-$C_4$)alkyl-, $R_AR_B$N—C(O)—($C_1$-$C_4$)alkyl-, $R_A$O—C(O)($C_1$-$C_6$)alkyl-, wherein any of such heterocycloalkyl is substituted by one or more groups selected from —OH, —C(O)$R_A$, —C(O)O$R_A$, ($C_1$-$C_6$)haloalkyl, —NH—C(O)$R_1$, and oxo;

any of such cycloalkyl is substituted by one or more groups selected from —C(O)O$R_A$ and ($C_1$-$C_6$)haloalkyl-, any of such heteraryl may be optionally substituted by one or more groups selected from ($C_1$-$C_6$)alkyl-, —OH and ($C_3$-$C_6$)cycloalkyl-;

$R_A$ and $R_B$ are at each occurrence independently H or selected from the group consisting of ($C_1$-$C_6$)alkyl-, ($C_1$-$C_6$)haloalkyl-, —$OR_1$, —$SO_2R_C$ and ($C_3$-$C_6$)cycloalkyl wherein such cycloalkyl may be optionally substituted by one or more —C(O)O$R_1$;

$R_C$ is aryl.

In one preferred embodiment, the invention refers to a compound of formula (I), wherein X is $SO_2$, represented by the formula Ib (Ib)

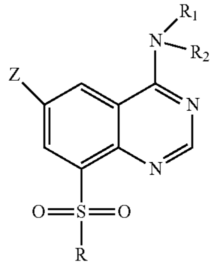

wherein

Z is aryl, wherein any of such aryl may be optionally substituted by one or more groups selected from ($C_1$-$C_3$)alkyl-, halo and ($C_1$-$C_6$)haloalkyl-;

$R_1$ is H or ($C_1$-$C_4$)alkyl;

$R_2$ is heteroaryl($C_1$-$C_4$)alkyl-, wherein any of such alkyl and heteroaryl may be optionally substituted by one or more groups selected from ($C_1$-$C_3$)alkyl, ($C_1$-$C_6$)haloalkyl and halo;

R is —$NR_AR_B$;

$R_A$ and $R_B$ are at each occurrence independently H or ($C_1$-$C_6$)alkyl-, or alternatively $R_A$ and $R_B$ may form together with the nitrogen atom to which they are attached a 5 or 6 membered saturated heterocyclic monocyclic ring system optionally containing a further heteroatom which is nitrogen or oxygen, which may be optionally substituted by one or more groups selected from halo, —$OR_1$.

The compounds of formula (I) including all the compounds or at least one of the here above listed can be generally prepared according to the procedure outlined in detail in the Schemes shown below using generally known methods.

Scheme 1

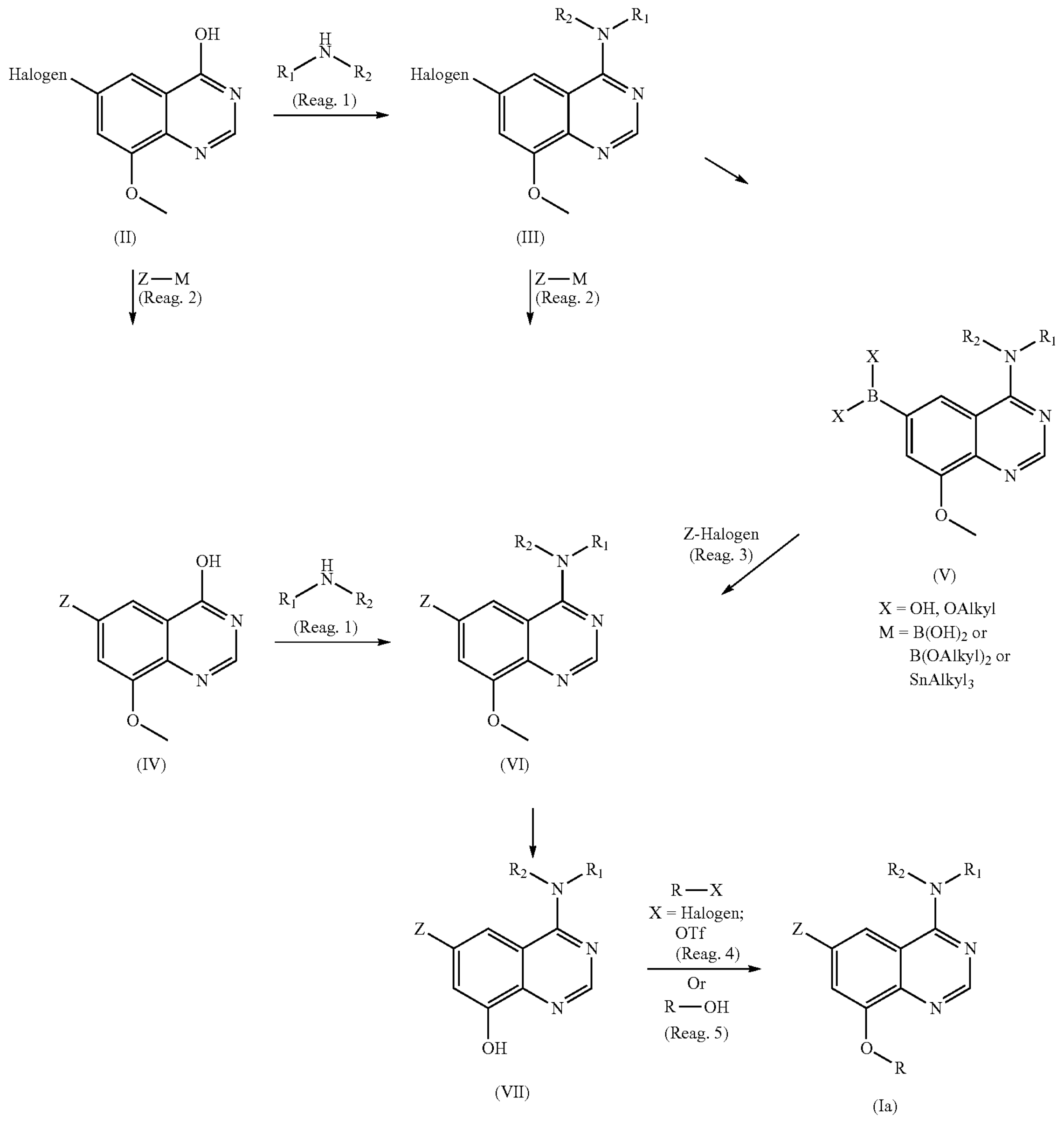

In one embodiment of the present invention, compound (Ia) may be prepared according to SCHEME 1 from compound (II). Compound (II) was prepared following the procedure described in *J. Med Chem.*, 2015, 58 (8), 3548-3571.

Compound (III) may be prepared from Compound (II) by a deoxyamination reaction mediated by coupling reagents like PyBOP with a suitable amine (Reag.1).

Compound (VI) may be prepared from Compound (III) by a metal-catalyzed cross coupling reactions like Stille or Suzuki or similars as described in "Transition Metals for Organic Synthesis", 2nd Ed, 1, 2004 with a suitable reagent like (Reag. 2).

Alternatively Compound (V) may be prepared from Compound (III) by metal-catalyzed Miyaura borylation reaction.

Compound (VI) may be prepared from Compound (V) by a metal-catalyzed cross coupling reactions like Stille, Suzuki or similar as described in "Transition Metals for Organic Synthesis", 2nd Ed, 1, 2004 with a suitable organohalogen compound like (Reag. 3).

In another embodiment, compound (IV) was prepared starting from compound (II) by a metal-catalyzed cross coupling reactions like Stille, Suzuki or similars as described in "Transition Metals for Organic Synthesis", 2nd Ed, 1, 2004 with a suitable Organometallic reagent like (Reag.2).

Compound (VI) may be prepared from Compound (IV) by deoxyamination reaction mediated by reagents like PyBOP or similar with a suitable amine (Reag.1).

Compound (VII) may be prepared from Compound (VI) by means of dealkylation reactions mediated by strong Lewis acids like $BBr_3$ or similar.

Compounds (Ia) were prepared from compounds (VII) by alkylation with a suitable alkylating agent (Reag. 4) like, alkyl chlorides, bromides, iodides, mesylates, tosylates or similar.

Alternatively, compounds (Ia) may be prepared from compounds (VII) and a suitable alcohol (Reag. 5) by Mitsunobu-like reactions mediated, for example, by DEAD/$PPh_3$, DIAD/$PPh_3$ or CMT.

Some compounds (Ia) may contain a protected hydroxyl or amino group which were then removed under well-known procedures.

Compound (XV) may be prepared from Compound (XIV) by a deoxyahalogenation reaction mediated by reagents like, for example, Phosphorous oxychloride.

Compound (Ia) may be prepared from Compound (XV) by a reaction with a suitable amine (Reag.1) in the presence of a base like, for example TEA or DIPEA Some compounds (Ia) may contain a protected hydroxyl or amino group which were then removed under well known procedures.

Scheme 2

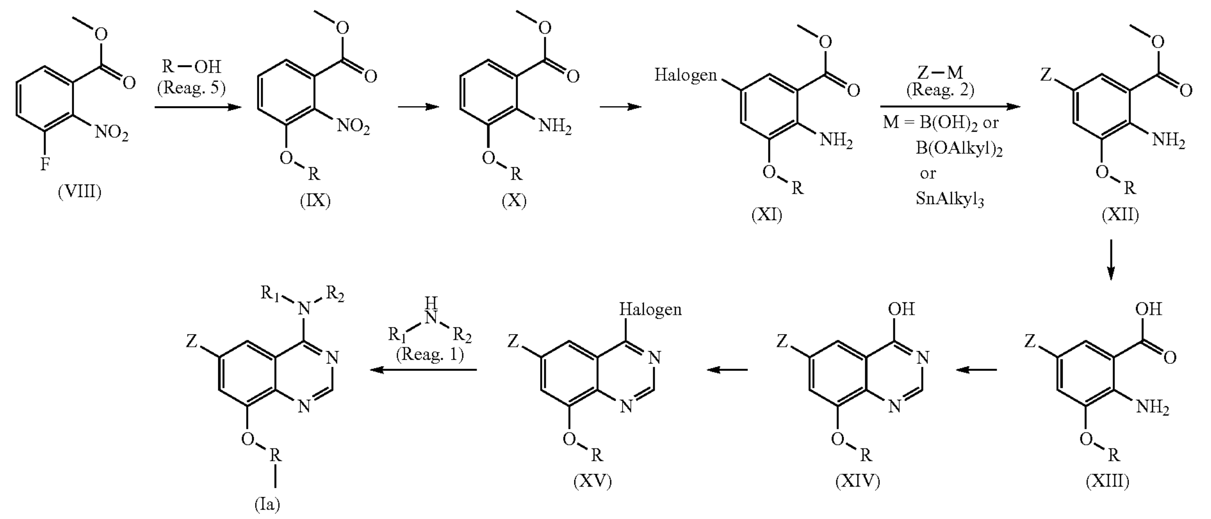

(VIII) (IX) (X) (XI) (XII) (XIII) (XIV) (XV) (Ia)

In one embodiment of the present invention, compound (Ia) may be prepared according to SCHEME 2 from compound (VIII).

Compounds (IX) may be prepared from compounds (VIII) and a suitable alcohol (Reag. 5) by aromatic substitution in the presence of an appropriate base like, for example, Potassium Carbonate ($K_2CO_3$).

Compounds (X) may be prepared from compounds (IX) by hydrogenation in the presence of a suitable catalyst like, for example, Palladium on carbon.

Compound (XI) may be prepared from Compound (X) by Halogention with suitable reagents like Bromine, NBS, NIS, Iodine, iodonium salts or similar.

Compound (XII) may be prepared from Compound (XI) by metal-catalyzed cross coupling reactions like Stille, Suzuki or similar ones with a suitable organometallic reagents (Reag. 2) like, for example, organoboron compounds.

Compound (XIII) may be prepared from Compound (XII) by ester hydrolysis mediated by a suitable base like, for example, lithium hydroxide (LiOH).

Compound (XIV) may be prepared from Compound (XIII) by quinazoline ring construction reaction with a suitable reagents like formamide or similars.

Scheme 2a

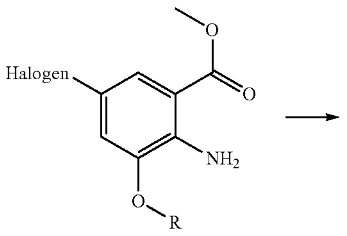
(XI)

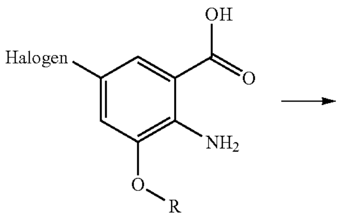
(XIIa)

-continued

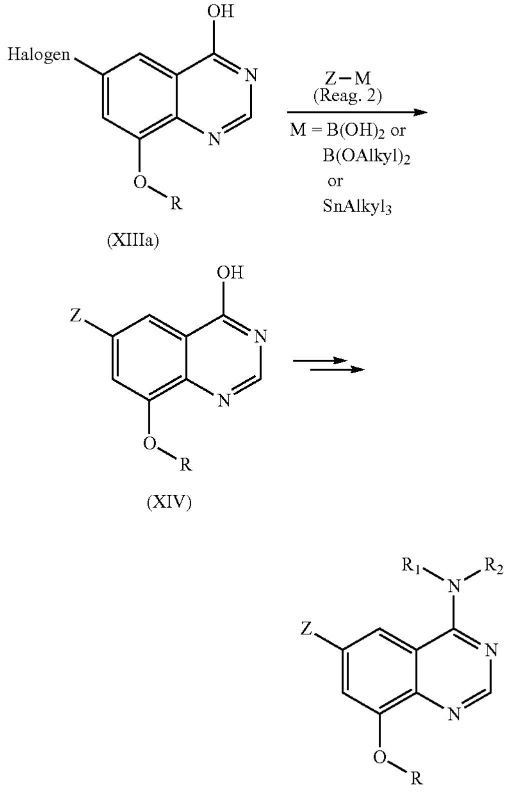

(XIIIa)

(XIV)

(Ia)

In another embodiment of the present invention, compound (Ia) may also be prepared according to SCHEME 2a from compound (XI).

Compound (XIIa) may be prepared from Compound (XI) by ester hydrolysis mediated by a suitable base like, for example, lithium hydroxide (LiOH).

Compound (XIIIa) may be prepared from Compound (XIIa) by quinazoline ring construction reaction with a suitable reagents like formamide or similars.

Compound (XIV) may be prepared from Compound (XIIIa) by metal-catalyzed cross coupling reactions like Stille, Suzuki or similar ones with a suitable organometallic reagents (Reag. 2) like, for example, organoboron compounds.

Compound (Ia) may be prepared from Compound (XIV) as already described in SCHEME 2.

Scheme 3

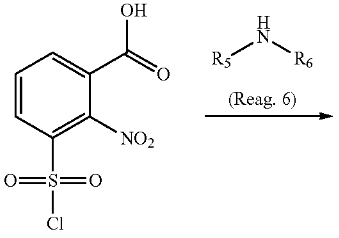

(XVI)

-continued

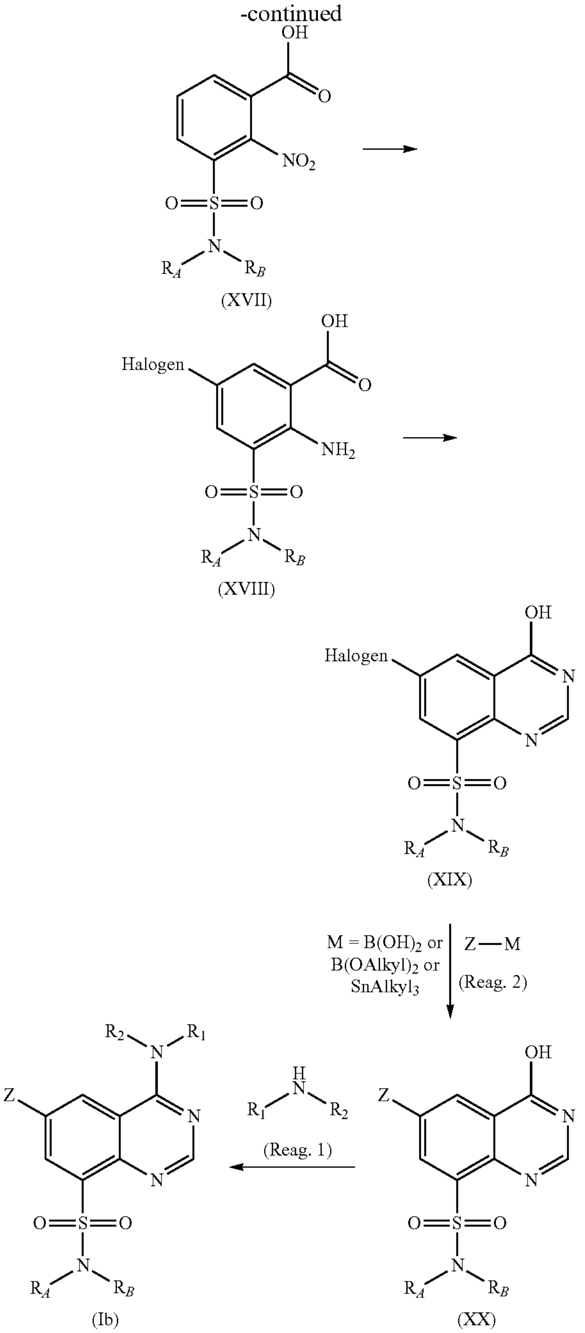

(XVII)

(XVIII)

(XIX)

(Ib)

(XX)

In another embodiment of the present invention, compound (Ib) may be prepared according to SCHEME 3 from compounds (XVI).

Compound (XVII) may be prepared from Compound (XVI) by amination reaction in the presence of a suitable amine (Reag. 6).

Compound (XVIII) may be prepared from Compound (XVII) by Halogention with suitable reagents like Bromine, NBS, NIS, Iodine, iodonium salts or similar Compound (XIX) may be prepared from Compound (XVIII) by quinazoline ring construction reaction with a suitable reagent like formamide or similar.

Compound (XX) may be prepared from Compound (XIX) by metal-catalyzed cross coupling reactions like Stille, Suzuki or similar ones with a suitable organometallic reagents (Reag. 2) like, for example, organoboron compounds.

Compound (Ib) may be prepared from Compound (XX) by amination reaction in the presence of a suitable amine (Reag. 1).

Some compounds (Ib) may contain a protected hydroxyl or amino group which were then removed under well known procedures.

Alternatively Compound (XXIIa) may be then prepared from Compound (XII) (XXII) by oxidation reaction with reagents like, for example, mCPBA.

Compound (Id) may be prepared from Compound (XXIIa) by a deoxyamination reaction mediated by coupling reagents like PyBOP with a suitable amine (Reag.1).

Compound (Id) may be prepared from Compound (XXIIa) by a deoxyamination reaction mediated by coupling reagents like PyBOP with a suitable amine (Reag.1).

Scheme 4

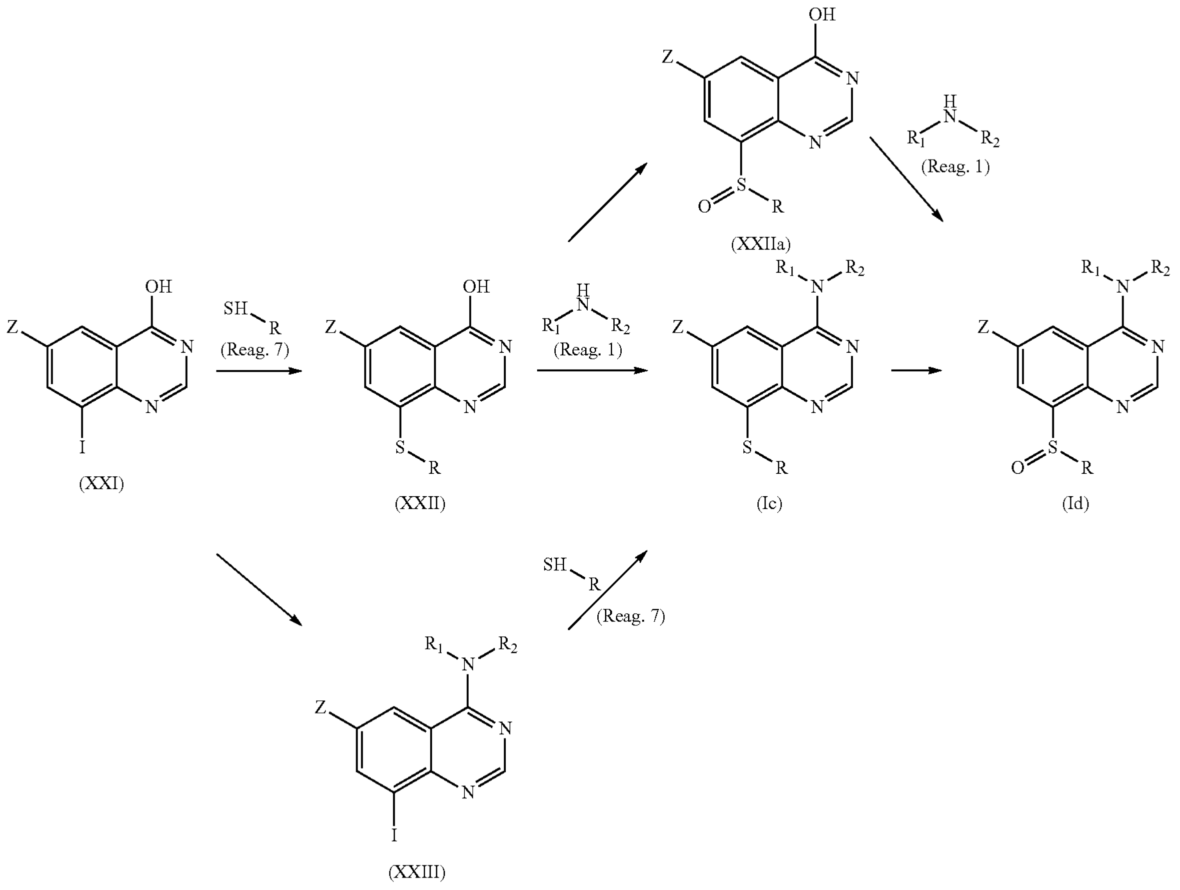

In another embodiment of the present invention, compound (Ic) and (Id) may be prepared according to SCHEME 4 from compounds (XXI).

Compound (XXII) may be prepared from Compound (XXI) by metal-catalyzed thiolation with suitable organosulfur reagents (Reag. 7).

Compound (Ic) may be prepared from Compound (XXII) by a deoxyamination reaction mediated by coupling reagents like PyBOP with a suitable amine (Reag.1).

Alternatively Compound (XXIII) may be prepared from Compound (XXI) by a deoxyamination reaction mediated by coupling reagents like PyBOP with a suitable amine (Reag.1).

Compound (Ic) may be prepared from Compound (XXIII) by metal-catalyzed thiolation with suitable organosulfur reagents (Reag. 7).

Compound (Id) may be prepared from Compound (Ic) by oxidation reaction with reagents like, for example, mCPBA.

Some compounds (Ic) may contain a protected hydroxyl or amino group which were then removed under well known procedures.

The compounds of the present invention have surprisingly been found to effectively inhibit $P2X_3$ receptor and said compounds are useful for the treatment of respiratory disease.

In one embodiment, representative compounds of formula (I) of the present invention have surprisingly been found to effectively and selectively inhibit $P2X_3$ receptor and said compounds are useful for the treatment of respiratory disease avoiding adverse effect, such as loss of taste response.

In a preferred embodiment, the compounds of formula (I) are selective $P2X_3$ antagonist wherein the selective $P2X_3$ antagonist is at least 10-fold selective for $P2X_3$ homomeric receptor antagonism versus $P2X_{2/3}$ heteromeric receptor antagonism.

In a further preferred embodiment, the selective $P2X_3$ antagonist is at least 30-fold selective for $P2X_3$ homomeric receptor antagonism versus $P2X_{2/3}$ heteromeric receptor antagonism.

In a further preferred embodiment, the selective $P2X_3$ antagonist is at least 50-fold selective for $P2X_3$ homomeric receptor antagonism versus $P2X_{2/3}$ heteromeric receptor antagonism.

The present invention also provides a pharmaceutical composition comprising a compound of formula (I) or a pharmaceutically acceptable salt thereof in admixture with one or more pharmaceutically acceptable carrier or excipient, either alone or in combination with one or more further active ingredient.

In one aspect, the invention refers to a compound of formula (I) according to the invention for use as a medicament.

In a further aspect, the invention refers to the use of a compound of formula (I) of the invention, or a pharmaceutically acceptable salt thereof, in the manufacture of a medicament for the treatment of disorders associated with $P2X_3$ receptors mechanism, preferably for the treatment of respiratory diseases.

Preferably, the invention refers to a compound of formula (I) for use in the prevention and/or treatment of respiratory diseases, preferably cough, sub-acute or chronic cough, treatment-resistant cough, idiopathic chronic cough, post-viral cough, iatrogenic cough, asthma, idiopathic pulmonary fibrosis (IPF), chronic obstructive pulmonary disease (COPD) and cough associated with respiratory diseases such as COPD, asthma and bronchospasm.

More preferably, the invention refers to a compound of formula (I) for use in the prevention and/or treatment of chronic cough and cough associated with respiratory diseases such as COPD, asthma and bronchospasm.

The invention also provides a method for the prevention and/or treatment of disorders associated with $P2X_3$ receptors mechanisms, said method comprising administering to a patient in need of such treatment a therapeutically effective amount of a compound of the invention.

In particular the invention refers to a method for the prevention and/or treatment wherein the disorder is cough, sub-acute or chronic cough, treatment-resistant cough, idiopathic chronic cough, post-viral cough, iatrogenic cough, asthma, idiopathic pulmonary fibrosis (IPF), chronic obstructive pulmonary disease (COPD) and cough associated with respiratory diseases such as COPD, asthma and bronchospasm, wherein said method comprises the administration of a proper amount of a compound of formula (I) to a patient in the need thereof.

In a further preferred embodiment, the disorder is chronic cough.

The methods of treatment of the invention comprise administering a safe and effective amount of a compound of formula (I) or a pharmaceutically acceptable salt thereof to a patient in need thereof. As used herein, “safe and effective amount” in reference to a compound of formula (I) or a pharmaceutically acceptable salt thereof or other pharmaceutically-active agent means an amount of the compound sufficient to treat the patient’s condition but low enough to avoid serious side effects and it can nevertheless be routinely determined by the skilled artisan. The compounds of formula (I) or pharmaceutically acceptable salts thereof may be administered once or according to a dosing regimen wherein a number of doses are administered at varying intervals of time for a given period of time. Typical daily dosages may vary depending upon the particular route of administration chosen.

The invention also provides pharmaceutical compositions of compounds of formula (I) in admixture with one or more pharmaceutically acceptable carrier or excipient, for example those described in Remington’s Pharmaceutical Sciences Handbook, XVII Ed., Mack Pub., N.Y., U.S.A.

Administration of the compounds of the invention and their pharmaceutical compositions may be accomplished according to patient needs, for example, orally, nasally, parenterally (subcutaneously, intravenously, intramuscularly, intrasternally and by infusion) and by inhalation.

Preferably the compounds of the present invention may be administered orally or by inhalation. More preferably the compounds of the present invention are administered orally.

Various solid oral dosage forms can be used for administering compounds of the invention including such solid forms as tablets, gelcaps, capsules, caplets, granules, lozenges and bulk powders. The compounds of the invention can be administered alone or combined with various pharmaceutically acceptable carriers, diluents (such as sucrose, mannitol, lactose, starches) and known excipients, including suspending agents, solubilizers, buffering agents, binders, disintegrants, preservatives, colorants, flavorants, lubricants and the like. Time release capsules, tablets and gels are also advantageous in administering the compounds of the invention.

Preferably the compounds of the invention are administered in forms of tablets.

Various liquid oral dosage forms can also be used for administering compounds of the invention, including aqueous and non-aqueous solutions, emulsions, suspensions, syrups, and elixirs. Such dosage forms can also contain suitable known inert diluents such as water and suitable known excipients such as preservatives, wetting agents, sweeteners, flavorants, as well as agents for emulsifying and/or suspending the compounds of the invention. The compounds of the invention may be injected, for example, intravenously, in the form of an isotonic sterile solution.

For the treatment of the diseases of the respiratory tract, the compounds according to the invention are preferably administered by inhalation.

Inhalable preparations include inhalable powders, propellant-containing metering aerosols or propellant-free inhalable formulations.

For administration as a dry powder, single- or multi-dose inhalers known from the prior art may be utilized. In that case the powder may be filled in gelatine, plastic or other capsules, cartridges or blister packs or in a reservoir.

A diluent or carrier chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic or hydroalcoholic medium and they may be delivered by jet or ultrasonic nebulizers known from the prior art or by soft-mist nebulizers.

Preferably, the compound of the present invention is administered orally.

The compounds of the invention can be administered as the sole active agent or in combination with other pharmaceutical active ingredients.

Preferably, the compound of the present invention can be combined with therapeutic agents or active ingredients useful for the treatment of disease which are related to or mediated by $P2X_3$ receptor.

The dosages of the compounds of the invention depend upon a variety of factors including among others the particular disease to be treated, the severity of the symptoms, the route of administration, and the like.

The invention is also directed to a device comprising a pharmaceutical composition comprising a compound of formula (I) according to the invention, in form of a single- or multi-dose dry powder inhaler or a metered dose inhaler.

The various aspects of the invention described in this application are illustrated buy the following examples which are not meant to limit the invention in any way. following examples illustrate the invention.

The example testing experiments described herein serve to illustrate the present invention and the invention is not limited to the examples given.

Preparations of Intermediates and Examples

Chemical names were generated using the Dotmatics software. In some cases generally accepted names of commercially available reagents were used in place of Dotmatics software generated names.

All reagents, for which the synthesis is not described in the experimental part, are either commercially available, or are known compounds or may be formed from known compounds by known methods by a person skilled in the art.

(R)-1-(2-(trifluoromethyl)pyrimidin-5-yl)ethanamine HCl, (R)-1-(6-methylpyridazin-3-yl)ethan-1-amine HCl were prepared accordingly to the procedure described in WO2016/091776.

Abbreviation—Meaning $Et_2O$: diethyl ether;
$Et_3N$: triethyl amine;
TEA: triethyl amine;
DCC: N,N'-Dicyclohexylcarbodiimide;
PyBOP: (benzotriazol-1-yloxy)tripyrrolidinophosphonium hexafluorophosphate;
DMF: dimethylformamide;
EtOAc: Ethyl acetate;
RT: room temperature;
THF: tetrahydrofuran;
DCM: dichloromethane;
MeOH: methyl alcohol;
EtOH: ethylic alcohol;
TFA: Trifluoroacetic acid;
LC-MS: Liquid Chromatography/Mass Spectrometry;
HPLC: high pressure liquid chromatography;
MPLC: medium pressure liquid chromatography;
SFC: Supercritical Fluid Chromatography;
dppf: 1,1'-Bis(diphenylphosphino) ferrocene;
DIEA or DIPEA: N,N-Diisopropylethylamine;
MeCN: Acetonitrile;
MTBE: tert-Butyl methyl ether;
TBDMSCl: tert-Butyl(chloro)dimethylsilane;
DMSO: Dimethylsulfoxide;
$Boc_2O$: di-tert-butyl dicarbonate;
UPLC: Ultra Performance Liquid Chromatography.
mCPBA: m-Chloroperbenzoic acid

General Experimental Details and Methods

Analytical Methods

Liquid Chromatography-Mass Spectrometry

Method 1

UPLC-MS was performed on a Waters Acquity I-Class with Waters Diode Array Detector coupled to a Waters SQD2 single quadrapole mass spectrometer using an Waters HSS C18 column (1.8 μm, 100×2.1 mm) being initially held at 5% acetonitrile/water (with 0.1% formic acid in each mobile phase) for 1.2 minutes, followed by a linear gradient of 5-100% within 3.5 minutes and then held at 100% for 1.5 minutes (F=0.5 mL/min).

Method 2

UPLC-MS was performed on a Waters Acquity I-Class with Waters Diode Array Detector coupled to a Waters SQD2 single quadrapole mass spectrometer using an Waters BEH Shield RP18 column (1.7 μm, 100×2.1 mm) being initially held at 5% acetonitrile/water (with 10 mM ammonium bicarbonate in each mobile phase) for 1.2 minutes, followed by a linear gradient of 5-100% within 3.5 minutes and then held at 100% for 1.5 minutes (F=0.5 mL/min).

Method 3

UPLC-MS was performed on a Waters DAD+Waters SQD2, single quadrapole UPLC-MS spectrometer using an Acquity UPLC BEH Shield RP18 1.7 um 100×2.1 mm (Plus guard cartridge), maintained at temp column being initially held at 5% acetonitrile/water (with 10 mM ammonium bicarbonate in each mobile phase) for 0.4 minutes, followed by a linear gradient of 5-95% within 6.4 minutes and then held at 95% for 1.2 minutes (F=0.4 mL/min).

Method 4

UPLC-MS was performed on a Waters DAD+Waters SQD2, single quadrapole UPLC-MS spectrometer using an Acquity UPLC BEH Shield RP18 1.7 um 100×2.1 mm (Plus guard cartridge), maintained at temp column being initially held at 5% Acetonitrile (Far UV grade) with 0.1% (V/V) formic acid/Water (High purity via PureLab Option unit) with 0.1% formic acid for 0.4 minutes, followed by a linear gradient of 5-95% within 6.4 minutes and then held at 95% for 1.2 minutes (F=0.4 mL/min).

Method 5

Aquity UPLC—QDa Mass Spectrometer with a C18-reverse-phase column (50×2.1 mm Acquity CSH with 1.7 μm particle size) maintained at 40° C., elution with A: 95/5 water/acetonitrile+0.05% formic acid; B: 95/5 acetonitrile/water+0.05% formic acid.

Gradient:

| Gradient - Time | flow (mL/min) | % A | % B |
|---|---|---|---|
| 0.00 | 1 | 99.0 | 1.0 |
| 1.50 | 1 | 0.1 | 99.9 |
| 1.90 | 1 | 0.1 | 99.9 |
| 2.00 | 1 | 99.0 | 1.0 |

Detection-MS. UV PDA

MS Ionisation Method-Electrospray (Positive/Negative Ion).

Method 5A

Aquity UPLC—QDa Mass Spectrometer with a C18-reverse-phase column (50×2.1 mm Acquity CSH with 1.7

μm particle size) maintained at 40° C., elution with A: 95/5 water/acetonitrile+0.05% formic acid; B: 95/5 acetonitrile/water+0.05% formic acid.

Gradient:

| Gradient - Time | flow (mL/min) | % A | % B |
|---|---|---|---|
| 0.00 | 1 | 99.0 | 1.0 |
| 3.50 | 1 | 0.1 | 99.9 |
| 3.90 | 1 | 0.1 | 99.9 |
| 4.00 | 1 | 99.0 | 1.0 |

Detection-MS, UV PDA

MS Ionisation Method-Electrospray (Positive/Negative Ion).

Method 6

Aquity UPLC—QDa Mass Spectrometer with a C18-reverse-phase column (50×2.1 mm Acquity BEH with 1.7 μm particle size) maintained at 40° C., elution with A: 95/5 water/acetonitrile+0.05% conc. ammonia; B: 95/5 acetonitrile/water+0.05% conc. ammonia.

Gradient:

| Gradient - Time | flow (mL/min) | % A | % B |
|---|---|---|---|
| 0.00 | 1 | 99.0 | 1.0 |
| 1.50 | 1 | 0.1 | 99.9 |
| 1.90 | 1 | 0.1 | 99.9 |
| 2.00 | 1 | 99.0 | 1.0 |

Detection-MS, UV PDA

MS Ionisation Method-Electrospray (Positive/Negative Ion)

Method 7

Dionex UHPLC Ultimate 3000 with DAD detector/Thermo Scientific MSQ Pluse quipped with a Kinetex® 2.6 μm XB-C18 (4.6×50 mm), 110A maintained at 25° C., elution with A: 0.1% v/v water solution of formic acid, B: 0.1% v/v acetonitrile solution of formic acid Gradient:

| Time [min] | Flow [ml/min] | Mobile phase A [%] | Mobile phase B [%] |
|---|---|---|---|
| 0.0 | 1.0 | 95 | 5 |
| 1.0 | 1.0 | 95 | 5 |
| 4.75 | 1.0 | 20 | 80 |
| 5.25 | 1.0 | 20 | 80 |
| 6.0 | 1.0 | 95 | 5 |
| 7.0 | 1.0 | 95 | 5 |

Detection-MS, UV PDA

MS Ionisation Method-Electrospray (Positive/Negative Ion)

NMR $^1$H Nuclear magnetic resonance (NMR) spectroscopy was carried out using a Bruker or Varian instruments operating at 300 or 400 MHz using the stated solvent at around room temperature unless otherwise stated. In all cases, NMR data were consistent with the proposed structures. Characteristic chemical shifts (8) are given in parts-per-million using conventional abbreviations for designation of major peaks: e.g. s, singlet; d, doublet; t, triplet; q, quartet; dd, doublet of doublets; dt, doublet of triplets; m, multiplet; br, broad.

Preparative Reverse-Phase HPLC Conditions

Preparative HPLC purification was performed by reverse phase HPLC using a Waters Fractionlynx preparative HPLC system (2525 pump, 2996/2998 UV/VIS detector, 2767 liquid handler) or an equivalent HPLC system such as a Gilson Trilution UV directed system. The Waters 2767 liquid handler acted as both auto-sampler and fraction collector. The columns used for the preparative purification of the compounds were a Waters Sunfire OBD Phenomenex Luna Phenyl Hexyl or Waters Xbridge Phenyl at 10 μm 19×150 mm or Waters CSH Phenyl Hexyl, 19×150, 5 μm column. Appropriate focused gradients were selected based on acetonitrile and methanol solvent systems under either acidic or basic conditions. The modifiers used under acidic/basic conditions were formic acid or trifluoroacetic acid (0.1% V/V) and ammonium bicarbonate (10 mM) respectively. The purification was controlled by Waters Fractionlynx software through monitoring at 210-400 nm and triggered a threshold collection value at 260 nm and, when using the Fractionlynx, the presence of target molecular ion as observed under API conditions. Collected fractions were analysed by LCMS (Waters Acquity systems with Waters SQD).

Chiral Supercritical Fluid Chromatography (SFC) Separation Protocol

The diastereomeric separation of compounds was achieved by Supercritical Fluid Chromatography (SFC) using a Waters Thar Prep100 preparative SFC system (P200 CO2 pump, 2545 modifier pump, 2998 UV/VIS detector, 2767 liquid handler with Stacked Injection Module). The Waters 2767 liquid handler acted as both auto-sampler and fraction collector. Appropriate isocratic methods were selected based on methanol, ethanol or isopropanol solvent systems under un-modified or basic conditions. The standard SFC method used was modifier, CO2, 100 mL/min, 120 Bar backpressure, 40° C. column temperature. The modifier used under basic conditions was diethylamine (0.1% V/V). The modifier used under acidic conditions was either formic acid (0.1% V/V) or trifluoroacetic acid (0.1% V/V). The SFC purification was controlled by Waters Fractionlynx software through monitoring at 210-400 nm and triggered at a threshold collection value, typically 260 nm. Collected fractions were analysed by SFC (Waters/Thar SFC systems with Waters SQD). The fractions that contained the desired product were concentrated by vacuum centrifugation.

Supercritical Fluid Chromatography—Mass Spectrometry Analytical Conditions

Method 8

SFC-MS was performed on a Waters/Thar SFC systems with Waters SQD using a Lux Cellulose-3 column with a 15% methyl alcohol/$CO_2$ (with 0.1% diethylamine) isocratic run at 5 mL/min, 120 Bar backpressure, 40° C. column temperature.

Method 9

SFC-MS was performed on a Waters/Thar SFC systems with Waters SQD using a Lux Cellulose-3 column with a 20% methyl alcohol/$CO_2$ (with 0.1% diethylamine) isocratic run at 5 mL/min, 120 Bar backpressure, 40° C. column temperature.

Method 10

SFC-MS was performed on a Waters/Thar SFC systems with Waters SQD using a Lux Cellulose-4 column with a 55% ethyl alcohol/$CO_2$ (with 0.1% diethylamine)isocratic run at 5 mL/min, 120 Bar backpressure, 40° C. column temperature.

Method 11

SFC-MS was performed on a Waters/Thar SFC systems with Waters SQD using a Lux Cellulose-4 column with a 20% iso-propyl alcohol/$CO_2$ (with 0.1% diethylamine) isocratic run at 5 mL/min, 120 Bar backpressure, 40° C. column temperature.

Method 12

SFC-MS was performed on a Waters/Thar SFC systems with Waters SQD using a Lux Cellulose-4 column with a 30% iso-propyl alcohol/$CO_2$ (with 0.1% diethylamine) isocratic run at 5 mL/min, 120 Bar backpressure, 40° C. column temperature.

Method 13

SFC-MS was performed on a Waters/Thar SFC systems with Waters SQD using a Lux Cellulose-4 column with a 50% iso-propyl alcohol/$CO_2$ (with 0.1% diethylamine) isocratic run at 5 mL/min, 120 Bar backpressure, 40° C. column temperature.

Method 14

SFC-MS was performed on a Waters/Thar SFC systems with Waters SQD using a Lux Cellulose-4 column with a 25% methyl alcohol/$CO_2$ (with 0.1% diethylamine) isocratic run at 5 mL/min, 120 Bar backpressure, 40° C. column temperature.

Method 15

SFC-MS was performed on a Waters/Thar SFC systems with Waters SQD using a YMC Amylose-C column with a 15% ethyl alcohol/$CO_2$ (with 0.1% diethylamine) isocratic run at 5 mL/min, 120 Bar backpressure, 40° C. column temperature.

Method 16

SFC-MS was performed on a Waters/Thar SFC systems with Waters SQD using a YMC Amylose-C column with a 25% iso-propyl alcohol/$CO_2$ (with 0.1% diethylamine) isocratic run at 5 mL/min, 120 Bar backpressure, 40° C. column temperature.

Method 17

SFC-MS was performed on a Waters/Thar SFC systems with Waters SQD using a YMC Amylose-C column with a 35% iso-propyl alcohol/$CO_2$ (with 0.1% diethylamine) isocratic run at 5 mL/min, 120 Bar backpressure, 40° C. column temperature.

Method 18

SFC-MS was performed on a Waters/Thar SFC systems with Waters SQD using a YMC Amylose-C column with a 55% iso-propyl alcohol/$CO_2$ (with 0.1% diethylamine) isocratic run at 5 mL/min, 120 Bar backpressure, 40° C. column temperature.

Method 19

SFC-MS was performed on a Waters/Thar SFC systems with Waters SQD using a YMC Amylose-C column with a 15% methyl alcohol/$CO_2$ (with 0.1% diethylamine) isocratic run at 5 mL/min, 120 Bar backpressure, 40° C. column temperature.

Method 20

SFC-MS was performed on a Waters/Thar SFC systems with Waters SQD using a YMC Amylose-C column with a 20% methyl alcohol/$CO_2$ (with 0.1% diethylamine) isocratic run at 5 mL/min, 120 Bar backpressure, 40° C. column temperature.

Method 21

SFC-MS was performed on a Waters/Thar SFC systems with Waters SQD using a YMC Cellulose-C column with a 15% iso-propyl alcohol/$CO_2$ (with 0.1% diethylamine) isocratic run at 5 mL/min, 120 Bar backpressure, 40° C. column temperature.

Method 22

SFC-MS was performed on a Waters/Thar SFC systems with Waters SQD using a YMC Cellulose-C column with a 15% methyl alcohol/$CO_2$ (with 0.1% diethylamine) isocratic run at 5 mL/min, 120 Bar backpressure, 40° C. column temperature.

Method 23

SFC-MS was performed on a Waters/Thar SFC systems with Waters SQD using a YMC Cellulose-C column with a 25% methyl alcohol/$CO_2$ (with 0.1% diethylamine) isocratic run at 5 mL/min, 120 Bar backpressure, 40° C. column temperature.

Method 24

SFC-MS was performed on a Waters/Thar SFC systems with Waters SQD using a YMC Cellulose-SC column with a 55% iso-propyl alcohol/$CO_2$ (with 0.1% diethylamine) isocratic run at 5 mL/min, 120 Bar backpressure, 40° C. column temperature.

Method 25

SFC-MS was performed on a Waters/Thar SFC systems with Waters SQD using a Lux Cellulose-3 column with a 10% methyl alcohol/$CO_2$ (with 0.1% diethylamine) isocratic run at 5 mL/min, 120 Bar backpressure, 40° C. column temperature.

Method 26

SFC-MS was performed on a Waters/Thar SFC systems with Waters SQD using a Lux Cellulose-3 column with a 25% methyl alcohol/$CO_2$ (with 0.1% diethylamine) isocratic run at 5 mL/min, 120 Bar backpressure, 40° C. column temperature.

Method 27

SFC-MS was performed on a Waters/Thar SFC systems with Waters SQD using a Lux Cellulose-3 column with a 30% methyl alcohol/$CO_2$ (with 0.1% diethylamine) isocratic run at 5 mL/min, 120 Bar backpressure, 40° C. column temperature.

Method 28

SFC-MS was performed on a Waters/Thar SFC systems with Waters SQD using a Lux Cellulose-4 column with a 40% iso-propyl alcohol/$CO_2$ (with 0.1% diethylamine) isocratic run at 5 mL/min, 120 Bar backpressure, 40° C. column temperature.

Method 29

SFC-MS was performed on a Waters/Thar SFC systems with Waters SQD using a Lux Cellulose-4 column with a 40% methyl alcohol/$CO_2$ (with 0.1% diethylamine) isocratic run at 5 mL/min, 120 Bar backpressure, 40° C. column temperature.

Method 30

SFC-MS was performed on a Waters/Thar SFC systems with Waters SQD using a Lux Cellulose-4 column with a 50% methyl alcohol/$CO_2$ (with 0.1% diethylamine) isocratic run at 5 mL/min, 120 Bar backpressure, 40° C. column temperature.

Method 31

SFC-MS was performed on a Waters/Thar SFC systems with Waters SQD using a Lux Cellulose-4 column with a 55% iso-propyl alcohol/$CO_2$ (with 0.1% diethylamine) isocratic run at 5 mL/min, 120 Bar backpressure, 40° C. column temperature.

Method 32

SFC-MS was performed on a Waters/Thar SFC systems with Waters SQD using a Lux Cellulose-4 column with a 55% methyl alcohol/$CO_2$ (with 0.1% diethylamine) isocratic run at 5 mL/min, 120 Bar backpressure, 40° C. column temperature.

Method 33

SFC-MS was performed on a Waters/Thar SFC systems with Waters SQD using a YMC Amylose-C column with a 20% ethyl alcohol/$CO_2$ (with 0.1% diethylamine) isocratic run at 5 mL/min, 120 Bar backpressure, 40° C. column temperature.

Method 34

SFC-MS was performed on a Waters/Thar SFC systems with Waters SQD using a YMC Amylose-C column with a 30% iso-propyl alcohol/$CO_2$ (with 0.1% diethylamine) isocratic run at 5 mL/min, 120 Bar backpressure, 40° C. column temperature.

Method 35

SFC-MS was performed on a Waters/Thar SFC systems with Waters SQD using a YMC Amylose-C column with a 30% methyl alcohol/$CO_2$ (with 0.1% diethylamine) isocratic run at 5 mL/min, 120 Bar backpressure, 40° C. column temperature.

Method 36

SFC-MS was performed on a Waters/Thar SFC systems with Waters SQD using a YMC Amylose-C column with a 40% methyl alcohol/$CO_2$ (with 0.1% diethylamine) isocratic run at 5 mL/min, 120 Bar backpressure, 40° C. column temperature.

Method 37

SFC-MS was performed on a Waters/Thar SFC systems with Waters SQD using a YMC Amylose-C column with a 55% methyl alcohol/$CO_2$ (with 0.1% diethylamine) isocratic run at 5 mL/min, 120 Bar backpressure, 40° C. column temperature.

Method 38

SFC-MS was performed on a Waters/Thar SFC systems with Waters SQD using a YMC Cellulose-C column with a 20% methyl alcohol/$CO_2$ (with 0.1% diethylamine) isocratic run at 5 mL/min, 120 Bar backpressure, 40° C. column temperature.

Method 39

SFC-MS was performed on a Waters/Thar SFC systems with Waters SQD using a YMC Cellulose-SC column with a 35% iso-propyl alcohol/$CO_2$ (with 0.1% diethylamine) isocratic run at 5 mL/min, 120 Bar backpressure, 40° C. column temperature.

Method 40

SFC-MS was performed on a Waters/Thar SFC systems with Waters SQD using a YMC Cellulose-SC column with a 45% iso-propyl alcohol/$CO_2$ (with 0.1% diethylamine) isocratic run at 5 mL/min, 120 Bar backpressure, 40° C. column temperature.

Intermediate 1

2-Amino-5-bromo-3-methoxybenzoic acid hydrobromide

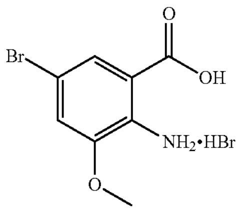

A solution of bromine (6.0 g, 1.9 mL, 37.70 mmol) in chloroform (15 mL) was added dropwise over a period of one hour to a suspension of 2-amino-3-methoxybenzoic acid (6.0 g, 35.90 mmol) in chloroform (180 mL) at 0° C. The reaction was stirred for a further five hours and slowly allowed to warm to room temperature. The solvent was removed in vacuo and the residue was triturated with diethyl ether. The reaction was filtered to give the title compound as a beige solid (11.3 g, 96%).

LCMS (Method 4): [MH+]=247 at 4.07 min.

Intermediate 2

6-Bromo-8-methoxyquinazolin-4-ol

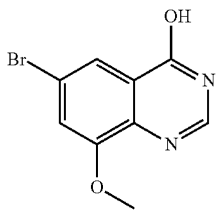

A solution 2-amino-5-bromo-3-methoxybenzoic acid hydrobromide (Intermediate 1) (10.0 g, 30.60 mmol) in formamide (40 mL) was heated to 165° C. for 18 hours. After return to room temperature, the reaction was diluted with water (100 mL) and poured into ice water (400 mL) and filtered. The solid was washed with water (200 mL) and diethyl ether (200 mL) to give the title compound as a light brown solid (5.9 g, 76%).

LCMS (Method 4): [MH+]=255 at 3.07 min.

Intermediate 3

6-(4-Fluorophenyl)-8-methoxyquinazolin-4-ol

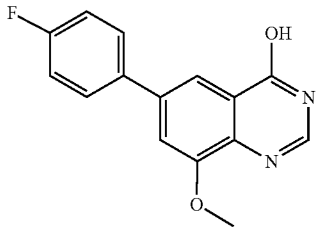 [SMILES: COc1cc(-c2ccc(F)cc2)cc2c(O)ncnc12]

Nitrogen was bubbled for 5 min through a mixture of 6-bromo-8-methoxyquinazolin-4-ol (Intermediate 2) (1.18 g, 4.63 mmol), 4-fluorophenylboronic acid (710 mg, 5.09 mmol) and cesium carbonate (5.73 g, 17.58 mmol) in 1,4-dioxane (30 mL) and water (7.5 mL), then [1,1'-bis (diphenylphosphino)ferrocene]dichloropalladium(II) complex with dichloromethane (190 mg, 0.23 mmol) was added and the reaction was heated to 110° C. for 5 hours. After return to room temperature, the reaction was diluted with water (20 mL), filtered and the solid was washed with 10% methanol in diethyl ether then with diethyl ether to give the title compound (1.0 g, 80%) as a beige solid.

LCMS (Method 5): [MH+]=271.1 at 0.81 min.

Intermediate 4

6-(4-Fluorophenyl)-8-methoxy-N-(1-(3-methyl-1,2,4-oxadiazol-5-yl)ethyl)quinazolin-4-amine

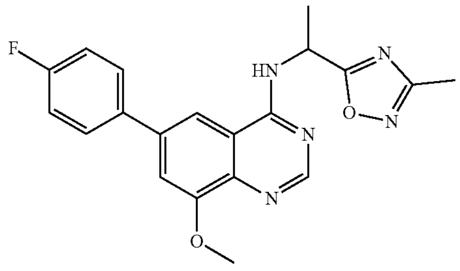 [SMILES: COc1cc(-c2ccc(F)cc2)cc2c(NC(C)c3nc(C)no3)ncnc12]

To a solution of 6-(4-fluorophenyl)-8-methoxyquinazolin-4-ol (Intermediate 3) (100 mg, 0.37 mmol) in N,N-dimethylformamide (2 mL) was successively added (benzotriazol-1-yloxy)tripyrrolidinophosphonium hexafluorophosphate (212 mg, 0.41 mmol) and di-isopropylethylamine (0.32 mL, 1.85 mmol). The resulting mixture was heated to 40° C. and stirred for 20 min, 1-(3-methyl-1,2,4-oxadiazol-5-yl)ethan-1-amine (67 mg, 0.41 mmol) was then added and the heating was maintained at 40° C. for 18 hours. After return to room temperature, the mixture was diluted with ethyl acetate (50 mL) and water (20 mL). The organic phase was washed with brine (2×20 mL), passed through a hydrophobic frit and the solvent was removed in vacuo. The residue was purified by preparative HPLC to give the title compound (43 mg, 31%) as a white solid.

$^1$H NMR (400 MHz, DMSO): δ 8.85 (d, J=6.8 Hz, 1H), 8.49 (s, 1H), 8.24 (s, 1H), 7.99 (dd, J=5.6, 8.6 Hz, 2H), 7.61 (s, 1H), 7.44 (dd, J=8.8, 8.8 Hz, 2H), 5.88-5.82 (m, 1H), 4.08 (s, 3H), 2.37 (s, 3H), 1.78 (d, J=7.1 Hz, 3H). LCMS (Method 4): [MH+]=375 at 3.29 min.

The compounds reported in the table below were synthesised following the same procedure described for the preparation of 6-(4-Fluorophenyl)-8-methoxy-N-(1-(3-methyl-1,2,4-oxadiazol-5-yl)ethyl)quinazolin-4-amine (Intermediate 4).

Intermediate 6

(R)-6-Bromo-8-methoxy-N-(1-(6-methylpyridazin-3-yl)ethyl)quinazolin-4-amine

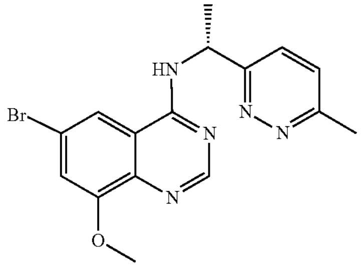 [SMILES: COc1cc(Br)cc2c(N[C@H](C)c3ccc(C)nn3)ncnc12]

To a solution of 6-bromo-8-methoxyquinazolin-4-ol (Intermediate 2) (65 mg, 0.27 mmol) in N,N-dimethylformamide (1.5 mL) was successively added (benzotriazol-1-yloxy)tripyrrolidinophosphonium hexafluorophosphate (139 mg, 0.27 mmol) and di-isopropylethylamine (0.2 mL, 0.81 mmol). The resulting mixture was heated to 60° C. for one hour then (R)-1-(6-methylpyridazin-3-yl)ethan-1-amine (65 mg, 0.27 mmol) was added and the heating was maintained at 60° C. for 18 hours. After return to room temperature, the reaction mixture was directly concentrated onto silica gel and purified by chromatography on silica gel eluting with 0-100% (10% MeOH in ethyl acetate) in ethyl acetate to give the title compound as a beige solid (100 mg, quantitative yield).

LCMS (Method 4): [MH+]=374 at 2.42 min.

The following intermediates reported in the table below were synthesised following the same procedure described for the preparation of (R)-6-Bromo-8-methoxy-N-(1-(6-methylpyridazin-3-yl)ethyl)quinazolin-4-amine (Intermediate 6):

| Intermediate No. | Chemical Name Structure | Analytical Data $^1$H NMR LC-MS |
|---|---|---|
| Intermediate 5 | 6-(4-Fluorophenyl)-8-methoxy-N-[(1-methyl-4-piperidyl)methyl]quinazolin-4-amine 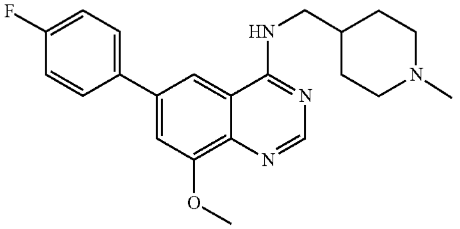 | $^1$H NMR (400 MHz, DMSO): δ 8.43 (s, 1 H), 8.34 (dd, J = 5.5, 5.5 Hz, 1 H), 8.10 (d, J = 1.6 Hz, 1 H), 7.94-7.89 (m, 2 H), 7.50 (d, J = 1.6 Hz, 1 H), 7.39 (dd, J = 8.8, 8.8 Hz, 2 H), 4.01 (s, 3 H), 3.46 (s, 2 H), 2.89 (d, J = 11.4 Hz, 2 H), 2.27 (s, 3 H), 2.09-2.03 (m, 2 H), 1.76 (dd, J = 10.2, 10.2 Hz, 3 H), 1.34-1.24 (m, 2 H). LCMS (Method 4): [MH+] = 381 at 2.27 min. |

| Intermediate No. | Chemical name Structure | Analytical data LC-MS |
|---|---|---|
| Intermediate 7 | 6-Bromo-8-methoxy-N-[(1R)-1-[2-(trifluoromethyl)pyrimidin-5-yl]ethyl]quinazolin-4 amine 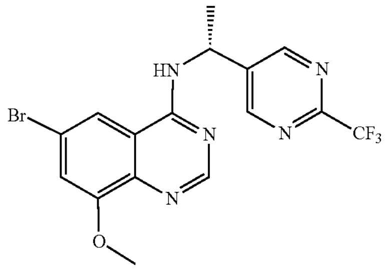 | LCMS (Method 4): [MH+] = 428 at 3.19 min |
| Intermediate 8 | 6-Bromo-8-methoxy-N-((6-methylpyridazin-3-yl)methyl)quinazolin-4-amine 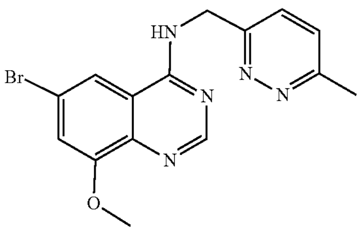 | LCMS (Method 3): [MH+] = 360 at 3.06 min. |

Intermediate 9

6-(4-Fluoro-2-methoxyphenyl)-8-methoxy-N-((6-methylpyridazin-3-yl)methyl)quinazolin-4-amine

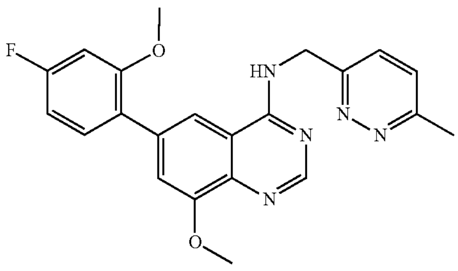 [SMILES: COc1cc(F)ccc1-c1cc(OC)c2ncnc(NCc3ccc(C)nn3)c2c1]

To a solution of 6-bromo-8-methoxy-N-((6-methylpyridazin-3-yl)methyl)quinazolin-4-amine (intermediate 8) (70 mg, 0.19 mmol) in 1,2-dimethoxyethane (3.0 mL) was added (4-fluoro-2-methoxyphenyl)boronic acid (41 mg, 0.24 mmol), [1,1'-bis(diphenylphosphino)ferrocene]dichloropalladium(II) complex with dichloromethane (8.2 mg, 0.01 mmol), caesium carbonate (130 mg, 0.40 mmol) and water (0.3 mL). The resulting mixture was heated to 95° C. for 18 h. After return to room temperature, the reaction was filtered through Celite®. The Celite® cake was rinsed with ethyl acetate (2×20 mL). Combined organic phases were washed with brine (2×20 mL), filtered through a hydrophobic frit and the solvent was removed in vacuo. The residue was purified by preparative HPLC to give the title compound as an off-white solid (35 mg, 45%).

$^1$H NMR (400 MHz, DMSO): δ 8.92 (dd, J=5.8, 5.8 Hz, 1H), 8.41 (s, 1H), 7.91 (d, J=1.5 Hz, 1H), 7.54-7.46 (m, 3H), 7.37 (d, J=1.4 Hz, 1H), 7.10 (dd, J=2.4, 11.5 Hz, 1H), 6.97-6.91 (m, 1H), 4.99 (d, J=5.6 Hz, 2H), 3.93 (s, 3H), 3.84 (s, 3H), 2.59 (s, 3H). LCMS (Method 3): [MH+]=406 at 3.97 min.

The following compounds reported in the table below were prepared via adaptation of the above procedure starting from appropriate intermediate reported in table.

| Intermediate No. | Chemical Name Structure | Analytical data $^1$H NMR LC-MS | Starting Intermediate |
|---|---|---|---|
| Intermediate 10 | (R)-6-(4-fluorophenyl)-8-methoxy-N-(1-(2-(trifluoromethyl)pyrimidin-5-yl)ethyl)quinazolin-4-amine 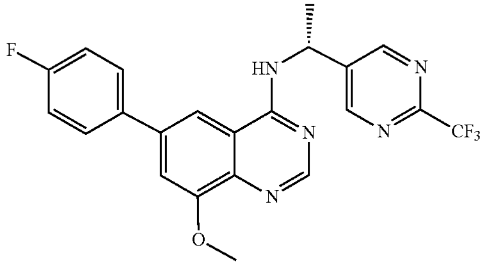 | LCMS (Method 5): 0.79 min, m/z 443.8 [M + 2]+, $^1$H NMR (400 MHz, DMSO-d6) δ ppm 9.12 (s, 2 H), 8.55 (d, J = 7.0 Hz, 1 H), 8.37 (s, 1 H), 8.14 (d, J = 1.3 Hz, 1 H), 7.83-7.96 (m, 2 H), 7.48 (d, J = 1.3 Hz, 1 H), 7.35 (t, J = 8.8 Hz, 2 H), 5.50-5.60 (m, 1 H), 3.97 (s, 3 H), 1.69 (d, J = 7.0 Hz, 3 H). | Intermediate 7 |
| Intermediate 11 | 6-(4-fluorophenyl)-8-methoxy-N-((6-methylpyridazin-3-yl)methyl)quinazolin-4-amine 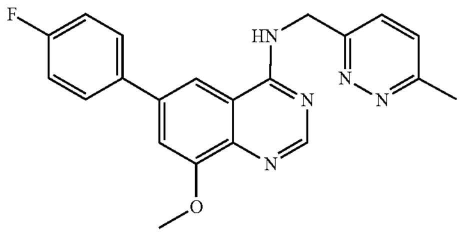 | LCMS (Method 6): 0.88 min, 375.9 m/z [M + H]+, $^1$H NMR (400 MHz, ACETONITRILE-d3) δ □ ppm 8.43 (s, 1 H), 7.66-7.84 (m, 3 H), 7.53 (d, J = 8.8 Hz, 1 H), 7.44 (d, J = 1.3 Hz, 1 H), 7.39 (d, J = 8.8 Hz, 1 H), 7.20-7.30 (m, 2 H), 7.00-7.15 (m, 1 H), 5.06 (s, 2 H), 4.04 (s, 3 H), 2.62 (s, 3 H). | Intermediate 8 |

Intermediate 12

6-(5,5-dimethyl-1,3,2-dioxaborinan-2-yl)-8-methoxy-N-((6-methylpyridazin-3-yl)methyl)quinazolin-4-amine

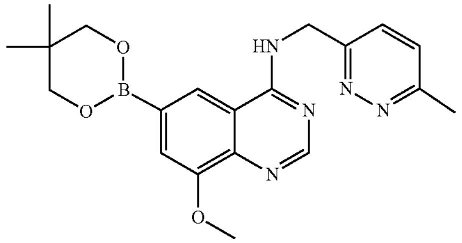

Nitrogen was bubbled for 5 min through a mixture of 6-bromo-8-methoxy-N-((6-methylpyridazin-3-yl)methyl) quinazolin-4-amine (Intermediate 8) (100 mg, 0.28 mmol), bis(neopentyl glycolato)diboron (66 mg, 0.29 mmol), [1,1'-bis(diphenylphosphino)ferrocene]-dichloropalladium (II) complex with dichloromethane (10 mg, 0.02 mmol) and potassium acetate (54 mg, 0.55 mmol) in 1,4-dioxane (3.0 mL). The mixture was heated to 100° C. for 3 hours. After return to room temperature, the mixture was taken on to the next step as a 1,4-dioxane solution without further purification.

Intermediate 13

Preparation of 8-methoxy-N-((6-methylpyridazin-3-yl)methyl)-6-(5-methylthiazol-2-yl)quinazolin-4-amine

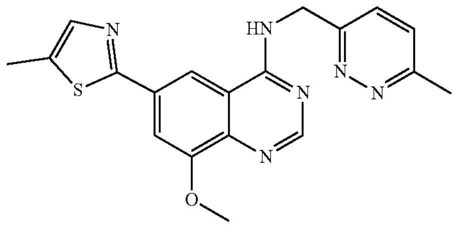

To the above solution of 6-(5,5-dimethyl-1,3,2-dioxaborinan-2-yl)-8-methoxy-N-((6-methylpyridazin-3-yl)methyl) quinazolin-4-amine (100 mg, 0.28 mmol) was added aqueous caesium carbonate (181 mg, 0.56 mmol, 0.4 mL), 2-bromo-5-methylthiazole (64 mg, 0.28 mmol) and tetrakis (triphenylphosphine)palladium(0) (20 mg, 0.02 mmol). The resulting mixture was heated to 95° C. for 16 hours. After return to room temperature, the mixture was filtered through Celite® and the filter cake rinsed with ethyl acetate (2×10 mL). The organic phases were washed with saturated aqueous ammonium chloride (10 mL), passed through a hydrophobic frit and the solvent was removed in vacuo. The residue was purified by preparative HPLC to give the title compound as an off-white solid (25 mg, 24%).

$^1$H NMR (400 MHz, DMSO): δ 9.24 (dd, J=5.7, 5.7 Hz, 1H), 8.43 (s, 1H), 8.37 (d, J=1.5 Hz, 1H), 7.75 (d, J=1.5 Hz, 1H), 7.68 (d, J=1.1 Hz, 1H), 7.57 (d, J=8.7 Hz, 1H), 7.50 (d, J=8.7 Hz, 1H), 5.02 (d, J=5.8 Hz, 2H), 4.00 (s, 3H), 2.60 (s, 3H), 2.50 (s, 3H). LCMS (Method 3): [MH+]=379 at 3.20 min.

The following compounds reported in the table below were prepared according to the same procedure described for the preparation of 8-methoxy-N-((6-methylpyridazin-3-yl)methyl)-6-(5-methylthiazol-2-yl)quinazolin-4-amine (Intermediate 13)

| Intermediate No. | Chemical Name Structure | Analytical data $^1$H NMR LC-MS | Starting Intermediate |
|---|---|---|---|
| Intermediate 14 | 8-Methoxy-N-[(1R)-1-(6-methylpyridazin-3-yl)ethyl]-6-(5-methylpyrimidin-2-yl)quinazolin-4-amine 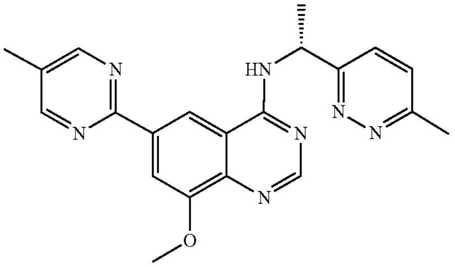 | $^1$H NMR (400 MHz, DMSO): δ 9.05 (d, J = 1.4 Hz, 1 H), 9.00 (d, J = 7.5 Hz, 1 H), 8.86 (s, 2 H), 8.40 (s, 1 H), 8.21 (d, J = 1.4 Hz, 1 H), 7.64 (d, J = 8.7 Hz, 1 H), 7.50 (d, J = 8.8 Hz, 1 H), 5.81-5.76 (m, 1 H), 4.01 (s, 3 H), 2.59 (s, 3 H), 2.39 (s, 3 H), 1.72 (d, J = 7.2 Hz, 3 H). LCMS (Method 3): [MH+] = 388 at 3.64 min. Chiral analysis (Method 37) at 1.56 min. | Intermediate 6 |

Intermediate 15

8-methoxy-N-((6-methylpyridazin-3-yl)methyl)-6-(4,4,5,5-tetramethyl-1,3,2-dioxaborolan-2-yl)quinazolin-4-amine

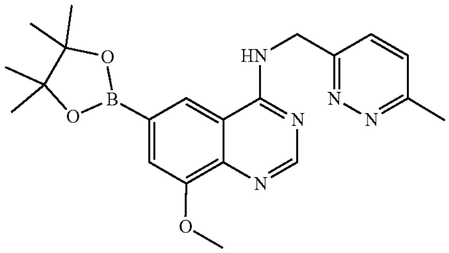

Nitrogen was bubbled for 5 min through a mixture of 6-bromo-8-methoxy-N-((6-methylpyridazin-3-yl)methyl) quinazolin-4-amine (Intermediate 8) (250 mg, 0.69 mmol), bis-(pinacolato)diboron (194 mg, 0.76 mmol), [1,1'-bis-(diphenylphosphino)-ferrocene]dichloropalladium(II)(25 mg, 0.03 mmol) and potassium acetate (204 mg, 2.08 mmol) in 1,4-dioxane (15.0 mL). The mixture was heated at 90° C. for 18 hours. After return to room temperature, the reaction was filtered through Celite® and the solvent was removed in vacuo. The residue was taken on to the next step without further purification.

Intermediate 16

8-methoxy-6-(5-methyl-1,3,4-thiadiazol-2-yl)-N-((6-methylpyridazin-3-yl)methyl)quinazolin-4-amine

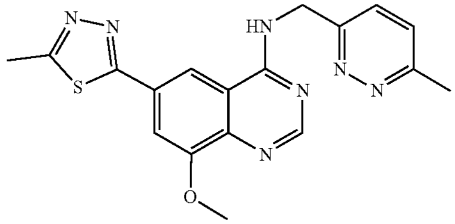

Nitrogen was bubbled for 5 min through a mixture of 2-bromo-5-methyl-1,3,4-thiadiazole (34 mg, 0.19 mmol), 8-methoxy-N-((6-methylpyridazin-3-yl)methyl)-6-(4,4,5,5-tetramethyl-1,3,2-dioxaborolan-2-yl)quinazolin-4-amine (70 mg, 0.17 mmol), potassium carbonate (36 mg, 0.26 mmol) and water (0.5 mL) in 1,4-dioxane (4.0 mL), then tetrakis(triphenylphosphine)palladium(0) (20 mg, 0.02 mmol) was added. The resulting mixture was heated to 95° C. for 16 hours. After return to room temperature, the reaction was filtered through Celite®, rinced with ethyl acetate (20 mL). The organic phases were combined, passed through a hydrophobic frit and the solvent was removed in vacuo. The residue was purified by preparative HPLC to give the title compound as an off-white solid (21.0 mg, 32%).

$^1$H NMR (400 MHz, DMSO): δ 9.31 (dd, J=5.8, 5.8 Hz, 1H), 8.47 (s, 1H), 8.44 (d, J=1.7 Hz, 1H), 7.80 (d, J=1.4 Hz,

1H), 7.58 (d, J=8.7 Hz, 1H), 7.51 (d, J=8.7 Hz, 1H), 5.03 (d, J=5.8 Hz, 2H), 4.03 (s, 3H), 2.84 (s, 3H), 2.60 (s, 3H). LCMS (Method 3): [MH+]=380 at 2.13 min.

The following compounds reported in the table below were prepared according to the same procedure described for the preparation of 8-methoxy-6-(5-methyl-1,3,4-thiadiazol-2-yl)-N-((6-methylpyridazin-3-yl)methyl)quinazolin-4-amine (Intermediate 16):

| Intermediate No. | Chemical Name Structure | Analytical data $^1$H NMR LC-MS | Starting Intermediate |
|---|---|---|---|
| Intermediate 17 | 8-Methoxy-N-[(6-methylpyridazin-3-yl)methyl]-6-(5-methylpyrimidin-2-yl)quinazolin-4-amine 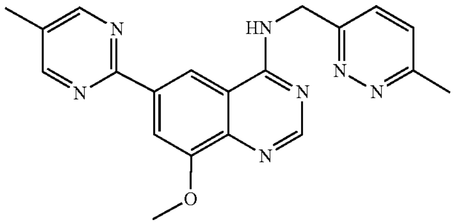 | $^1$H NMR (400 MHz, DMSO): δ 9.29 (dd, J = 5.7, 5.7 Hz, 1 H), 8.93 (d, J = 1.5 Hz, 1 H), 8.84 (s, 2 H), 8.44 (s, 1 H), 8.22 (d, J = 1.5 Hz, 1 H), 7.54 (d, J = 8.7 Hz, 1 H), 7.49 (d, J = 8.7 Hz, 1 H), 5.01 (d, J = 5.8 Hz, 2 H), 4.02 (s, 3 H), 2.60 (s, 3 H), 2.38 (s, 3 H). LCMS (Method 3): [MH+] = 374 at 3.25 min. | Intermediate 8 |

Intermediate 18

(R)-6-(4-fluorophenyl)-4-((1-(2-(trifluoromethyl) pyrimidin-5-yl)ethyl)amino)-quinazolin-8-ol

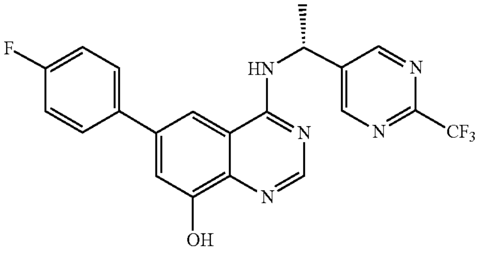 [SMILES: C[C@@H](Nc1ncnc2c(O)cc(-c3ccc(F)cc3)cc12)c1cnc(C(F)(F)F)nc1]

To a solution of 6-(4-fluorophenyl)-8-methoxy-N-[(1R)-1-[2-(trifluoromethyl)-pyrimidin-5-yl]ethyl]quinazolin-4-amine (Intermediate 10) (490 mg, 1.11 mmol) in chloroform (8 mL) at 0° C. was added dropwise boron tribromide (0.32 mL, 3.32 mmol). The reaction was then allowed to warm to room temperature and was heated to 65° C. for 18 hours. After return to room temperature, the reaction was cooled down in an ice-bath and quenched with methanol (2 mL). The solvent was removed in vacuo. The residue was diluted with ethyl acetate (50 mL) and washed with saturated aqueous $NaHCO_3$ solution (50 mL). The aqueous layer was then extracted with ethyl acetate (2×20 mL). The organic phases were combined, passed through a hydrophobic frit and the solvent was removed in vacuo to give the title compound as a grey solid (416 mg, 88%).

$^1$H NMR (400 MHz, DMSO): δ 9.18 (s, 2H), 8.65 (d, J=7.0 Hz, 1H), 8.46 (s, 1H), 8.09 (s, 1H), 7.86 (dd, J=5.5, 8.7 Hz, 2H), 7.45 (d, J=1.3 Hz, 1H), 7.37 (dd, J=8.8, 8.8 Hz, 2H), 5.71-5.67 (m, 1H), 1.75 (d, J=7.0 Hz, 3H), OH not observed.

The following compounds were prepared via adaptations of the above procedure starting from substrate reported in table.

| Intermediate No. | Structure | Analytical data LC-MS | Substrate |
|---|---|---|---|
| Intermediate 19 | 6-(4-fluorophenyl)-4-(((6-methylpyridazin-3-yl)methyl)amino)quinazolin-8-ol 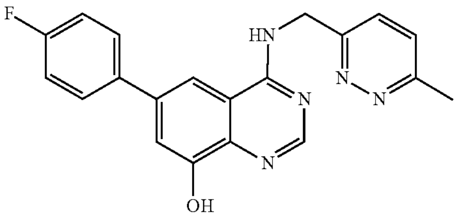 | LCMS: 0.51 min, 362.1 [M + H]+, Method 5 | Intermediate 11 |

-continued

| Intermediate No. | Structure | Analytical data LC-MS | Substrate |
|---|---|---|---|
| Intermediate 19a | (R)-4-((1-(6-methylpyridazin-3-yl)ethyl)amino)-6-(5-methylpyrimidin-2-yl)quinazolin-8-ol 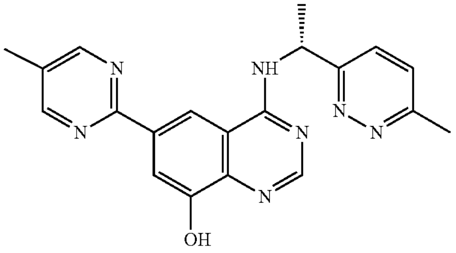 | LCMS (Method 4): [MH+] = 374 at 2.45 min | Intermediate 14 |
| Intermediate 19b | 4-(((6-methylpyridazin-3-yl)methyl)amino)-6-(5-methylpyrimidin-2-yl)quinazolin-8-ol 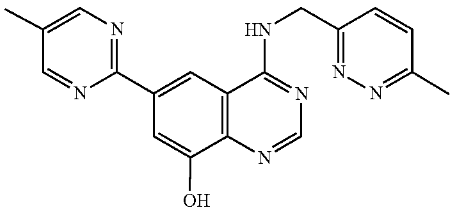 | LCMS (Method5): [MH+] = 360.4 at 0.92 | Intermediate 17 |
| Intermediate 20 | 6-(4-fluorophenyl)-4-(((1-methylpiperidin-4-yl)methyl)amino)quinazolin-8-ol 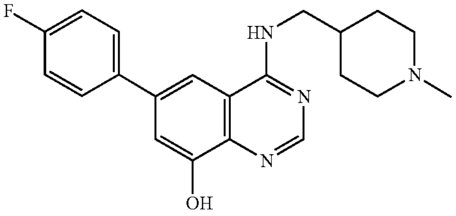 | LCMS (Method5): [MH+] = 367.3 at 0.44 | Intermediate 5 |

Example 1

8-(2,2-difluoroethoxy)-6-(4-fluorophenyl)-N-((6-methylpyridazin-3-yl)methyl)quinazolin-4-amine

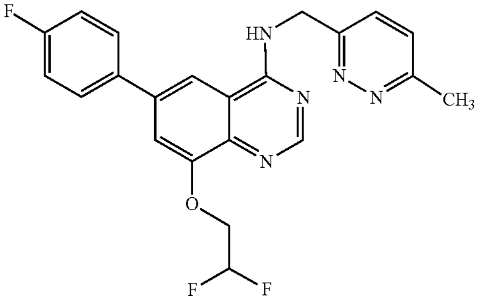 [SMILES: Cc1ccc(CNc2ncnc3c(OCC(F)F)cc(-c4ccc(F)cc4)cc23)nn1]

To a suspension of 6-(4-fluorophenyl)-4-(((6-methylpyridazin-3-yl)methyl)amino)quinazolin-8-ol (100 mg, 0.28 mmol) (Intermediate 19) and cesium carbonate (180 mg, 0.55 mmol) in DMF (1.6 mL), 1,1-difluoro-2-iodoethane (0.04 ml, 0.41 mmol) was added and the reaction was stirred at 70° C. for 2 h. The mixture was concentrated under reduced pressure and the resulting crude was purified by flash chromatography (Biotage Isolera, 30 g C18 cartridge, gradient elution from 0 to 70% B in A. A: water/acetonitrile 95:5+0.05% HCOOH, B: acetonitrile/water 95:5+0.05% HCOOH) to give the title product (14.9 mg, 0.03 mmol, 12.7% yield) as a white solid.

$^1$H NMR (400 MHz, DMSO-d6) δ ppm 9.05 (br s, 1H), 8.41 (s, 1H), 8.21-8.25 (m, 1H), 7.88-7.95 (m, 2H), 7.60-7.66 (m, 1H), 7.43-7.54 (m, 2H), 7.34 (t, J=8.88 Hz, 2H), 6.49 (dt, J=1.00 Hz, 1H), 4.99 (d, J=5.48 Hz, 2H), 4.58 (td, J=14.47, 3.73 Hz, 2H), 2.55 (s, 3H).

Example 2

(R)-8-(2,2-difluoroethoxy)-6-(4-fluorophenyl)-N-(1-(2-(trifluoromethyl)pyrimidin-5-yl)ethyl)quinazolin-4-amine

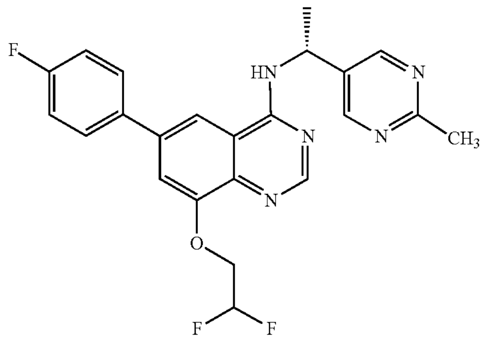 [SMILES: Cc1ncc([C@@H](C)Nc2ncnc3c(OCC(F)F)cc(-c4ccc(F)cc4)cc23)cn1]

A suspension of (R)-6-(4-fluorophenyl)-4-((1-(2-(trifluoromethyl)pyrimidin-5-yl)ethyl)amino)quinazolin-8-ol (100 mg, 0.23 mmol) (Intermediate 18), cesium carbonate (152 mg, 0.47 mmol) and 1,1-difluoro-2-iodoethane (0.03 ml, 0.35 mmol) in DMF (1.6 mL) was stirred at 70° C. for 2 h.

The mixture was then cooled down and partitioned between DCM (10 mL) and 1 M aq HCl (10 mL) and the organic phase separated then concentrated under reduced pressure and the crude purified by RP flash chromatography (Biotage Isolera, 12 g C18 cartridge, gradient elution from 0 to 100% B in A. A: water/acetonitrile 95:5+0.05% HCOOH, B: acetonitrile/water 95:5+0.05% HCOOH) to give the title product (53.5 mg, 0.108 mmol, 46.6% yield) as a yellow solid.

$^1$H NMR (600 MHz, DMSO-d6) δ ppm 9.16 (s, 2H) 8.66 (d, J=6.80 Hz, 1H) 8.44 (s, 1H) 8.28 (d, J=1.54 Hz, 1H) 7.95 (dd, J=8.78, 5.45 Hz, 2H) 7.65 (d, J=1.67 Hz, 1H) 7.39 (t, J=8.43 Hz, 2H) 6.38-6.65 (m, 1H) 5.67 (quin, J=6.99 Hz, 1H) 4.60 (td, J=14.43, 3.72 Hz, 2H) 1.73 (d, J=7.18 Hz, 3H).

LCMS (Method 5): [MH+]=493, 67 at 0.86 min.

Intermediate 21

Methyl 3-(2,2-difluoroethoxy)-2-nitrobenzoate

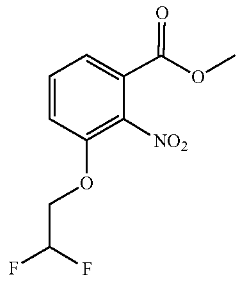 [SMILES: COC(=O)c1cccc(OCC(F)F)c1[N+](=O)[O-]]

To a 10 mL microwave vial was added methyl 3-fluoro-2-nitrobenzoate (600 mg, 3.00 mmol) in DMF (3 mL) and 2,2-difluoroethanol (544 mg, 6.63 mmol). To the stirred solution was added potassium carbonate (833 mg, 6.03 mmol) and the mixture was heated to 120° C. in a microwave reactor for 20 minutes. This procedure was repeated three times, and the pooled reaction mixtures were cooled to room temperature, poured into water (65 mL) and extracted with diethyl ether (30 mL). The aqueous phase was then extracted with additional diethyl ether (2×30 mL). The combined organic layers were dried over magnesium sulfate, filtered and the solvent was removed in vacuo. The resulting residue was purified by flash column chromatography on silica gel eluting with 50% ethyl acetate in cyclohexane to give the title compound (1876 mg, 81%) as a pale yellow solid.

$^1$H NMR (400 MHz, $CDCl_3$): δ 7.71-7.68 (m, 1H), 7.55-7.51 (m, 1H), 7.30-7.26 (m, 1H), 6.22-5.92 (m, 1H), 4.34-4.26 (m, 2H), 3.91-3.90 (m, 3H). LCMS (Method 3): [MH+]=262 at 4.17 min.

Intermediate 22

Methyl 2-amino-3-(2,2-difluoroethoxy)benzoate

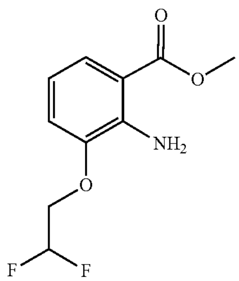

To methyl 3-(2,2-difluoroethoxy)-2-nitrobenzoate (1.85 g, 7.06 mmol) in THF (15 mL), methanol (15 mL) and water (5 mL), was added iron powder (2.59 g, 46.5 mmol) and ammonium chloride (1.24 g, 23.2 mmol). The reaction mixture was heated to 90° C. for 2 hours. After this time the reaction mixture was cooled to room temperature, filtered through Celite® and concentrated in vacuo. The residue was partitioned between ethyl acetate (60 mL) and water (60 mL). The combined organic layers were extracted, dried over magnesium sulfate, filtered and the solvent removed in vacuo to give the title compound (1.48 g, 91%) as a pale yellow oil.

LCMS (Method 3): [MH+]=232 at 4.47 min

Intermediate 23

Methyl 2-amino-5-bromo-3-(2,2-difluoroethoxy)benzoate

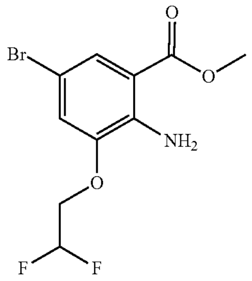 [SMILES: COC(=O)c1cc(Br)cc(OCC(F)F)c1N]

Bromine (0.26 mL, 5.00 mmol) was added dropwise to a solution of Methyl 2-amino-3-(2,2-difluoroethoxy) benzoate (1100 mg, 4.76 mmol) in chloroform (18 mL) at 0° C. The stirring was maintained at 0° C. for 1 hour. The reaction mixture was quenched with sodium thiosulfate and the mixture was stirred for 10 minutes. A saturated sodium hydrogen carbonate solution (6 mL) was added and the reaction was stirred for 5 minutes. The two phases were separated. The aqueous phase was extracted with DCM (2×50 mL). The combined organic phases were concentrated in vacuo to give the title compound (1354 mg, 93%) as an off white solid.

$^1$H NMR (400 MHz, $CDCl_3$): δ 7.68 (d, J=2.3 Hz, 1H), 6.93 (d, J=2.0 Hz, 1H), 6.27-5.96 (m, 3H), 4.25-4.16 (m, 2H), 3.88-3.87 (m, 3H).

Intermediate 24

Methyl 2-amino-3-(2,2-difluoroethoxy)-5-(5-fluoropyridin-2-yl)benzoate

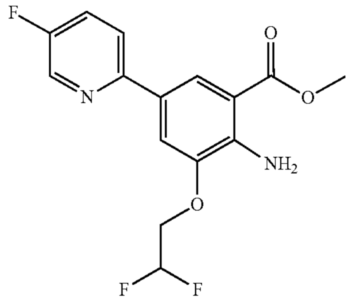 [SMILES: COC(=O)c1cc(-c2ccc(F)cn2)cc(OCC(F)F)c1N]

To methyl 2-amino-5-bromo-3-(2,2-difluoroethoxy)benzoate (422 mg, 1.36 mmol) and tetrakis(triphenylphosphine) palladium(0)(79 mg, 0.07 mmol) in dioxane (5 mL), was added 4-fluoro-2-(tributylstannyl)pyridine (525 mg, 1.36 mmol). The reaction mixture was stirred under a nitrogen atmosphere at 100° C. for 16 hours. After this time the reaction mixture was poured into 1 M aqueous potassium fluoride solution (10 mL) and rapidly stirred for 1 hour. The resulting suspension was filtered through Celite®, washing with ethyl acetate (30 mL). The organic layers were extracted from water (10 mL), washed with saturated aqueous sodium chloride (2×15 mL), dried over magnesium sulfate, filtered and the solvent removed in vacuo. The resulting residue was purified by flash column chromatography on silica gel eluting with 15% ethyl acetate in cyclohexane to give the title compound (261 mg, 59%) as a colourless solid.

$^1$H NMR (400 MHz, CDCl3): δ 8.46 (d, J=3.0 Hz, 1H), 8.09 (d, J=1.9 Hz, 1H), 7.71-7.68 (m, 2H), 7.45-7.40 (m, 1H), 6.31-6.02 (m, 3H), 4.40-4.32 (m, 2H), 3.92 (s, 3H). LCMS (Method 4): [MH+]=327 at 4.95 min.

Intermediate 25

2-Amino-3-(2,2-difluoroethoxy)-5-(5-fluoropyridin-2-yl)benzoic acid

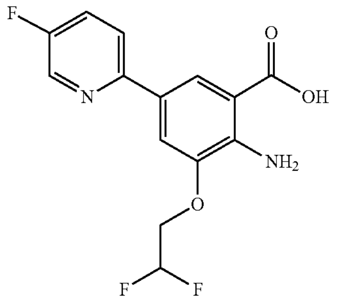 [SMILES: Nc1c(OCC(F)F)cc(-c2ccc(F)cn2)cc1C(=O)O]

To methyl 2-amino-3-(2,2-difluoroethoxy)-5-(5-fluoropyridin-2-yl)benzoate (266 mg, 0.82 mmol) in methanol (5 mL), THF (5 mL) and water (1 mL) was added lithium hydroxide hydrate (29 mg, 1.22 mmol). The reaction mixture was stirred at 50° C. for 16 hours. After this time the reaction mixture was concentrated in vacuo, to give the title compound (282 mg, 100%) as a colourless solid.

$^1$H NMR (400 MHz, DMSO): δ 8.51 (d, J=3.0 Hz, 1H), 8.21 (s, 1H), 7.83 (dd, J=4.4, 8.9 Hz, 1H), 7.72-7.66 (m, 1H), 7.53-7.51 (m, 1H), 6.44 (tt, J=3.6, 54.8 Hz, 1H), 4.38-4.29 (m, 2H).

Intermediate 26

8-(2,2-difluoroethoxy)-6-(5-fluoropyridin-2-yl)quinazolin-4(3H)-one

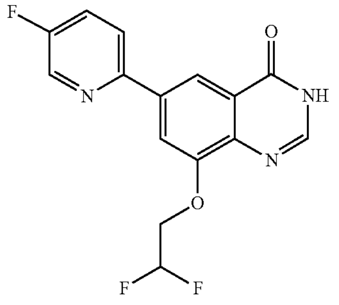 [SMILES: O=c1[nH]cnc2c(OCC(F)F)cc(-c3ccc(F)cn3)cc12]

To amino-3-(2,2-difluoroethoxy)-5-(5-fluoropyridin-2-yl)benzoic acid (220 mg, 0.71 mmol) was added formamide (2 mL). The reaction mixture was stirred at 130° C. for 48 hours. After this time the reaction mixture was cooled to room temperature and poured into water (25 mL). The resulting solid was filtered, washed with water (10 mL), followed by diethyl ether (15 mL) and air dried to give the title compound (205 mg, 91%) as a colourless solid.

$^1$H NMR (400 MHz, DMSO): δ 12.42-12.40 (m, 1H), 8.73 (d, J=2.9 Hz, 1H), 8.46 (d, J=1.8 Hz, 1H), 8.29 (dd, J=4.3, 8.8 Hz, 1H), 8.14 (s, 1H), 8.08 (d, J=1.8 Hz, 1H), 7.94-7.87 (m, 1H), 6.52 (tt, J=3.7, 54.9 Hz, 1H), 4.66-4.56 (m, 2H). LCMS (Method 3): [MH+]=322 at 3.41 min Intermediate 27

4-Chloro-8-(2,2-difluoroethoxy)-6-(5-fluoropyridin-2-yl)quinazoline

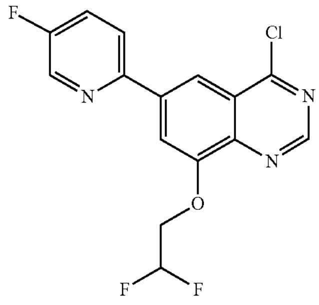 [SMILES: Fc1ccc(-c2cc(OCC(F)F)c3ncnc(Cl)c3c2)nc1]

To 8-(2,2-difluoroethoxy)-6-(5-fluoropyridin-2-yl)quinazolin-4(3H)-one (200 mg, 0.62 mmol) in toluene (7 mL) was added DIPEA (402 mg, 3.11 mmol). The reaction mixture was stirred at 120° C. for 10 minutes, then phosphorus oxychloride (115 mg, 0.75 mmol) was added dropwise. The reaction mixture was then stirred at 120° C. for a further 2 hours. After this time the reaction mixture was cooled to room temperature and solvent removed in vacuo. The resulting residue was partitioned between dichloromethane (10 mL) and saturated aqueous sodium bicarbonate solution (10 mL). The organic layers were separated, dried, filtered and concentrated in vacuo to give the title compound (186 mg, 88%) as a pale brown solid that was directly taken on to the next step.

Example 4

8-(2,2-difluoroethoxy)-6-(5-fluoropyridin-2-yl)-N-((6-methylpyridazin-3-yl)methyl)quinazolin-4-amine

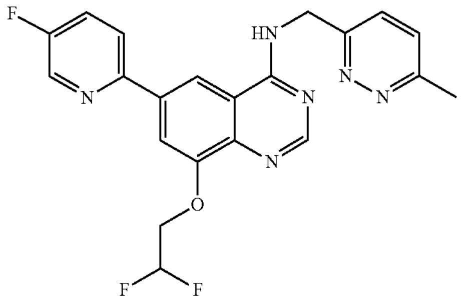 [SMILES: Cc1ccc(CNc2ncnc3c(OCC(F)F)cc(-c4ccc(F)cn4)cc23)nn1]

To crude 4-chloro-8-(2,2-difluoroethoxy)-6-(5-fluoropyridin-2-yl)quinazoline (65 mg, 0.19 mmol) and (6-methylpyridazin-3-yl)methanamine (28 mg, 0.23 mmol) in 1,4-dioxane (3 mL) was added DIPEA (124 mg, 0.95 mmol). The reaction mixture was stirred at 50° C. for 16 hours. After this time the reaction mixture was cooled to room temperature and solvents removed in vacuo. The resulting residue was purified by preparative HPLC to give the title compound (38 mg, 28%) as an off-white solid.

$^1$H NMR (400 MHz, DMSO): δ 9.20 (dd, J=5.8, 5.8 Hz, 1H), 8.74 (d, J=3.0 Hz, 1H), 8.67 (d, J=1.5 Hz, 1H), 8.48 (s, 1H), 8.28 (dd, J=4.1, 8.9 Hz, 1H), 8.06 (d, J=1.4 Hz, 1H), 8.01-7.95 (m, 1H), 7.58 (d, J=8.7 Hz, 1H), 7.51 (d, J=8.8 Hz, 1H), 6.54 (tt, J=3.6, 54.6 Hz, 1H), 5.05 (d, J=5.8 Hz, 2H), 4.65-4.56 (m, 2H), 2.61 (s, 3H). LCMS (Method 4): [MH+] =427 at 2.77 min.

The following compound reported in the table below was prepared according to the same procedure described for the preparation of 8-(2,2-difluoroethoxy)-6-(5-fluoropyridin-2-yl)-N-((6-methylpyridazin-3-yl)methyl)quinazolin-4-amine:

| Example No. | Chemical Name Structure | Analytical data $^1$H NMR LC-MS |
|---|---|---|
| Example 5 | (R)-8-(2,2-difluoroethoxy)-6-(5-fluoropyridin-2-yl)-N-(1-(6-methylpyridazin-3-yl)ethyl)quinazolin-4-amine 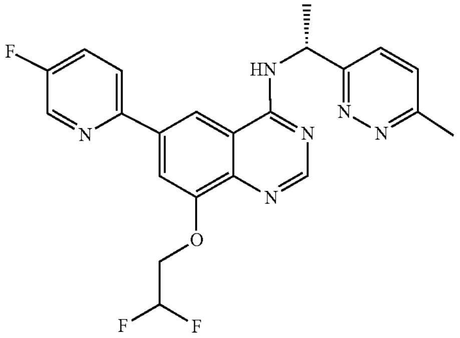 | $^1$H NMR (400 MHz, DMSO): δ 8.85 (d, J = 7.3 Hz, 1 H), 8.77-8.74 (m, 2 H), 8.43 (s, 1 H), 8.34 (dd, J = 4.3, 8.9 Hz, 1 H), 8.06 (d, J = 1.4 Hz, 1 H), 8.02-7.96 (m, 1 H), 7.64 (d, J = 8.7 Hz, 1 H), 7.51 (d, J = 8.8 Hz, 1 H), 6.52 (tt, J = 19.4, 41.8 Hz, 1 H), 5.81-5.75 (m, 1 H), 4.64-4.54 (m, 2 H), 2.60 (s, 3 H), 1.74 (d, J = 7.0 Hz, 3 H). LCMS (Method 4): [MH+] = 441 at 2.95 min. |

The following compounds reported in the table below were obtained as single isomers by chiral preparative SFC purification of the corresponding racemic mixture, which was prepared according to the same procedure described for the preparation of 8-(2,2-difluoroethoxy)-6-(5-fluoropyridin-2-yl)-N-((6-methylpyridazin-3-yl)methyl)quinazolin-4-amine:

| Example No. | Chemical name Structure | Analytical data $^1$H NMR LC-MS |
|---|---|---|
| Example 6 | Single enantiomer 1 of 8-(2,2-difluoroethoxy)-6-(5-fluoro-2-pyridyl)-N-[1-(5-methyl-1,3,4-thiadiazol-2-yl)ethyl]quinazolin-4-amine 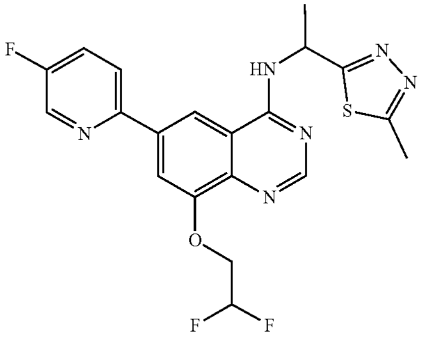 | $^1$H NMR (400 MHz, DMSO): δ 9.03-8.99 (m, 1 H), 8.74 (d, J = 2.9 Hz, 1 H), 8.67 (d, J = 1.5 Hz, 1 H), 8.56-8.55 (m, 1 H), 8.32-8.27 (m, 1 H), 8.07 (d, J = 1.5 Hz, 1 H), 8.01-7.93 (m, 1 H), 6.69-6.38 (m, 1 H), 6.03-5.95 (m, 1 H), 4.65-4.56 (m, 2 H), 2.66 (s, 3 H), 1.82 (d, J = 7.0 Hz, 3 H). LCMS (Method 4): [MH$^+$] = 447 at 3.15 min. Chiral analysis (Method 22) at 4.5 min. |
| Example 7 | Single enantiomer 2 of 8-(2,2-difluoroethoxy)-6-(5-fluoro-2-pyridyl)-N-[1-(5-methyl-1,3,4-thiadiazol-2-yl)ethyl]quinazolin-4-amine 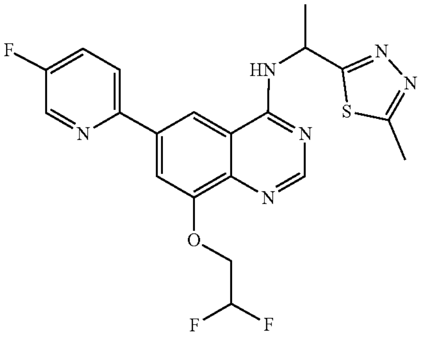 | $^1$H NMR (400 MHz, DMSO): δ 9.02 (d, J = 7.5 Hz, 1 H), 8.74 (d, J = 2.9 Hz, 1 H), 8.68 (d, J = 1.6 Hz, 1 H), 8.56 (s, 1 H), 8.30 (dd, J = 4.1, 8.9 Hz, 1 H), 8.07 (d, J = 1.5 Hz, 1 H), 7.98 (ddd, J = 8.7, 8.7, 3.0 Hz, 1 H), 6.69-6.39 (m, 1 H), 6.03-5.95 (m, 1 H), 4.66-4.56 (m, 2 H), 2.66 (s, 3 H), 1.82 (d, J = 7.0 Hz, 3 H). LCMS (Method 4): [MH$^+$] = 447 at 3.03 min. Chiral analysis (Method 22) at 5.3 min. |

Example 8

8-(2,2-Difluoroethoxy)-N-((6-methylpyridazin-3-yl)methyl)-6-(5-methylpyridin-2-yl)quinazolin-4-amine

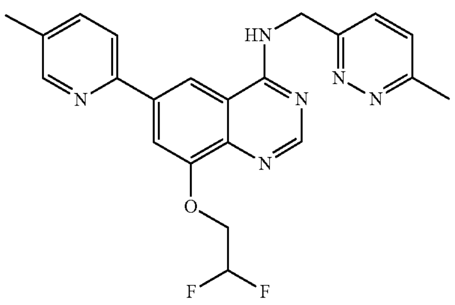

Intermediate 28

2-Amino-5-bromo-3-(2,2-difluoroethoxy) benzoic acid

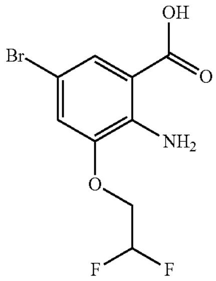

Methyl 2-amino-5-bromo-3-(2,2-difluoroethoxy) benzoate (1354 mg, 4.37 mmol) was dissolved in THF (30 mL) and methanol (30 mL). A solution of lithium hydroxide (157 mg, 6.55 mmol) in water (4 mL) was added and the reaction was stirred at 50° C. for 18 hours. The reaction mixture was concentrated in vacuo to give the title compound (1351 mg, >100%) as an orange solid.

$^1$H NMR (400 MHz, MeOD): δ 7.56 (d, J=2.3 Hz, 1H), 6.89 (d, J=2.3 Hz, 1H), 6.25 (t, J=3.9 Hz, 1H), 6.12 (t, J=3.8 Hz, 1H), 5.98 (t, J=3.8 Hz, 1H), 4.17-4.08 (m, 2H).

Intermediate 29

6-Bromo-8-(2,2-difluoroethoxy)quinazolin-4-ol

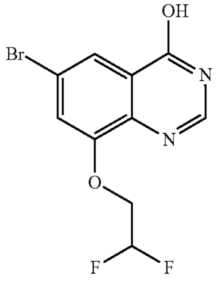 [SMILES: Oc1ncnc2c(OCC(F)F)cc(Br)cc12]

2-Amino-5-bromo-3-(2,2-difluoroethoxy)benzoic acid (1250 mg, 4.22 mmol) was dissolved in formamide (12 mL). The reaction was stirred at 130° C. for 24 hours. The mixture was diluted with water and filtered. The solid was then washed with water followed by 9:1 diethyl ether/methanol to give the title compound (781 mg, 61%) as a light brown solid.

$^1$H NMR (400 MHz, DMSO): δ 8.12-8.11 (m, 1H), 7.82 (d, J=2.0 Hz, 1H), 7.63-7.62 (m, 1H), 6.61-6.31 (m, 1H), 4.56-4.46 (m, 2H).

Intermediate 29a

6-Bromo-4-chloro-8-(2,2-difluoroethoxy)quinazoline

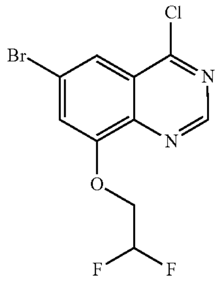 [SMILES: FC(F)COc1cc(Br)cc2c(Cl)ncnc12]

6-Bromo-8-(2,2-difluoroethoxy)quinazolin-4-ol (400 mg, 1.31 mmol) was dissolved on toluene (14 mL) and DIPEA (1.1 mL, 6.56 mmol) was added. The mixture was heated to 90° C. for 5 minutes. Phosphorus (V) oxychloride (0.15 mL, 1.57 mmol) was added and the reaction mixture was heated at 90° C. for 3 hours. The reaction mixture was concentrated in vacuo and the residue partitioned between DCM and sodium hydrogen carbonate. The two phases were separated and the aqueous phase was extracted with DCM (2×50 mL). The combined organic phases were concentrated in vacuo to give the title compound (502 mg, >100%) as a brown solid.

$^1$H NMR (400 MHz, $CDCl_3$): δ 9.10-9.09 (m, 1H), 8.12-8.10 (m, 1H), 7.45 (d, J=1.8 Hz, 1H), 6.47-6.16 (m, 1H), 4.53-4.45 (m, 2H).

Intermediate 30

6-Bromo-8-(2,2-difluoroethoxy)-N-((6-methylpyridazin-3-yl)methyl)quinazolin-4-amine

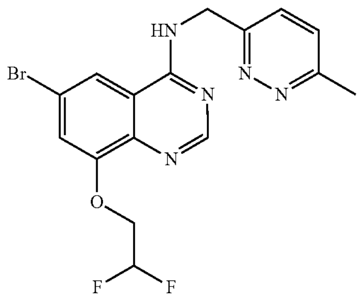 [SMILES: Cc1ccc(CNc2ncnc3c(OCC(F)F)cc(Br)cc23)nn1]

6-Bromo-4-chloro-8-(2,2-difluoroethoxy)quinazoline (424 mg, 1.31 mmol) was dissolved in dioxane (6 mL). DIPEA (1.1 mL, 6.55 mmol) and (6-methylpyridazin-3-yl)methanamine (308 mg, 1.57 mmol) were added and the reaction mixture was heated at 95° C. for 3 hours. The mixture was concentrated in vacuo and the residue was partitioned between DCM and water. The two phases were separated. The aqueous phase was extracted with DCM (2×50 mL). The combined organic phases were concentrated in vacuo. The residue was purified by flash chromatography on silica gel eluting with 75% methanol in ethyl acetate to give the title compound (374 mg, 70%) as a light brown solid.

$^1$H NMR (400 MHz, DMSO): δ 9.05-9.00 (m, 1H), 8.45-8.44 (m, 1H), 8.24-8.22 (m, 1H), 7.55-7.46 (m, 3H), 6.49-6.47 (m, 1H), 4.98-4.95 (m, 2H), 4.57-4.46 (m, 2H), 2.58 (s, 3H).

Example 8

8-(2,2-Difluoroethoxy)-N-((6-methylpyridazin-3-yl) methyl)-6-(5-methylpyridin-2-yl)quinazolin-4-amine

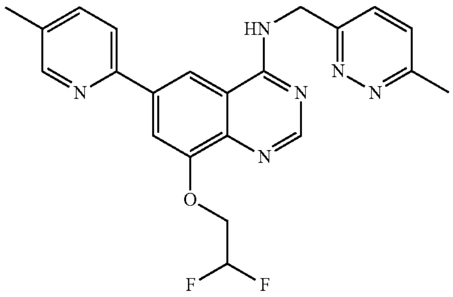

6-Bromo-8-(2,2-difluoroethoxy)-N-((6-methylpyridazin-3-yl)methyl)quinazolin-4-amine (180 mg, 0.590 mmol), [1,1'-bis(diphenylphosphino)ferrocene]dichloropalladium (II), complex with dichloromethane (24 mg, 0.0295 mmol), bis(pinacolato)diboron (180 mg, 0.708 mmol) and potassium acetate (69 mg, 0.708 mmol) were dissolved in dioxane (5 mL) and heated to 100° C. for 2 hours. A further aliquot of 6-Bromo-8-(2,2-difluoroethoxy)-N-((6-methylpyridazin-3-yl)methyl)quinazolin-4-amine (50 mg, 0.122 mmol) was added and the reaction mixture was heated at 100° C. for a further 16 hours. The reaction mixture was allowed to cool to room temperature and the mixture was halved. 2-Bromo-5-methylpyridine (107 mg, 0.620 mmol), cesium carbonate (384 mg, 1.18 mmol), [1,1'-bis(diphenylphosphino)ferrocene]-dichloropalladium(II), complex with dichloromethane (24 mg, 0.0295 mmol) and water (2 mL) were added. The reaction mixture was heated at 100° C. for 2 hours. The reaction mixture was then concentrated in vacuo and the residue was partitioned between DCM and water. The two phases were separated and the aqueous phase was extracted with DCM (2×50 mL). The combined organic phases were concentrated in vacuo. Purification by preparative HPLC afforded the title compound (5 mg, 4%) as a white solid.

$^1$H NMR (400 MHz, DMSO): δ 9.23 (t, J=5.7 Hz, 1H), 8.72-8.70 (m, 1H), 8.62 (d, J=2.0 Hz, 1H), 8.51-8.50 (m, 1H), 8.18-8.13 (m, 2H), 7.88-7.84 (m, 1H), 7.63-7.53 (m, 2H), 6.72-6.42 (m, 1H), 5.11-5.07 (m, 2H), 4.69-4.60 (m, 2H), 2.65-2.64 (m, 3H), 2.44-2.43 (m, 3H). LCMS (Analytical Method 3): [MH]=423 at 4.01 min.

The following compound reported in the table below was prepared according to the same procedure described for the preparation of 8-(2,2-Difluoroethoxy)-N-((6-methylpyridazin-3-yl)methyl)-6-(5-methylpyridin-2-yl)quinazolin-4-amine (Example 8):

| Example No. | Chemical Name Structure | Analytical data $^1$H NMR LC-MS |
|---|---|---|
| Example 9 | 8-(2,2-difluoroethoxy)-N-[(6-methylpyridazin-3-yl)methyl]-6-(5-methylpyrimidin-2-yl)quinazolin-4-amine 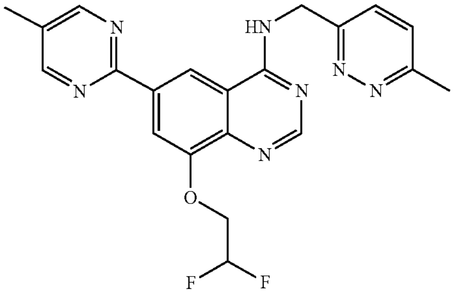 | $^1$H NMR (400 MHz, DMSO): δ 9.37 (t, J = 5.8 Hz, 1 H), 9.02 (d, J = 1.5 Hz, 1 H), 8.85 (d, J = 0.6 Hz, 2 H), 8.48-8.48 (m, 1 H), 8.29 (d, J = 1.5 Hz, 1 H), 7.56-7.48 (m, 2 H), 5.02 (d, J = 5.8 Hz, 2 H), 4.65-4.56 (m, 2 H), 3.29 (s, 1 H), 2.60 (s, 3 H), 2.38 (s, 3 H). LCMS (Method 3): [MH$^+$] = 424 at 3.37 min. |

Intermediate 31

2-amino-3-(morpholinosulfonyl)benzoic acid

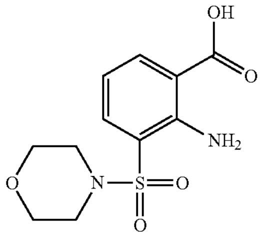 [SMILES: Nc1c(C(=O)O)cccc1S(=O)(=O)N1CCOCC1]

To a solution of morpholine (0.741 ml, 8.47 mmol) in water (50 ml), 3-(chlorosulfonyl)-2-nitrobenzoic acid (0.75 g, 2.82 mmol) was added in 10 min and stirred for 30 min, then, Pd/C 10% (50% wet) (2.82 mmol) and aqueous hydrogen chloride 2 N aq (0.103 g, 2.82 mmol) were added and the reaction was stirred overnight under hydrogen atmosphere (balloon). The catalyst was filtered off and the solvent removed under reduced pressure. The crude was purified by C18 flash chromatography ((H2O/ACN)) 95:5+0.1% HCOOH}:{(ACN/H2O) 95:5+HCOOH 0.1%} from 100:0 to 0:100 affording 2-amino-3-(morpholinosulfonyl) benzoic acid (0.80 g, 2.79 mmol, 99% yield) as a brown solid.

LCMS (Method 5): 0.75 min, [M+H]+ 287.75

The following compound reported in the table below was prepared via adaptation of the above procedure.

| Intermediate No. | Chemical Name Structure | Analytical data LC-MS | Reagents |
|---|---|---|---|
| Intermediate 32 | 2-amino-5-bromo-3-(N,N-dimethylsulfamoyl)benzoic acid 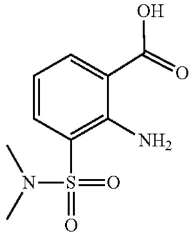 | LCMS(Method5): 0.98 min, [M + H]+ 322.76 | dimethylamine 2M in THF |
| Intermediate 33 | 2-amino-3-((3,3-difluoropyrrolidin-1-yl)sulfonyl)benzoic acid 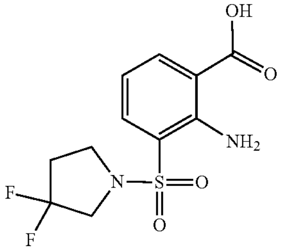 | LCMS(Method5A): 1.55 min, [M + H]+ 306.75 | 3,3-difluoro-pyrrolidine hydrochloride |
| Intermediate 34 | 2-amino-3-((4-hydroxypiperidin-1-yl)sulfonyl)benzoic acid 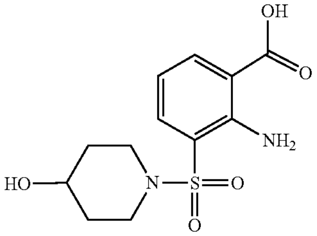 | LCMS(Method5): 0.67 min, 300.99 [M + H]+ | piperidin-4-ol |

-continued

| Intermediate No. | Chemical Name Structure | Analytical data LC-MS | Reagents |
|---|---|---|---|
| Intermediate 35 | 2-amino-3-(N-methylsulfamoyl)benzoic acid 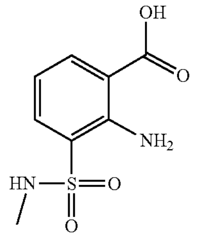 | LCMS(Method5): 0.63 min, [M + H]+ 230.9 | methyl amine solution 2M in THF |
| Intermediate 36 | 2-amino-3-((4-((benzyloxy)carbonyl) piperazin-1-yl)sulfonyl)benzoic acid 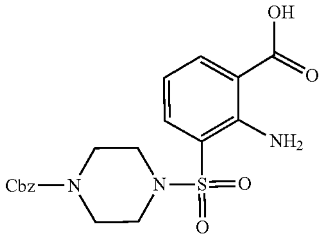 | LCMS(Method5): 1.07 min, [M + H]+ 419.72 | benzyl piperazine-1-carboxylate |

Intermediate 37

Preparation of 2-amino-5-bromo-3-(morpholinosulfonyl)benzoic acid

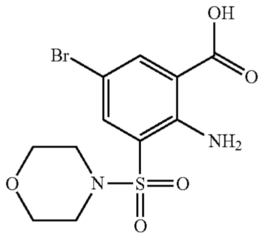 [SMILES: Nc1c(C(=O)O)cc(Br)cc1S(=O)(=O)N1CCOCC1]

To a solution of 2-amino-3-(morpholinosulfonyl)benzoic acid (0.8 g, 2.79 mmol) (Intermediate 29) in DMF, NBS (0.567 ml, 2.79 mmol) was added and the solution stirred for 30 min. Then, solvent was removed and the crude was purified by C18 flash chromatography (($H_2O$/ACN)) 95:5+ 0.1% HCOOH}:{(ACN/$H_2O$) 95:5+HCOOH 0.1%} from 100:0 to 0:100 affording 2-amino-5-bromo-3-(morpholinosulfonyl)benzoic acid (0.85 g, 2.328 mmol, 83% yield) as a white off solid.

LCMS (Method 5): 0.98 min, 366.56 [M+H]+

The following compound reported in the table below was prepared via adaptation of the above procedure.

| Intermediate No. | Chemical Name Structure | Analytical data LC-MS | Reagents |
|---|---|---|---|
| Intermediate 38 | 2-amino-5-bromo-3-(N,N-dimethylsulfamoyl)-benzoic acid 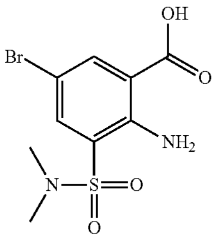 | LCMS(Method5): 0.98 min, [M + H]+ 322.76 | Intermediate 32 |

-continued

| Intermediate No. | Chemical Name Structure | Analytical data LC-MS | Reagents |
|---|---|---|---|
| Intermediate 39 | 2-amino-5-bromo-3-(3,3-difluoropyrrolidin-1-yl)sulfonyl)-benzoic acid 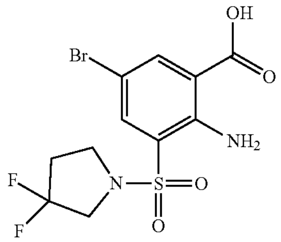 | LCMS(Method5): 1.11 min, [M + H]+ 384.56 | Intermediate 33 |
| Intermediate 40 | 6-bromo-8-((4-hydroxypiperidin-1-yl)-sulfonyl)quinazolin-4-ol 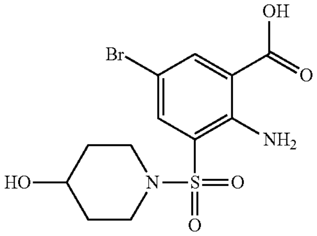 | LCMS(Method5): 0.86 min, 378.96 [M + H]+ | Intermediate 34 |
| Intermediate 41 | 2-amino-5-bromo-3-(N-methylsulfamoyl)-benzoic acid 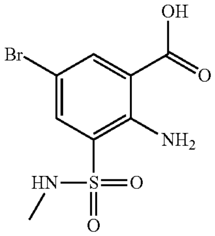 | LCMS(Method5): 0.84 min, [M + H]+ 308.61 | Intermediate 35 |
| Intermediate 42 | 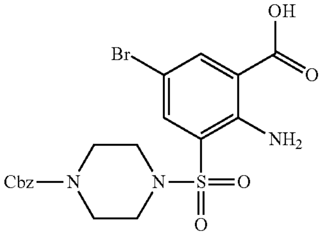 [SMILES: Nc1c(C(=O)O)cc(Br)cc1S(=O)(=O)N1CCN(C(=O)OCc2ccccc2)CC1] | LCMS(Method5): 1.07 min, [M + H]+ 497.77 | Intermediate 36 |

Intermediate 43

6-bromo-8-(morpholinosulfonyl)quinazolin-4-ol

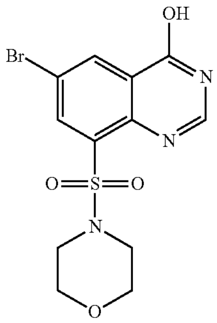 [SMILES: O=S(=O)(c1cc(Br)cc2c(O)ncnc12)N1CCOCC1]

To a solution 2-amino-5-bromo-3-(morpholinosulfonyl) benzoic acid (600 mg, 1.643 mmol) (Intermediate 35) in Formamide (6 ml), ethanesulfonic acid (0.6 ml, 1.643 mmol) was added and the mixture heated to 120 C for 48 h. The reaction was directly loaded on C18 cartridge by reverse chromatography (($H_2O$/ACN)) 95:5+0.1% HCOOH}:{(ACN/H2O) 95:5+HCOOH 0.1%} from 100:0 to 0:100 affording 6-bromo-8-(morpholinosulfonyl)quinazolin-4-ol (0.230 g, 0.615 mmol, 37.4% yield) as a brown solid.

LCMS (Method 5): 0.72 min [M+H]+ 375.56

The following compound reported in the table below was prepared via adaptation of the above procedure.

| Intermediate No. | Chemical Name Structure | Analytical data LC-MS | Reagents |
|---|---|---|---|
| Intermediate 44 | 6-bromo-4-hydroxy-N,N-dimethylquinazoline-8-sulfonamide 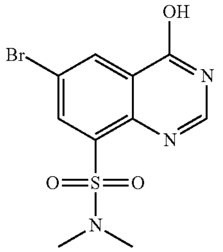 | LCMS(Method5): 0.74 min, [M + H]+ 331.71 | Intermediate 38 |
| Intermediate 45 | 6-bromo-8-((3,3-difluoro-pyrrolidin-1-yl)sulfonyl)-quinazolin-4-ol 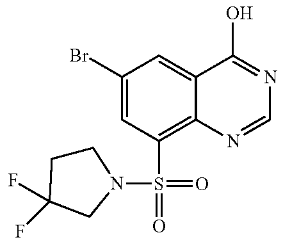 | LCMS(Method5): 0.88 min, [M + H]+ 393.66 | Intermediate 39 |
| Intermediate 46 | 6-bromo-8-((4-hydroxypiperidin-1-yl)-sulfonyl)quinazolin-4-ol 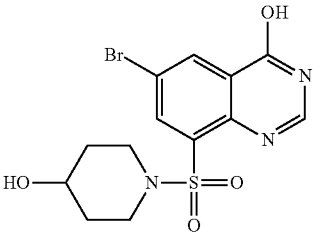 | LCMS(Method5): 0.66 min, 387.95 [M + H]+ | Intermediate 40 |

-continued

| Intermediate No. | Chemical Name Structure | Analytical data LC-MS | Reagents |
|---|---|---|---|
| Intermediate 47 | 6-bromo-4-hydroxy-N-methylquinazoline-8-sulfonamide 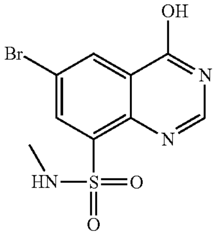 | LCMS(Method5): 0.69 min, [M + H]+ 317.81 | Intermediate 41 |
| Intermediate 48 | benzyl 4-((6-bromo-4-hydroxy-quinazolin-8-yl)sulfonyl)piperazine-1-carboxylate 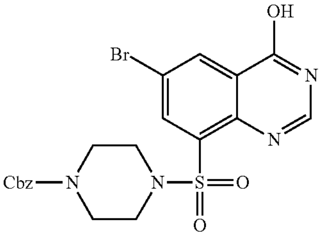 | LCMS(Method5A): 1.05 min, 506.67 [M + H]+ | Intermediate 42 |

Intermediate 50

6-(4-fluorophenyl)-8-(morpholinosulfonyl)quinazolin-4-ol

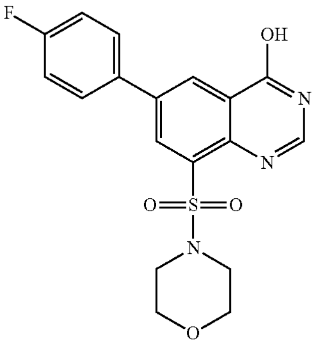 [SMILES: O=S(=O)(c1cc(-c2ccc(F)cc2)cc2c(O)ncnc12)N1CCOCC1]

To a suspension of 6-bromo-8-(morpholinosulfonyl)quinazolin-4-ol (250 mg, 0.668 mmol) in Dioxane (10 ml), Water (3 ml), 4-fluorophenylboronic acid (187 mg, 1.336 mmol), K2CO3 (277 mg, 2.004 mmol) PdCl2(dppf)(56 mg, 0.07 mmol) were added and the reaction was stirred overnight. Then, solvent was removed and the crude was purified by C18 flash chromatography ((H2O/ACN)) 95:5+0.1% HCOOH}:{(ACN/H2O) 95:5+HCOOH 0.1%} from 100:0 to 0:100 affording 6-(4-fluorophenyl)-8-(morpholinosulfonyl)quinazolin-4-ol (204 mg, 0.524 mmol, 78% yield) as a brown solid.

LCMS (Method 5): 0.87 min, [M+H]+ 389.81

The following compounds reported in the table below was prepared via adaptation of the above procedure.

| Intermediate No. | Chemical Name Structure | Analytical data LC-MS | Reagents |
|---|---|---|---|
| Intermediate 51 | 6-(4-fluorophenyl)-4-hydroxy-N,N-dimethylquinazoline-8sulfonamide 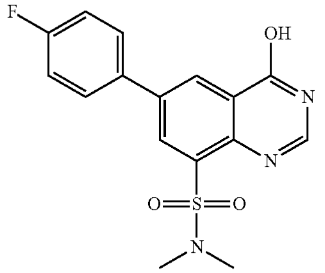 | LCMS(Method5): 0.91 min, [M + H]+ 347.81 | Intermediate 44 |
| Intermediate 52 | 8-((3,3-difluoropyrrolidin-1-yl)-sulfonyl)-6-(4-fluorophenyl)-quinazolin-4-ol 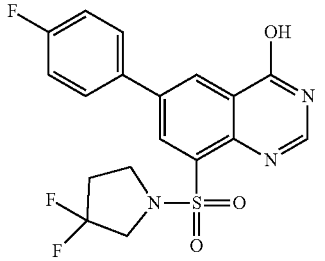 | LCMS(Method5): 1.01 min, 410.02 [M + H]+ | Intermediate 45 |
| Intermediate 53 | 6-(4-fluorophenyl)-8-((4-hydroxypiperi-din-1-yl)sulfonyl)quinazolin-4-ol 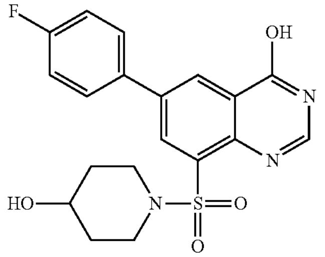 | LCMS(Method5): 0.80 min, 404.32 [M + H]+ | Intermediate 46 |
| Intermediate 54 | 6-(4-fluorophenyl)-4-hydroxy-N-methylquinazoline-8-sulfonamide 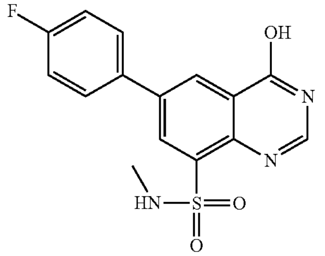 | LCMS(Method5): 0.85 min, [M + H]+ 333.81 | Intermediate 47 |

-continued

| Intermediate No. | Chemical Name Structure | Analytical data LC-MS | Reagents |
|---|---|---|---|
| Intermediate 55 | benzyl 4-((6-(4-fluorophenyl)-4-hydroxyquinazolin-8-yl)sulfonyl)-piperazine-1-carboxylate 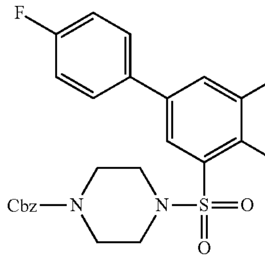 | LCMS(Method5A): 1.13 min, 522.52 [M + H]+ | Intermediate 48 |

Example 10

(R)-6-(4-fluorophenyl)-N-(1-(6-methylpyridazin-3-yl)ethyl)-8-(morpholinosulfonyl)quinazolin-4-amine

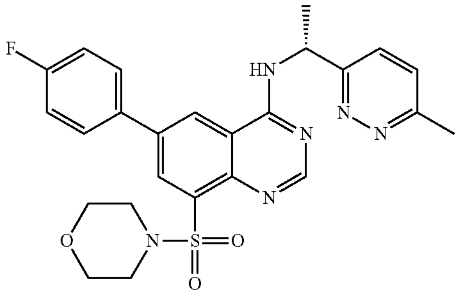

To a solution of 6-(4-fluorophenyl)-8-(morpholinosulfonyl)quinazolin-4-ol (60 mg, 0.154 mmol) in dry DMF (4 ml), PyBOP (96 mg, 0.185 mmol) and DIPEA (0.059 ml, 0.339 mmol) were added and the reaction was stirred for 30 min. Then, ((R)-1-(6-methylpyridazin-3-yl)ethan-1-amine dihydrochloride (32.4 mg, 0.154 mmol) was added and the reaction was further stirred for 30 min. Then, solvent was removed and the crude purified by C18 flash chromatography ((H2O/ACN)) 95:5+0.1% HCOOH}:{(ACN/H2O) 95:5+HCOOH 0.1%} from 100:0 to 0:100 affording (R)-6-(4-fluorophenyl)-N-(1-(6-methylpyridazin-3-yl)ethyl)-8-(morpholinosulfonyl)quinazolin-4-amine (10 mg, 0.020 mmol, 12.76% yield) as a yellowish solid.

$^1$H NMR (400 MHz, DMSO-d)) ppm 9.20 (s, 2H), 9.01 (br d, J=6.58 Hz, 1H), 8.95 (s, 1H), 8.56 (s, 1H), 8.54 (s, 1H), 7.92 (br dd, J=8.22, 5.59 Hz, 2H), 7.43 (br t, J=8.66 Hz, 2H), 5.71 (br quin, J=6.80 Hz, 1H), 4.33 (br t, J=4.82 Hz, 2H), 3.52-3.61 (m, 4H), 3.39-3.50 (m, 2H), 1.75 (br d, J=7.02 Hz, 3H)

LCMS (Method 5): 1.58 min, 509.13 [M+H]+

The following compounds reported in the table below was prepared via adaptation of the above procedure with the appropriate intermediate.

| Example No. | Chemical name Structure | Analytical data $^1$H NMR/LC-MS | Reagents |
|---|---|---|---|
| Example 11 | (R)-6-(4-fluorophenyl)-8-(morpholinosulfonyl)-N-(1-(2-(trifluoromethyl)pyrimidin-5-yl)ethyl)quinazolin-4-amine 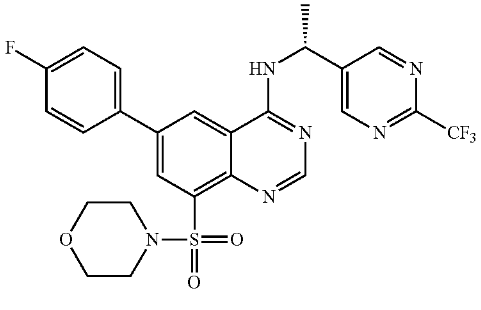 | $^1$H NMR (400 MHz, DMSO-$d_6$) δ ppm 9.20 (s, 2 H), 9.01 (br d, J = 6.58 Hz, 1 H), 8.95 (s, 1 H), 8.56 (s, 1 H), 8.54 (s, 1 H), 7.92 (br dd, J = 8.22, 5.59 Hz, 2 H), 7.43 (br t, J = 8.66 Hz, 2 H), 5.71 (br quin, J = 6.80 Hz, 1 H), 4.33 (br t, J = 4.82 Hz, 2 H), 3.52-3.61 (m, 4 H), 3.39-3.50 (m, 2 H), 1.75 (br d, J = 7.02 Hz, 3 H) LCMS (Method5): [MH+] = 509.13 at 1.58 min. | Intermediate 50 |

-continued

| Example No. | Chemical name Structure | Analytical data $^1H$ NMR/LC-MS | Reagents |
|---|---|---|---|
| Example 12 | (Rac)-6-(4-fluorophenyl)-N-(1-(5-methyl-1,3,4-thiadiazol-2-yl)ethyl)-8-(morpholinosulfonyl)-quinazolin-4-amine 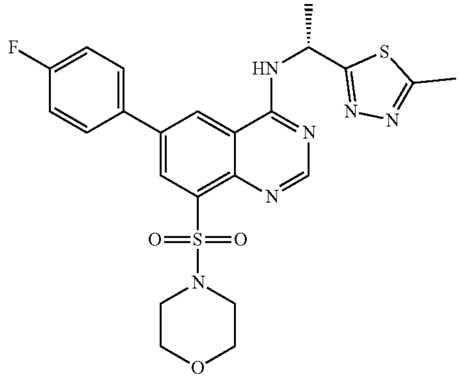 | $^1H$ NMR (600 MHz,DMSO-d6) δ ppm 9.22 (d, J = 7.42 Hz, 1 H) 8.95 (d, J = 2.06 Hz, 1 H) 8.66 (s, 1 H) 8.57 (d, J = 1.92 Hz, 1 H) 7.92 (dd, J = 8.80, 5.36 Hz, 2 H) 7.43 (t, J = 8.35 Hz, 2 H) 6.01 (quin, J = 7.11 Hz, 1 H) 3.57-3.60 (m, 4 H) 2.66 (s, 3 H) 2.52-2.55 (m, 4 H) 1.82 (d, J = 7.01 Hz, 3 H) LCMS (Method5): [MH+] = 515.01 at 0.98 min | Intermediate 50 |
| Example 13 | (R)-6-(4-fluorophenyl)-N,N-dimethyl-4-((1-(6-methyl-pyridazin-3-yl)ethyl)amino)quinazoline-8-sulfonamide 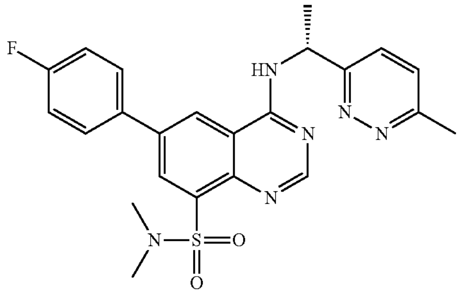 | $^1H$ NMR (400 MHz, DMSO-d6) δ ppm 9.06 (d, J = 7.23 Hz, 1 H) 9.02 (d, J = 1.97 Hz, 1 H) 8.54 (d, J = 1.97 Hz, 1 H) 8.51 (s, 1 H) 7.93 (dd, J = 8.77, 5.26 Hz, 2 H) 7.65 (d, J = 8.77 Hz, 1 H) 7.50 (d, J = 8.55 Hz, 1 H) 7.43 (t, J = 8.77 Hz, 2 H) 5.78 (quin, J = 7.07 Hz, 1 H) 2.86 (s, 6 H) 2.58 (s, 3 H) 1.73 (s, 3 H). LCMS (Method5): [MH+] = 466.62 at 0.92 min | Intermediate 51 |
| Example 14 | 6-(4-fluorophenyl)-N,N-dimethyl-4-((1-(5-methyl-1,3,4-thiadiazol-2-yl)ethyl)amino)quinazoline-8-sulfonamide 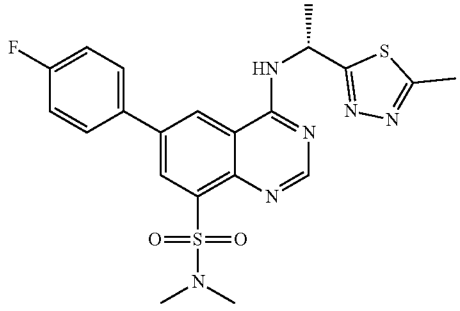 | $^1H$ NMR (400 MHz, DMSO-d6) δ ppm 9.16 (br d, J = 7.45 Hz, 1 H) 8.89 (s, 1 H) 8.62 (s, 1 H) 8.52 (s, 1 H) 7.87 (dd, J = 8.44, 5.59 Hz, 2 H) 7.39 (t, J = 8.77 Hz, 2 H) 5.96 (quin, J = 7.02 Hz, 1 H) 2.84 (s, 6 H) 2.62 (s, 3 H) 1.78 (d, J = 7.02 Hz, 3 H) LCMS (Method5): [MH+] = 472.7 at 1.0 min | Intermediate 51 |

-continued

| Example No. | Chemical name Structure | Analytical data $^1$H NMR/LC-MS | Reagents |
|---|---|---|---|
| Example 15 | 6-(4-fluorophenyl)-N,N-dimethyl-4-((1-(5-methyl-1,2,4-oxadiazol-3-yl)ethyl)amino)quinazoline-8-sulfonamide 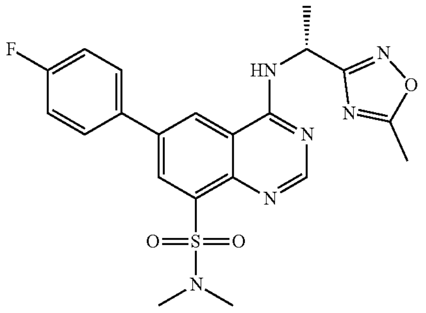 | $^1$H NMR (400 MHz, DMSO-$d_6$) δ ppm 9.03 (d, J =7.13 Hz, 1 H) 8.95 (d, J = 1.75 Hz, 1 H) 8.60 (s, 1 H) 8.55 (d, J = 1.75 Hz, 1 H) 7.91 (dd, J = 8.66, 5.37 Hz, 2 H) 7.42 (t, J = 8.77 Hz, 2 H) 5.77 (quin, J = 7.18 Hz, 1 H) 2.87 (s, 6 H) 2.57 (s, 3 H) 1.69 (d, J = 7.02 Hz, 3 H). LCMS (Method5): [MH+] = 457.6 at 1.02 min | Intermediate 51 |
| Example 16 | | $^1$H NMR (400 MHz, DMSO-d6) δ ppm 9.07 (d, J = 7.23 Hz, 1 H), 8.98-9.03 (m, 1 H), 8.48-8.54 (m, 1 H), 8.44-8.51 (m, 1 H), 7.87-7.94 (m, 2 H), 7.62 (d, J = 8.60 Hz, 1 H), 7.47 (d, J = 8.77 Hz, 1 H), 7.40 (t, J = 8.88 Hz, 2 H), 5.75 (quin, J = 7.13 Hz, 1 H), 4.01 (t, J = 13.15 Hz, 2 H), 3.63 (t, J = 7.34 Hz, 2 H), 2.55 (d, 3 H), 2.18-2.40 (m, 2 H), 1.69 (d, J = 7.23 Hz, 3 H) LCMS (Method5): [MH+] = 528.7 at 1.06 min | Intermediate 52 |
| Example 17 | (R)-8-((3,3-difluoropyrrolidin-1-yl)sulfonyl)-6-(4-fluorophenyl)-N-(1-(5-methyl-1,2,4-oxadiazol-3-yl)ethyl)quinazolin-4-amine 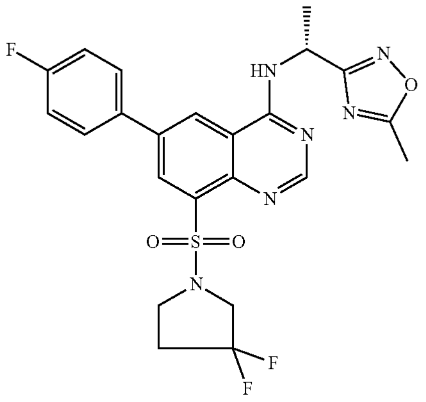 | $^1$H NMR (400 MHz, DMSO-d6) δ ppm 9.05 (br d, J = 7.67 Hz, 1 H), 8.94 (d, J = 1.75 Hz, 1 H), 8.58 (s, 1 H), 8.54 (d, J = 1.75 Hz, 1 H), 7.89 (dd, J = 8.66, 5.37 Hz, 2 H), 7.39 (t, J = 8.77 Hz, 2 H), 5.75 (quin, J = 7.18 Hz, 1 H), 4.03 (t, J = 13.04 Hz, 2 H), 3.65 (t, J = 7.23 Hz, 2 H), 2.54 (s, 3 H), 2.19-2.39 (m, 2 H), 1.65 (d, J = 7.02 Hz, 3 H) LCMS (Method5): [MH+] = 518.8 at 1.15 min | Intermediate 52 |

-continued

| Example No. | Chemical name Structure | Analytical data $^1$H NMR/LC-MS | Reagents |
|---|---|---|---|
| Example 18 | 8-((3,3-difluoropyrrolidin-1-yl)sulfonyl)-6-(4-fluoro-phenyl)-N-(1-(5-methyl-1,3,4-thiadiazol-2-yl)ethyl)-quinazolin-4-amine 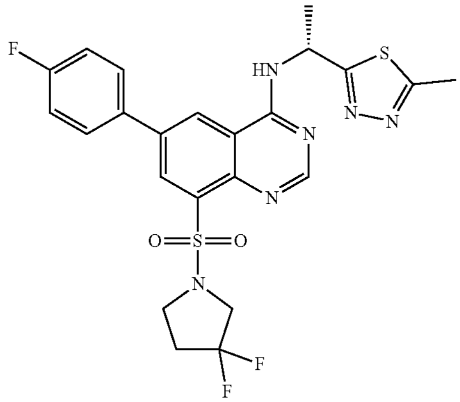 | $^1$H NMR (400 MHz, DMSO-d6) δ ppm 9.20 (d, J = 7.45 Hz, 1 H) 8.92 (d, J = 1.75 Hz, 1 H) 8.63 (s, 1 H) 8.54 (d, J = 1.75 Hz, 1 H) 7.84-7.91 (m, 2 H) 7.39 (t, J = 8.77 Hz, 2 H) 5.97 (m, J = 7.10, 7.10 Hz, 1 H) 3.97-4.07 (m, 2 H) 3.66 (td, J = 7.29, 2.96 Hz, 2 H) 2.62 (s, 3 H) 2.25-2.32 (m, 2 H) 1.78 (d, J = 7.02 Hz, 3 H) LCMS (Method5): [MH+] = 534.97 at 1.11 min | Intermediate 52 |
| Example 19 | (R)-1-((6-(4-fluorophenyl)-4-((1-(6-methylpyridazin-3-yl)ethyl)amino)quinazolin-8-yl)sulfonyl)piperidin-4-ol 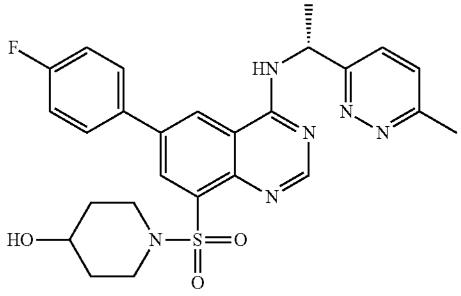 | $^1$H NMR (400 MHz, DMSO-d6) δ ppm 8.94-9.04 (m, 2 H), 8.50 (d, J = 0.88 Hz, 1 H), 8.47 (s, 1 H), 7.90 (dd, J = 8.33, 5.48 Hz, 2 H), 7.62 (d, J = 8.55 Hz, 1 H), 7.46 (d, J = 8.55 Hz, 1 H), 7.39 (t, J = 8.77 Hz, 2 H), 5.74 (quin, J = 7.02 Hz, 1 H), 4.59 (d, J = 3.95 Hz, 1 H), 3.35-3.59 (m, 3 H), 2.91-3.06 (m, 2 H), 2.55 (s, 3 H), 1.64-1.74 (m, 7 H) LCMS (Method5): [MH+] = 522.37 at 1.36 min | Intermediate 53 |
| Example 20 | (R)-1-((6-(4-fluorophenyl)-4-((1-(5-methyl-1,2,4-oxadiazol-3-yl)ethyl)amino)quinazolin-8-yl)-sulfonyl)piperidin-4-ol 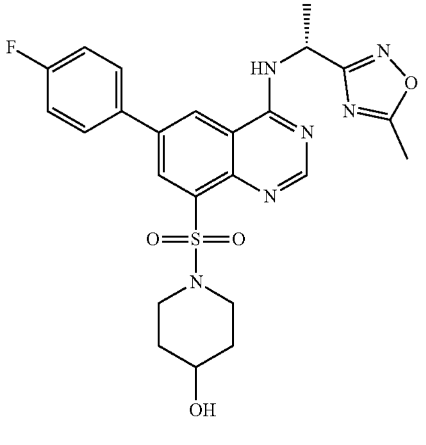 | $^1$H NMR (400 MHz, DMSO-d6) δ ppm 8.99 (br d, J = 7.45 Hz, 1 H), 8.91 (s, 1 H), 8.55 (s, 1 H), 8.51 (s, 1 H), 7.88 (dd, J = 8.33, 5.48 Hz, 2 H), 7.38 (t, J = 8.77 Hz, 2 H), 5.74 (quin, J = 7.18 Hz, 1 H), 4.60 (d, J = 4.17 Hz, 1 H), 3.44-3.61 (m, 3 H), 2.92-3.08 (m, 3 H), 2.53 (s, 3 H), 1.60-1.73 (m, 5 H), 1.26-1.39 (m, 2 H) LCMS (Method5): [MH+] = 512.72 at 1.53 min | Intermediate 53 |

-continued

| Example No. | Chemical name Structure | Analytical data $^1$H NMR/LC-MS | Reagents |
|---|---|---|---|
| Example 21 | (R)-6-(4-fluorophenyl)-N-methyl-4-((1-(6-methylpyridazin-3-yl)ethyl)amino)quinazoline-8-sulfonamide 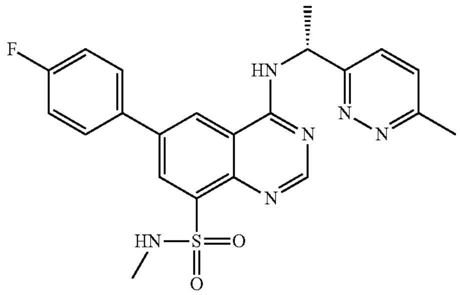 | $^1$H NMR (600 MHz, DMSO-d6) δ ppm 9.13 (d, J = 7.18 Hz, 1 H) 9.04 (d, J = 2.05 Hz, 1 H) 8.52 (s, 1 H) 8.48 (d, J = 2.05 Hz, 1 H) 7.94 (dd, J = 8.78, 5.32 Hz, 2 H) 7.65 (d, J = 8.72 Hz, 1 H) 7.50 (d, J = 8.72 Hz, 1 H) 7.43 (t, J = 8.85 Hz, 2 H) 6.98 (q, J = 5.21 Hz, 1 H) 5.78 (quin, J = 7.12 Hz, 1 H) 2.58 (s, 3 H) 2.42 (d, J = 5.15 Hz, 3 H) 1.73 (d, J = 7.06 Hz, 3 H) LCMS (Method5A): [MH+] = 452.92 at 1.61 min | Intermediate 54 |
| Example 22 | (R)-6-(4-fluorophenyl)-N-methyl-4-((1-(5-methyl-1,2,4-oxadiazol-3-yl)ethyl)amino)quinazoline-8-sulfonamide 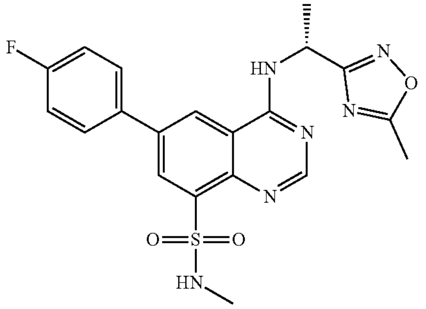 | $^1$H NMR (600 MHz, DMSO-d6) δ ppm 9.11 (d, J = 7.63 Hz, 1 H), 8.97 (d, J = 2.05 Hz, 1 H), 8.60 (s, 1 H), 8.49 (d, J = 2.05 Hz, 1 H), 7.92 (t, J = 6.71 Hz, 2 H), 7.42 (t, J = 8.41 Hz, 2 H), 7.01 (q, J = 5.18 Hz, 1 H), 5.78 (quin, J = 7.19 Hz, 1 H), 2.57 (s, 3 H), 2.44 (d, J = 4.99 Hz, 3 H), 1.69 (d, J = 7.04 Hz, 3 H) LCMS (Method5A): [MH+] = 442.81 at 1.81 min | Intermediate 54 |
| Example 23 | (6-(4-fluorophenyl)-N-methyl-4-((1-(5-methyl-1,3,4-thiadiazol-2-yl)ethyl)amino)quinazoline-8-sulfonamide 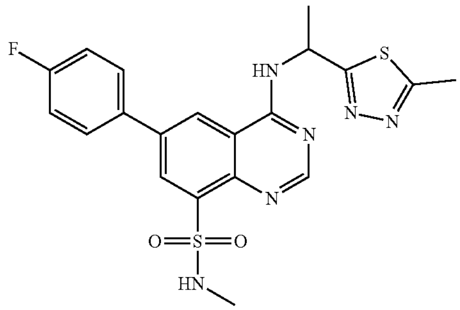 | $^1$H NMR (400 MHz, DMSO-d6) δ ppm 9.22 (d, J = 7.23 Hz, 1 H), 8.90 (d, J = 1.75 Hz, 1 H), 8.62 (s, 1 H), 8.47 (d, J = 1.75 Hz, 1 H), 7.88 (dd, J = 8.66, 5.37 Hz, 2 H), 7.39 (t, J = 8.88 Hz, 2 H), 6.99 (q, J = 5.04 Hz, 1 H), 5.96 (t, J = 7.13 Hz, 1 H), 2.62 (s, 3 H), 2.39-2.43 (m, 3 H), 1.79 (d, J = 7.02 Hz, 3 H) LCMS (Method): [MH+] = 458.02 at 1.02 min | Intermediate 54 |

Example 24

(R)-6-(4-fluorophenyl)-N-(1-(6-methylpyridazin-3-yl)ethyl)-8-(piperazin-1-ylsulfonyl)quinazolin-4-amine

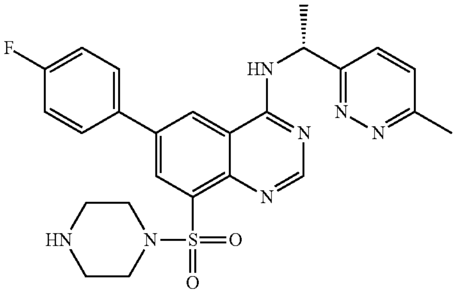 [SMILES: Cc1ccc([C@@H](C)Nc2ncnc3c(S(=O)(=O)N4CCNCC4)cc(-c4ccc(F)cc4)cc23)nn1]

To a solution of benzyl 4-((6-(4-fluorophenyl)-4-hydroxyquinazolin-8-yl)sulfonyl)piperazine-1-carboxylate (100 mg, 0.191 mmol) (Intermediate 55) in dry DMF (5 ml), PyBOP (129 mg, 0.249 mmol) and DIPEA (0.100 ml, 0.574 mmol) were added and the reaction was stirred for 30 min. Then, (R)-1-(6-methylpyridazin-3-yl)ethan-1-amine dihydrochloride (40.2 mg, 0.191 mmol) was added and the reaction was further stirred for 30 min. The solvent was removed and the crude redissolved in dry DCM (5.00 ml) and borontribromide 1 M in DCM (1.914 ml, 1.914 mmol) was added and the reaction was stirred for 1 hr. EtOH (2 mL) was added then volatiles were removed and the crude purified by C18 flash chromatography ((H2O/ACN)) 95:5+ 0.1% HCOOH}:{(ACN/H2O) 95:5+HCOOH 0.1%} from 100:0 to 0:100 affording (R)-6-(4-fluorophenyl)-N-(1-(6-methylpyridazin-3-yl)ethyl)-8-(piperazin-1-ylsulfonyl)quinazolin-4-amine (7 mg, 0.014 mmol, 7.21% yield) as a white solid.

1H NMR (400 MHz, DMSO-d6) δ ppm 9.25 (br d, J=6.58 Hz, 1H), 9.08 (d, J=1.75 Hz, 1H), 8.64 (br s, 2H), 8.54 (d, J=1.75 Hz, 1H), 8.50 (s, 1H), 7.88-7.98 (m, 3H), 7.76 (d, J=8.77 Hz, 1H), 7.41 (t, J=8.77 Hz, 2H), 5.76 (quin, J=6.96 Hz, 1H), 3.46-3.58 (m, 4H), 3.09 (br s, 4H), 2.62 (s, 3H), 1.71 (d, J=7.02 Hz, 3H)

UPLC PRECLI-WI-0183 minute rt 4.29 min 508.18 m/z

The following compounds reported in the table below was prepared via adaptation of the above procedure.

| Example No. | Chemical name Structure | Analytical data $^1H$ NMR/LC-MS |
|---|---|---|
| Example 25 | (R)-6-(4-fluorophenyl)-N-(1-(5-methyl-1,2,4-oxadiazol-3-yl)ethyl)-8-(piperazin-1-ylsulfonyl)-quinazolin-4-amine 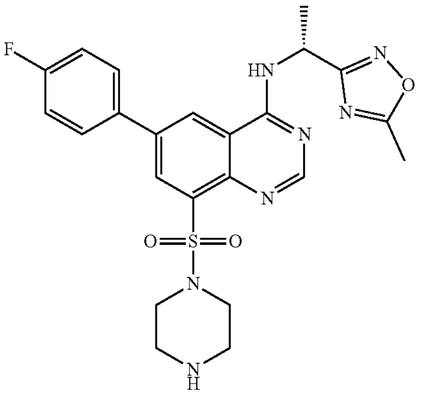 | $^1H$ NMR (600 MHz, DMSO-d6) δ ppm 9.11 (d, J = 7.56 Hz, 1 H), 9.00 (d, J = 2.30 Hz, 1 H), 8.62 (s, 1 H), 8.58 (d, J = 1.97 Hz, 1 H), 7.93 (t, J = 6.62 Hz, 2 H), 7.44 (t, J = 8.71 Hz, 1 H), 5.78-5.82 (m, 1 H), 3.36-3.50 (m, 4 H), 2.97-3.06 (m, 4 H), 2.59 (s, 3 H), 1.70 (d, J = 6.91 Hz, 3 H) LCMS (Method5): [MH+] = 458.02 at 1.02 min |

Intermediate 56

Methyl 4-amino-4'-fluoro-[1,1'-biphenyl]-3-carboxylate

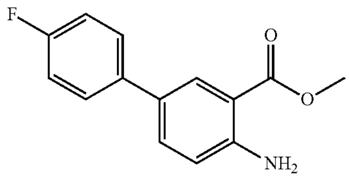 [SMILES: COC(=O)c1cc(-c2ccc(F)cc2)ccc1N]

Nitrogen was bubbled for 5 min through a mixture of methyl 2-amino-5-bromobenzoate (2.00 g, 8.69 mmol), 4-fluorophenylboronic acid, pinacol ester (2.90 g, 12.04 mmol), potassium phosphate tribasic (3.69 g, 17.39 mmol), water (3.5 mL) in N,N-dimethylformamide (10.5 mL), then [1,1'-bis(diphenylphosphino)ferrocene]-dichloropalladium (II) complex with dichloromethane (710 mg, 0.87 mmol) was added. The resulting mixture was heated to 100° C. for 1.25 hours. After return to room temperature, the reaction was diluted with water (100 mL) and diethyl ether (100 mL) and the organic phase was separated. The aqueous phase was extracted further with diethyl ether (100 mL) and then Ethyl acetate (100 mL). The organic phases were combined, washed with water (100 mL), dried over $MgSO_4$ and the solvent was removed in vacuo. The residue was purified by chromatography on silica gel eluting with 5-35% Ethyl acetate in cyclohexane to give the title compound as an off-white solid (2.08 g, 97%).

$^1$H NMR (400 MHz, $CDCl_3$): δ 8.06 (d, J=2.3 Hz, 1H), 7.50-7.44 (m, 3H), 7.08 (dd, J=8.7, 8.7 Hz, 2H), 6.74 (d, J=8.6 Hz, 1H), 5.78 (s, 2H), 3.90 (s, 3H).

Intermediate 57

Methyl 4-amino-4'-fluoro-5-iodo-[1,1'-biphenyl]-3-carboxylate

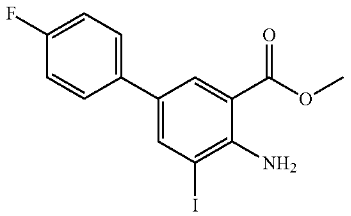 [SMILES: COC(=O)c1cc(-c2ccc(F)cc2)cc(I)c1N]

To a solution of methyl 4-amino-4'-fluoro-[1,1'-biphenyl]-3-carboxylate (2.08 g, 8.48 mmol) in dichloromethane (25 mL) was added bis(pyridine)iodonium tetrafluoroborate (4.73 g, 12.72 mmol) and TFA (2.1 mL, 27.42 mmol). The resulting mixture was stirred at room temperature for 2 days. HPLC analysis showed 70% conversion and further bis (pyridine)iodonium tetrafluoroborate (1.25 g, 3.36 mmol) was added and the stirring was maintained for a further 2.5 hours. The reaction was diluted with dichloromethane (25 mL) and cautiously treated with a solution of $NaHCO_3$ (7 g, 83 mmol) in water (100 mL). The aqueous layer was collected and further extracted with dichloromethane (2×25 mL). The organic phases were combined, washed with an 8% sodium thiosulphate aqueous solution (100 mL), filtered through a hydrophobic frit and the solvent was removed in vacuo. The residue was purified by chromatography on silica gel eluting with 0-25% Ethyl acetate in cyclohexane to give the title compound as an off-white solid (2.71 g, 86%).

$^1$H NMR (400 MHz, $CDCl_3$): δ 8.10-8.07 (m, 1H), 8.04-8.00 (m, 1H), 7.46-7.41 (m, 2H), 7.09 (dd, J=8.6, 8.6 Hz, 2H), 6.48-6.37 (m, 2H), 3.91 (s, 3H).

Intermediate 58

4-amino-4'-fluoro-5-iodo-[1,1'-biphenyl]-3-carboxylic acid

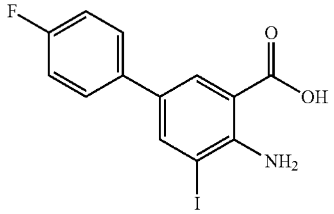 [SMILES: Nc1c(I)cc(-c2ccc(F)cc2)cc1C(=O)O]

To a solution of methyl 4-amino-4'-fluoro-5-iodo-[1,1'-biphenyl]-3-carboxylate (2.59 g, 6.98 mmol) in 1,4-dioxane (25 mL) and water (5 mL) was added lithium hydroxide monohydrate (1.75 g, 41.87 mmol). The mixture was stirred at room temperature for 18 hours. The reaction was diluted with water (100 mL) and diethyl ether (100 mL) and separated. The aqueous phase was acidified with 1N HCl (45 mL) to pH=1 and extracted with dichloromethane (3×50 mL). The organic phases were combined, filtered through a hydrophobic frit and the solvent was removed in vacuo to give the title compound as an off-white solid (2.39 g, 96%).

$^1$H NMR (400 MHz, DMSO): δ 13.17 (s, 1H), 8.18 (d, J=2.0 Hz, 1H), 8.09 (d, J=2.3 Hz, 1H), 7.65 (dd, J=5.4, 8.5 Hz, 2H), 7.27 (dd, J=8.8, 8.8 Hz, 2H), 6.84 (s, 2H).

Intermediate 59

6-(4-fluorophenyl)-8-iodoquinazolin-4(3H)-one

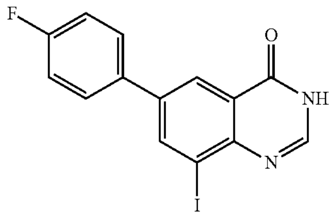 [SMILES: O=c1[nH]cnc2c(I)cc(-c3ccc(F)cc3)cc12]

A solution of 4-amino-4'-fluoro-5-iodo-[1,1'-biphenyl]-3-carboxylic acid (2.39 g, 6.69 mmol) in formamide (4 mL) was heated to 130° C. for 16 hours. After return to room temperature, the reaction was diluted with water (20 mL) and stirred for 20 minutes before filtering. The solid was washed with water (3×5 mL) then 10% MeOH in diethyl ether (3×5 mL) to give the title compound as an off-white solid (2.14 g, 87%).

$^1$H NMR (400 MHz, DMSO): δ 12.57 (s, 1H), 8.66 (s, 1H), 8.36 (s, 1H), 8.28 (s, 1H), 7.89 (dd, J=5.6, 7.8 Hz, 2H), 7.38 (dd, J=8.6, 8.6 Hz, 2H).

Intermediate 60

6-(4-fluorophenyl)-8-(methylthio)quinazolin-4-ol

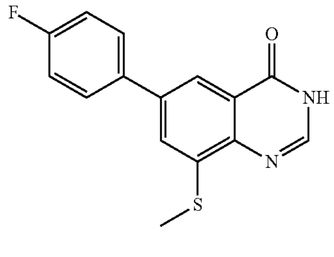 [SMILES: CSc1cc(-c2ccc(F)cc2)cc2c(=O)[nH]cnc12]

To a solution of 6-(4-fluorophenyl)-8-iodoquinazolin-4-ol (0.5 g, 1.366 mmol) in dry DMSO (5 ml), sodium methanethiolate (0.096 g, 1.366 mmol), COPPER (I) IODIDE (0.260 g, 1.366 mmol), cyclohexane-1,2-diamine (0.156 g, 1.366 mmol) were added and the reaction was stirred overnight at 130 C. The crude was directly loaded on C18 cartridge by reverse chromatography ((H2O/ACN)) 95:5+0.1% HCOOH}:{(ACN/H2O) 95:5+HCOOH 0.1%} from 100:0 to 0:100 affording 6-(4-fluorophenyl)-8-(methylthio)quinazolin-4-ol (0.25 g, 0.873 mmol, 63.9% yield) as a brown solid.

LCMS (Method 5): 0.96 min, 286.75 [M+H]+

Example 26

(R)-6-(4-fluorophenyl)-N-(1-(6-methylpyridazin-3-yl)ethyl)-8-(methylthio) quinazolin-4-amine CRDD456-64-1

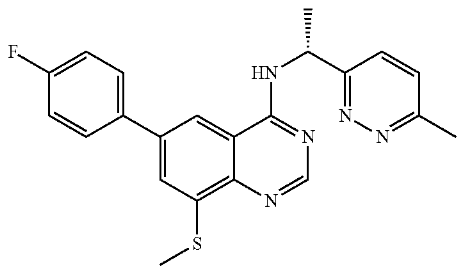 [SMILES: CSc1cc(-c2ccc(F)cc2)cc2c(N[C@H](C)c3ccc(C)nn3)ncnc12]

To a solution of 6-(4-fluorophenyl)-8-(methylthio)quinazolin-4-ol (40 mg, 0.140 mmol) (Intermediate 60) in dry DMF (4 ml), PyBOP (95 mg, 0.182 mmol) and DIPEA (0.073 ml, 0.419 mmol) were added and the reaction was stirred for 30 min. Then, (R)-1-(6-methylpyridazin-3-yl)ethan-1-amine dihydrochloride (29.4 mg, 0.140 mmol) was added and the reaction was further stirred for 30 min. Then, solvent was removed and the crude purified by C18 flash chromatography ((H2O/ACN)) 95:5+0.1% HCOOH}:{(ACN/H2O) 95:5+HCOOH 0.1%} from 100:0 to 0:100 affording (R)-6-(4-fluorophenyl)-N-(1-(6-methylpyridazin-3-yl)ethyl)-8-(methylthio)quinazolin-4-amine (6 mg, 0.015 mmol, 10.59% yield) as a white solid.

$^1H$ NMR (600 MHz, DMSO-d6) δ ppm 8.77 (d, J=7.56 Hz, 1H), 8.45 (d, J=1.64 Hz, 1H), 8.40 (s, 1H), 7.96 (t, J=6.54 Hz, 2H), 7.68 (d, J=1.64 Hz, 1H), 7.61 (d, J=8.88 Hz, 1H), 7.49 (d, J=8.55 Hz, 1H), 7.39 (t, J=8.88 Hz, 2H), 5.74-5.79 (m, 1H), 2.58 (s, 3H), 2.56 (s, 3H), 1.71 (d, J=7.23 Hz, 3H)

UPLC PRECLI-WI-0183 minute rt 5.98 min 406.23 m/z

Intermediate 61

6-(4-fluorophenyl)-8-(methylsulfinyl)quinazolin-4-ol CRDD456-65-1

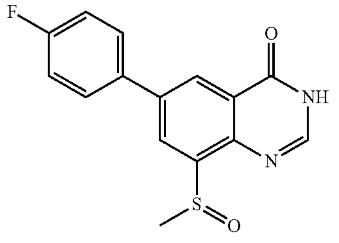 [SMILES: CS(=O)c1cc(-c2ccc(F)cc2)cc2c(=O)[nH]cnc12]

To a solution of 6-(4-fluorophenyl)-8-(methylthio)quinazolin-4-ol (100 mg, 0.349 mmol) in dry DCM (5 ml), mCPBA (60.3 mg, 0.349 mmol) was added and the reaction was stirred for 1 hr. Then, the reaction was diluted in DCM (20 mL) and washed with $Na_2SO_3$ saturated aqueous solution (20 mL) and $NaHCO_3$ saturated aqueous solution (20 mL). The organic phase was dried over $Na_2SO_4$, filtered and the solvent was removed under reduced pressure. The crude was purified by C18 flash chromatography ((H2O/ACN)) 95:5+0.1% HCOOH}:{(ACN/H2O) 95:5+HCOOH 0.1%} from 100:0 to 0:100 affording 6-(4-fluorophenyl)-8-(methylsulfinyl)quinazolin-4-ol (55 mg, 0.182 mmol, 52.1% yield)

LCMS (Method 5): 1.16 min, 302.75 [M+H]+

Example 27

6-(4-fluorophenyl)-N—((R)-1-(6-methylpyridazin-3-yl)ethyl)-8-(methylsulfinyl) quinazolin-4-amine

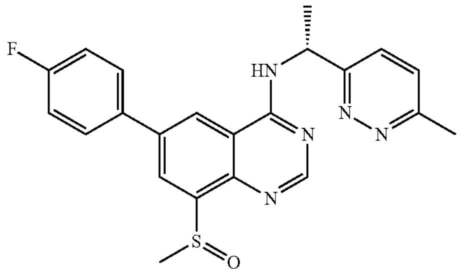 [SMILES: Cc1ccc([C@@H](C)Nc2ncnc3c(S(C)=O)cc(-c4ccc(F)cc4)cc23)nn1]

To a solution of 6-(4-fluorophenyl)-8-(methylsulfinyl)quinazolin-4-ol (50 mg, 0.165 mmol) (Intermediate 61) in dry DMF (4 ml), PyBOP (112 mg, 0.215 mmol) and DIPEA (0.087 ml, 0.496 mmol) were added and the reaction was stirred for 30 min. Then, (R)-1-(6-methylpyridazin-3-yl)ethan-1-amine dihydrochloride (38.2 mg, 0.182 mmol) was added and the reaction was further stirred for 30 min. Then, solvent was removed and the crude purified by C18 flash chromatography ((H2O/ACN)) 95:5+0.1% HCOOH}:{(ACN/H2O) 95:5+HCOOH 0.1%} from 100:0 to 0:100 affording 6-(4-fluorophenyl)-N—((R)-1-(6-methylpyridazin-3-yl)ethyl)-8-(methylsulfinyl)quinazolin-4-amine (5 mg, 0.012 mmol, 7.17% yield) as a white solid.

1H NMR (600 MHz, DMSO-d6) δ ppm 9.05-9.10 (m, 1H), 8.93 (dd, J=5.09, 2.06 Hz, 1H), 8.45 (d, J=5.22 Hz, 1H), 8.34 (d, J=1.92 Hz, 1H), 7.95 (t, J=6.73 Hz, 2H), 7.65 (d, J=8.80 Hz, 1H), 7.50 (d, J=8.52 Hz, 1H), 7.44 (t, J=8.80 Hz, 2H), 5.75-5.81 (m, 1H), 2.90-2.93 (m, 3H), 2.58-2.59 (m, 3H), 1.73 (d, J=7.01, 3H)

UPLC PRECLI-WI-0183 minuti rt 5.16 min 422.24 m/z

Intermediate 61a (R)-6-(4-fluorophenyl)-8-iodo-N-(1-(2-(trifluoromethyl)pyrimidin-5-yl)ethyl)quinazolin-4-amine

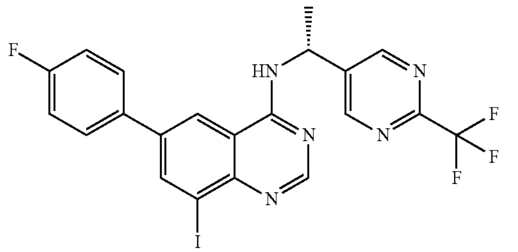 [SMILES: C[C@@H](Nc1ncnc2c(I)cc(-c3ccc(F)cc3)cc12)c1cnc(C(F)(F)F)nc1]

To a solution of 6-(4-fluorophenyl)-8-iodoquinazolin-4-(3H)-one (1.14 g, 3.11 mmol) in N,N-dimethylformamide (10 mL) was successively added (benzotriazol-1-yloxy) tripyrrolidinophosphonium hexafluorophosphate (2.03 g, 1.25 mmol) and di-isopropylethylamine (2.7 mL, 15.57 mmol). The resulting mixture was heated to 45° C. for one hour then (R)-1-(2-(trifluoromethyl)pyrimidin-5-yl)ethan-1-amine hydrochloride (0.96 g, 4.2 mmol) was added and the heating was maintained at 45° C. for 2 hours. After return to room temperature, the mixture was diluted with ethyl acetate (75 mL) and water (175 mL). The organic phase was washed with brine (2×20 mL), passed through a hydrophobic frit and the solvent was removed in vacuo. The residue was purified by chromatography on silica gel eluting with 0-15% ethyl acetate in dichloromethane to give the title compound as an off-white solid (1.27 g, 75%).

$^{1}$H NMR (400 MHz, DMSO): δ 9.18 (s, 2H), 8.88 (d, J=6.9 Hz, 1H), 8.71 (d, J=1.8 Hz, 1H), 8.67 (d, J=1.8 Hz, 1H), 8.51 (s, 1H), 7.95-7.90 (m, 2H), 7.40 (dd, J=8.9, 8.9 Hz, 2H), 5.73-5.67 (m, 1H), 1.75 (d, J=7.2 Hz, 3H).

The following compound reported in the table below was prepared via adaptation of the above procedure using the appropriate amine.

Example 28

(R)-6-(4-fluorophenyl)-N-(1-(6-methylpyridazin-3-yl)ethyl)-8-(oxetan-3-ylthio)quinazolin-4-amine

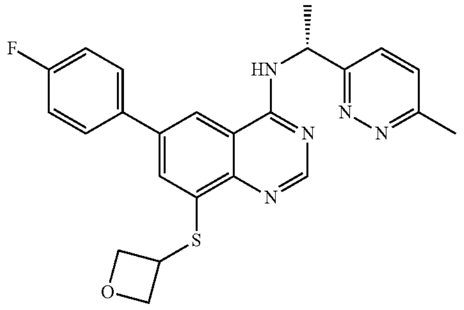 [SMILES: Cc1ccc([C@@H](C)Nc2ncnc3c(SC4COC4)cc(-c4ccc(F)cc4)cc23)nn1]

To a solution of (R)-6-(4-fluorophenyl)-8-iodo-N-(1-(6-methylpyridazin-3-yl)ethyl)quinazolin-4-amine (400 mg, 0.824 mmol) (Intermediate 61b) in dry, oxetane-3-thiol (74.3 mg, 0.824 mmol), COPPER (I) IODIDE (7.85 mg, 0.041 mmol), cyclohexane-1,2-diamine (0.020 ml, 0.165 mmol) and potassium phosphate (525 mg, 2.473 mmol) were added and the reaction was stirred overnight at 130 C. The reaction was directly loaded on C18 cartridge by reverse chromatography ((H2O/ACN)) 95:5+0.1% HCOOH}:{(ACN/H2O) 95:5+HCOOH 0.1%} from 100:0 to 0:100 affording (R)-6-(4-fluorophenyl)-N-(1-(6-methylpyridazin-3-yl)ethyl)-8-(oxetan-3-ylthio)quinazolin-4-amine (100 mg, 0.223 mmol, 27.1% yield) as a brown solid.

UPLC PRECLI-WI-0183 minuti rt 4.22 min 448.25 m/z $^{1}$H NMR (600 MHz, DMSO-d4) δ ppm 8.13 (dd, J=2.14, 1.48 Hz, 1H), 7.90 (s, 1H), 7.78 (dd, J=12.00, 8.71 Hz, 1H), 7.70-7.75 (m, 2H), 7.67-7.69 (m, 1H), 7.49 (dd, J=8.88, 2.96 Hz, 1H), 7.30-7.34 (m, 2H), 5.68-5.75 (m, 1H), 5.35-5.41 (m, 1H), 4.19-4.28 (m, 2H), 3.50-3.66 (m, 2H), 2.58 (s, 3H), 1.45 (dd, J=6.74, 4.77 Hz, 3H).

| Example No. | Chemical name Structure | Analytical data $^{1}$H NMR LC-MS |
|---|---|---|
| Intermediate 61b | 6-(4-fluorophenyl)-8-iodo-N-((6-methylpyridazin-3-yl)-methyl)quinazolin-4-amine 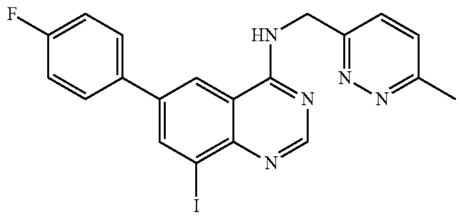 | LCMS (Method 5): 0.96 min, m/z 472.0. $^{1}$H NMR (400 MHz, DMSO-d6) δ ppm 9.26 (br t, J = 5.62 Hz, 1 H), 8.64 (s, 2 H), 8.47 (s, 1 H), 7.88 (br dd, J = 8.60, 5.51 Hz, 2 H), 7.53 (d, J = 8.60 Hz, 1 H), 7.45 (d, J = 8.60 Hz, 1 H), 7.34 (br t, J = 8.71 Hz, 2 H), 5.02 (br d, J = 5.29 Hz, 2 H), 2.56 (s, 3 H). |

Example 29

6-(4-fluorophenyl)-N—((R)-1-(6-methylpyridazin-3-yl)ethyl)-8-(oxetan-3-ylsulfinyl)quinazolin-4-amine

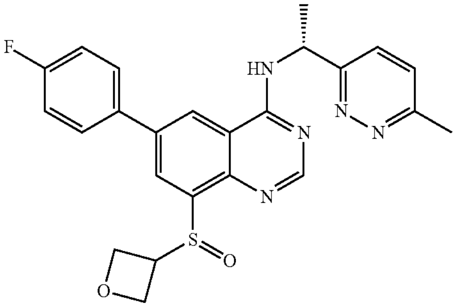 [SMILES: Cc1ccc([C@@H](C)Nc2ncnc3c(S(=O)C4COC4)cc(-c4ccc(F)cc4)cc23)nn1]

To a solution of (R)-6-(4-fluorophenyl)-N-(1-(6-methylpyridazin-3-yl)ethyl)-8-(oxetan-3-ylthio)quinazolin-4-amine (100 mg, 0.223 mmol) (Example 28) in dry DCM (5 ml), mCPBA (38.6 mg, 0.223 mmol) was added and the reaction was stirred for 1 h. Then, the reaction was diluted in DCM (20 mL) and washed with $Na_2SO_3$ sat. sol. (20 mL) and $NaHCO_3$ saturated aqueous solution (20 mL). The organic phase was dried over sodium sulfate, filtered and concentrated under reduced pressure. The crude was purified by C18 flash chromatography ((H2O/ACN)) 95:5+0.1% HCOOH}:{(ACN/H2O) 95:5+HCOOH 0.1%} from 100:0 to 0:100 affording 6-(4-fluorophenyl)-N—((R)-1-(6-methylpyridazin-3-yl)ethyl)-8-(oxetan-3-ylsulfinyl)quinazolin-4-amine (10 mg, 0.022 mmol, 9.65% yield) as yellow pale solid.

LCMS (Method 5): 0.65 min, 467.27 [M+H]+

$^1$H NMR (600 MHz, DMSO-d4) δ ppm 8.59 (br s, 1H), 8.39 (d, J=1.65 Hz, 1H), 8.00-8.08 (m, 1H), 7.75-7.89 (m, 3H), 7.50 (br d, J=8.52 Hz, 1H), 7.36 (t, J=8.25 Hz, 2H), 5.71-5.78 (m, 1H), 5.36-5.41 (m, 1H), 4.18-4.22 (m, 2H), 3.58-3.80 (m, 2H), 2.62 (s, 3H), 1.47 (dd, J=6.74, 3.16 Hz, 3H).

Intermediate 62

(R)-6-(4-Fluorophenyl)-8-((tetrahydro-2H-pyran-4-yl)oxy)-N-(1-(2-(trifluoromethyl)pyrimidin-5-yl)ethyl)quinazolin-4-amine

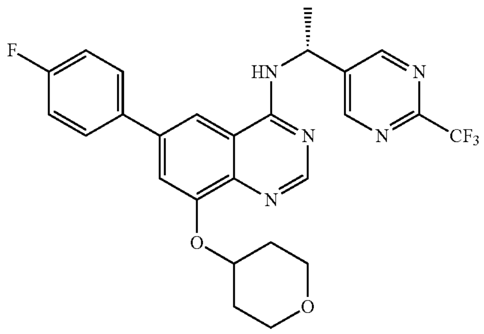 [SMILES: C[C@@H](Nc1ncnc2c(OC3CCOCC3)cc(-c3ccc(F)cc3)cc12)c1cnc(C(F)(F)F)nc1]

Nitrogen was bubbled for 5 min through a mixture of (R)-6-(4-fluorophenyl)-4-((1-(2-(trifluoromethyl)pyrimidin-5-yl)ethyl)amino)quinazolin-8-ol (40 mg, 0.01 mmol) (Intermediate 10), tetrahydro-4-pyranol (10 mg, 0.102 mmol) and cyanomethyltributylphosphorane (1 M in toluene, 0.14 mL, 0.14 mmol) in toluene (3.0 mL). The mixture was heated to 100° C. for 72 hours. After return to room temperature, the solvent was removed in vacuo. The residue was purified by preparative HPLC to give the title compound (17 mg, 38%) as an off white solid.

$^1$H NMR (400 MHz, DMSO): δ 9.18 (s, 2H), 8.64 (d, J=7.0 Hz, 1H), 8.44 (s, 1H), 8.23 (d, J=1.6 Hz, 1H), 7.94-7.89 (m, 2H), 7.65 (d, J=1.6 Hz, 1H), 7.39 (dd, J=8.8, 8.8 Hz, 2H), 5.71-5.66 (m, 1H) 5.02-4.94 (m, 1H), 3.96-3.88 (m, 2H), 3.51 (dd, J=9.7, 9.7 Hz, 2H), 2.07-2.00 (m, 2H), 1.74 (d, J=7.0 Hz, 5H). LCMS (Method 3): [MH+]=514 at 3.79 min.

The following compounds reported in the table below were prepared according to the same procedure described for the preparation of (R)-6-(4-Fluorophenyl)-8-((tetrahydro-2H-pyran-4-yl)oxy)-N-(1-(2-(trifluoromethyl)pyrimidin-5-yl)ethyl)quinazolin-4-amine:

| Example No. | Chemical name Structure | Analytical data $^1$H NMR LC-MS |
|---|---|---|
| Example 30 | (1-((S)-3-((6-(4-fluorophenyl)-4-(((R)-1-(2-(trifluoromethyl)-pyrimidin-5-yl)ethyl)amino)quinazolin-8-yl)oxy)pyrrolidin-1-yl)ethan-1-one 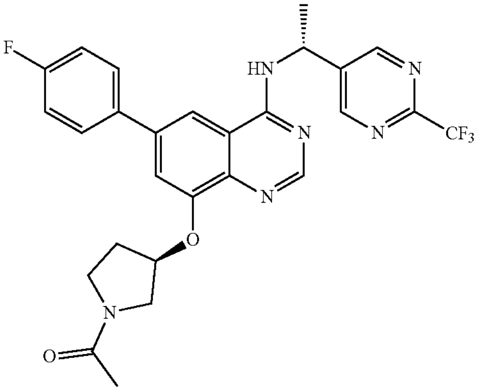 | $^1$H NMR (400 MHz, DMSO): δ 9.17 (s, 2 H), 8.68 (d, J = 6.8 Hz, 1 H), 8.43 (s, 1 H), 8.27 (dd, J = 2.3, 2.3 Hz, 1H), 7.97-7.91 (m, 2 H), 7.63 (d, J = 1.5 Hz, 1 H), 7.60 (d, J = 1.5 Hz, 1 H), 7.40 (dd, J = 8.8, 8.8 Hz, 2 H), 5.71-5.66 (m, 1 H), 5.51 (d, J = 3.3 Hz, 1 H), 5.44 (d, J = 3.0 Hz, 1 H), 3.87 (dd, J = 4.5, 11.7 Hz, 1 H), 3.72-3.55 (m, 3 H), 2.29-2.22 (m, 1 H), 2.18-2.11 (m, 1 H), 1.98 (d, J = 18.3 Hz, 3 H), 1.74 (d, J = 7.0 Hz, 3 H). LCMS (Method 4): [MH+] = 541 at 3.52 min. |

-continued

| Example No. | Chemical name Structure | Analytical data $^1H$ NMR LC-MS |
|---|---|---|
| Example 31 | (1-((R)-3-((6-(4-fluorophenyl)-4-(((R)-1-(2-(trifluoromethyl)-pyrimidin-5-yl)ethyl)amino)quinazolin-8-yl)oxy)pyrrolidin-1-yl)ethan-1-one 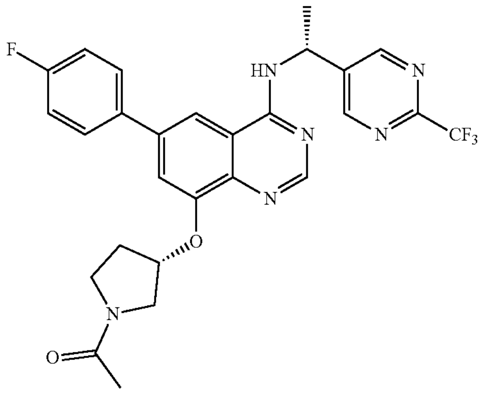 | $^1H$ NMR (400 MHz, DMSO): δ 9.18 (s, 2 H), 8.69 (d, J = 6.9 Hz, 1 H), 8.43 (s, 1 H), 8.27 (dd, J = 2.1, 2.1 Hz, 1 H), 7.97-7.91 (m, 2 H), 7.63 (d, J = 1.6 Hz, 1 H), 7.60 (d, J = 1.5 Hz, 1 H), 7.40 (dd, J = 8.8, 8.8 Hz, 2 H), 5.72-5.64 (m, 1 H), 5.51 (d, J = 3.1 Hz, 1 H), 5.44 (d, J = 3.1 Hz, 1 H), 3.87 (dd, J = 4.5, 11.7 Hz, 1 H), 3.64 (s, 3 H), 2.27-2.21 (m, 1 H), 2.17-2.09 (m, 1 H), 1.98 (d, J = 14.9 Hz, 3 H), 1.74 (d, J = 7.0 Hz, 3 H). LCMS (Method 4): [MH+] = 541 at 3.57 min. |
| Example 32 | N-((1S,4s)-4-((6-(4-fluorophenyl)-4-(((R)-1-(2-(trifluoro-methyl)pyrimidin-5-yl)ethyl)amino)quinazolin-8-yl)oxy)-cyclohexyl)acetamide 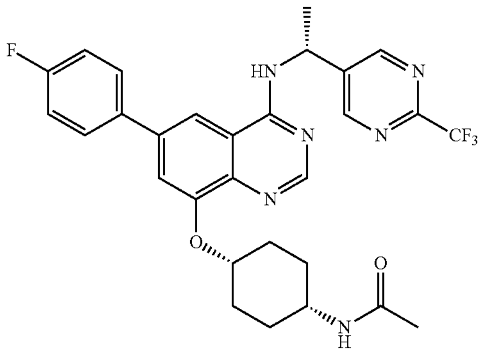 | $^1H$ NMR (400 MHz, DMSO): δ 9.18 (s, 2 H), 8.63 (d, J = 7.0 Hz, 1 H), 8.44 (s, 1 H), 8.21 (d, J = 1.4 Hz, 1 H), 7.93-7.86 (m, 3 H), 7.57 (d, J = 1.3 Hz, 1 H), 7.39 (dd, J = 8.9, 8.9 Hz, 2 H), 5.71-5.65 (m, 1 H), 4.95-4.93 (m, 1 H), 3.72-3.69 (m, 1 H), 1.98 (dd, J = 4.5, 9.7 Hz, 2 H), 1.81 (s, 3 H), 1.76-1.60 (m, 6 H), 1.46-1.33 (m, 3 H). LCMS (Method 4): [MH+] = 569 at 3.68 min. |
| Example 33 | 6-(4-fluorophenyl)-8-((1-(2,2,2-trifluoroethyl)pyrrolidin-3-yl)oxy)-N-((R)-1-(2-(trifluoromethyl)pyrimidin-5-yl)ethyl)-quinazolin-4-amine 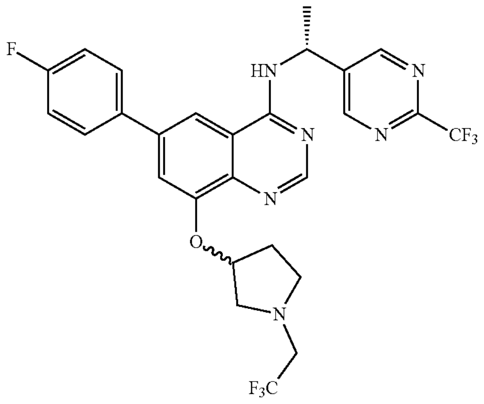 | $^1H$ NMR (400 MHz, DMSO): δ 9.17 (s, 2 H), 8.65 (d, J = 7.0 Hz, 1 H), 8.43 (s, 1 H), 8.21 (s, 1 H), 7.92 (dd, J = 5.5, 8.8 Hz, 2 H), 7.47 (s, 1 H), 7.40 (dd, J = 8.8, 8.8 Hz, 2 H), 5.71-5.65 (m, 1 H), 5.29 (dd, J = 6.5, 6.5 Hz, 1 H), 3.40 (s, 2 H), 3.20 (dd, J = 6.0, 10.7 Hz, 1 H), 3.02-2.94 (m, 2 H), 2.75 (dd, J = 8.0, 14.6 Hz, 1 H), 2.41-2.31 (m, 1 H), 2.02-1.93 (m, 1 H), 1.74 (d, J = 7.2 Hz, 3 H). LCMS (Method 3): [MH+] = 581 at 5.25 min. |

-continued

| Example No. | Chemical name Structure | Analytical data $^1$H NMR LC-MS |
|---|---|---|
| Example 34 | 3-((6-(4-fluorophenyl)-4-(((R)-1-(2-(trifluoromethyl)-pyrimidin-5-yl)ethyl)amino)quinazolin-8-yl)oxy)-pyrrolidin-2-one 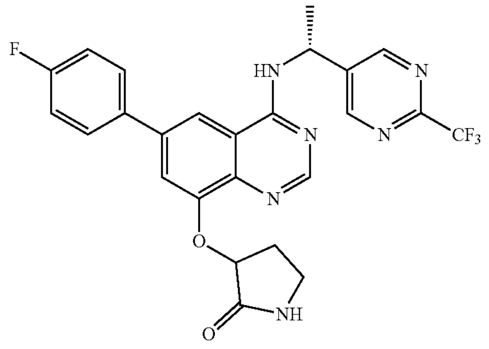 | $^1$H NMR (400 MHz, DMSO): δ 9.22 (s, 2 H), 8.74-8.73 (m, 1 H), 8.41 (s, 1 H), 8.26 (s, 1 H), 8.08 (s, 1 H), 7.96-7.92 (m, 2 H), 7.46 (dd, J = 8.9, 8.9 Hz, 2 H), 5.85 (dd, J = 6.7, 6.7 Hz, 1 H), 5.54 (dd, J = 7.3, 7.3 Hz, 1 H), 3.33-3.26 (m, 2 H), 2.70-2.61 (m, 1 H), 2.29-2.19 (m, 1 H), 1.81 (d, J = 7.2 Hz, 3 H). LCMS (Method 4): [MH+] = 513 at 3.55 min. |
| Example 35 | (R)-1-(4-((6-(4-fluorophenyl)-4-((1-2-(trifluoromethyl)-pyrimidin-5-yl)ethyl)amino)quinazolin-8-yl)oxy)piperidin-1-yl)ethan-1-one 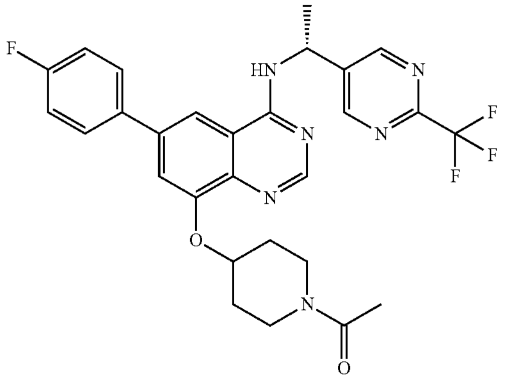 | $^1$H NMR (400 MHz, DMSO): δ 9.18 (s, 2 H), 8.65 (d, J = 7.0 Hz, 1 H), 8.44 (s, 1 H), 8.25 (d, J = 1.5 Hz, 1 H), 7.95-7.90 (m, 2 H), 7.69 (d, J = 1.3 Hz, 1 H), 7.40 (dd, J = 8.8, 8.8 Hz, 2 H), 5.71-5.66 (m, 1 H), 5.07-5.00 (m, 1 H), 3.89-3.82 (m, 1 H), 3.77-3.71 (m, 1 H), 3.36 (d, J = 56.9 Hz, 2 H), 2.03 (s, 3 H), 2.02-1.97 (m, 1 H), 1.96-1.89 (m, 1 H), 1.76-1.72 (m, 4 H), 1.70-1.59 (m, 1 H). LCMS (Method 3): $[MH^+]$ = 555 at 4.77 min. |
| Example 36 | | $^1$H NMR (400 MHz, DMSO): δ 9.17 (s, 2 H), 8.63 (d, J = 6.9 Hz, 1 H), 8.44-8.44 (m, 1 H), 8.22 (d, J = 1.6 Hz, 1 H), 7.91 (ddd, J = 3.2, 5.4, 12.1 Hz, 2 H), 7.61 (d, J = 1.5 Hz, 1 H), 7.42-7.37 (m, 2 H), 5.72-5.64 (m, 1 H), 4.86-4.79 (m, 1 H), 3.22 (q, J = 10.2 Hz, 2 H), 2.93 (dd, J = 6.0, 11.2 Hz, 2 H), 2.01-1.97 (m, 2 H), 1.77-1.72 (m, 4 H). LCMS (Method 3): $[MH^+]$ = 595 at 4.77 min. |

-continued

| Example No. | Chemical name Structure | Analytical data $^1H$ NMR LC-MS |
|---|---|---|
| Example 37 | (R)-3-(((6-(4-fluorophenyl)-4-((1-(2-(trifluoromethyl)-pyrimidin-5-yl)ethyl)amino)quinazolin-8-yl)oxy)methyl)-oxetan-3-ol 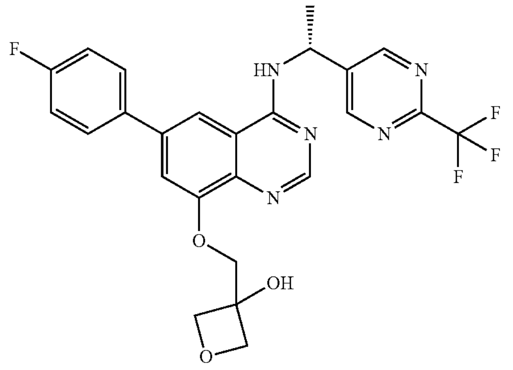 | $^1H$ NMR (400 MHz, DMSO): δ 9.18 (s, 2H), 8.66 (d, J = 6.9 Hz, 1 H), 8.45 (s, 1 H), 8.26 (d, J = 1.3 Hz, 1 H), 7.95 (dd, J = 5.5, 8.8 Hz, 2 H), 7.69 (d, J = 1.4 Hz, 1 H), 7.40 (dd, J = 8.8, 8.8 Hz, 2 H), 6.25 (s, 1 H), 5.72-5.66 (m, 1 H), 4.57 (dd, J = 6.7, 25.1 Hz, 4 H), 4.41 (s, 2 H), 1.75 (d, J = 7.2 Hz, 3 H). LCMS (Method 3): [MH$^+$] = 516 at 4.51 min. |

Intermediate 63

(R)-8-((3-(benzyloxy)isoxazol-5-yl)methoxy)-6-(4-fluorophenyl)-N-(1-(2-(trifluoromethyl)pyrimidin-5-yl)ethyl)quinazolin-4-amine

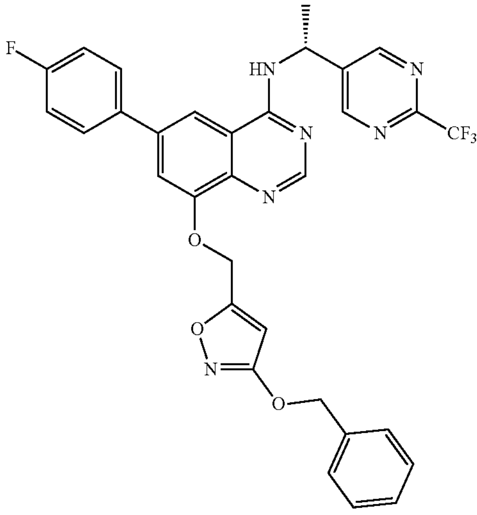 [SMILES: C[C@@H](Nc1ncnc2c(OCc3cc(OCc4ccccc4)no3)cc(-c3ccc(F)cc3)cc12)c1cnc(C(F)(F)F)nc1]

Nitrogen was bubbled for 5 min through a mixture of (R)-6-(4-fluorophenyl)-4-((1-(2-(trifluoromethyl)pyrimidin-5-yl)ethyl)amino)quinazolin-8-ol (95 mg, 0.221 mmol), (3-(benzyloxy)isoxazol-5-yl)methanol (75 mg, 0.265 mmol) and cyanomethyltributyl-phosphorane (64 mg, 0.265 mmol) in toluene (4.0 mL). The mixture was heated to 100° C. for 72 hours. After return to room temperature, the solvent was removed in vacuo. The residue was purified by preparative HPLC to give the title compound (140 mg) as an off white solid which was taken on to the next step without further purification.

Example 38

(R)-5-(((6-(4-fluorophenyl)-4-((1-(2-(trifluoromethyl)pyrimidin-5-yl)ethyl)amino)quinazolin-8-yl)oxy)methyl)isoxazol-3-ol

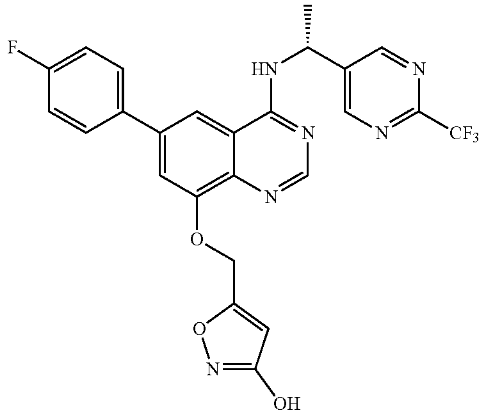 [SMILES: C[C@@H](Nc1ncnc2c(OCc3cc(O)no3)cc(-c3ccc(F)cc3)cc12)c1cnc(C(F)(F)F)nc1]

To a mixture of (R)-8-((3-(benzyloxy)isoxazol-5-yl)methoxy)-6-(4-fluorophenyl)-N-(1-(2-(trifluoromethyl)pyrimidin-5-yl)ethyl)quinazolin-4-amine (140 mg, 0.227 mmol) in acetic acid (1 mL) was added a 48% solution of hydrogen bromide in water (2 mL). The mixture was heated at 100° C. for 2 hours. After return to room temperature, the reaction was evaporated in vacuo and the residue was purified by preparative HPLC to give the tittle compound (3.2 mg, 2.7% over two steps) as an off-white solid.

$^1H$ NMR (400 MHz, DMSO): δ 9.18 (s, 2H), 8.69 (d, J=6.9 Hz, 1H), 8.43 (s, 1H), 8.28 (d, J=1.4 Hz, 1H), 7.97-7.92 (m, 2H), 7.71 (d, J=1.4 Hz, 1H), 7.41 (dd, J=8.9, 8.9 Hz, 2H), 6.16 (s, 1H), 5.72-5.66 (m, 1H), 5.41 (s, 2H), 1.74 (d, J=7.2 Hz, 3H). OH not observed. LCMS (Method 3): [MH+]=527 at 3.60 min.

Intermediate 64

Tert-butyl (R)-2-((6-(4-fluorophenyl)-4-((1-(2-(trifluoromethyl)pyrimidin-5-yl)ethyl)amino)quinazolin-8-yl)oxy)acetate

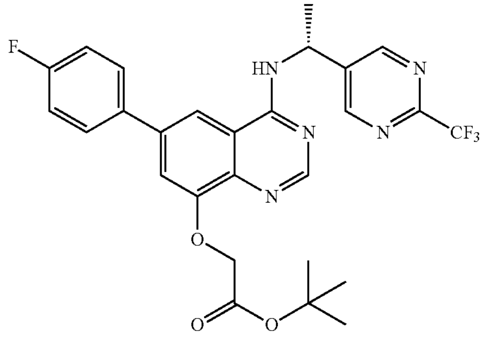 [SMILES: C[C@@H](Nc1ncnc2c(OCC(=O)OC(C)(C)C)cc(-c3ccc(F)cc3)cc12)c1cnc(C(F)(F)F)nc1]

Tert-butyl 2-bromoacetate (0.057 ml, 0.384 mmol) was added to a stirred mixture of (R)-6-(4-fluorophenyl)-4-((1-(2-(trifluoromethyl)pyrimidin-5-yl)ethyl)amino) quinazolin-8-ol (150 mg, 0.349 mmol) (Intermediate 10) and potassium carbonate (155 mg, 1.122 mmol) in DMF (3 ml). Stirring went on at rt for 1 h, then the reaction mixture was diluted with EtOAC and washed with brine (2×). The organic layer was dried over sodium sulfate, filtered and concentrated under reduced pressure. Purification by chromatography (Biotage Isolera, 10 g KP-Sil cartridge, gradient elution from 0 to 50% EtOAc in dichloromethane in 15 CV) yielded tert-butyl (R)-2-((6-(4-fluorophenyl)-4-((1-(2-(trifluoromethyl)pyrimidin-5-yl)ethyl)amino)quinazolin-8-yl) oxy)acetate (149 mg, 0.274 mmol, 78% yield) a white powder.

LCMS (Method 5): 0.97 min, m/z 544.2 [M+H]+.

Intermediate 65

(R)-2-((6-(4-fluorophenyl)-4-((1-(2-(trifluoromethyl) pyrimidin-5-yl)ethyl)amino)quinazolin-8-yl)oxy) acetic acid

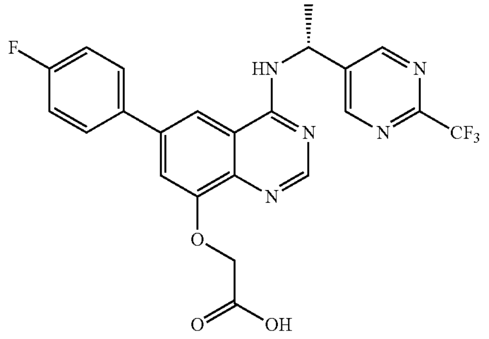 [SMILES: C[C@@H](Nc1ncnc2c(OCC(=O)O)cc(-c3ccc(F)cc3)cc12)c1cnc(C(F)(F)F)nc1]

Tert-butyl (R)-2-((6-(4-fluorophenyl)-4-((1-(2-(trifluoromethyl)pyrimidin-5-yl)ethyl)amino)quinazolin-8-yl)oxy) acetate (149 mg, 0.274 mmol) was dissolved in TFA (2 mL). Stirring went on at rt for 16 h, then volatiles were removed under reduced pressure. Trituration in diethyl ether yielded (R)-2-((6-(4-fluorophenyl)-4-((1-(2-(trifluoromethyl)pyrimidin-5-yl)ethyl)amino)quinazolin-8-yl)oxy)acetic acid (134 mg, 0.275 mmol, 100% yield) as a pale pink powder.

LCMS (Method 5): 0.81 min, m/z 488.1 [M+H]+, $^1$H NMR (400 MHz, DMSO-d6) δ ppm 9.22 (bs, 1H), 9.16 (s, 2H), 8.55 (s, 1H), 8.29 (s, 1H), 7.87 (dd, J=8.66, 5.37 Hz, 2H), 7.65 (br s, 1H), 7.38 (t, J=8.77 Hz, 2H), 5.75 (quin, J=6.63 Hz, 1H), 5.07 (s, 2H), 1.73 (d, J=7.02 Hz, 3H).

Example 40

(R)-2-((6-(4-fluorophenyl)-4-((1-(2-(trifluoromethyl) pyrimidin-5-yl)ethyl)amino)quinazolin-8-yl)oxy)-N-(phenylsulfonyl)acetamide

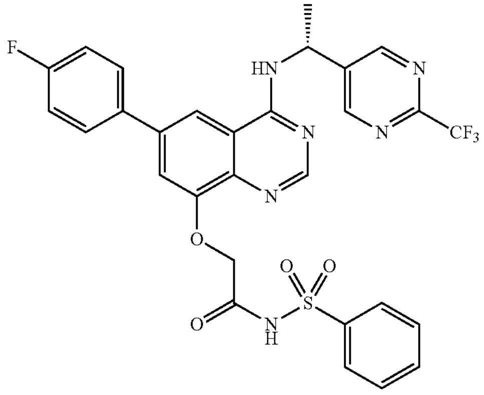 [SMILES: C[C@@H](Nc1ncnc2c(OCC(=O)NS(=O)(=O)c3ccccc3)cc(-c3ccc(F)cc3)cc12)c1cnc(C(F)(F)F)nc1]

EDCI (67.8 mg, 0.354 mmol) was added to a stirred solution of (R)-2-((6-(4-fluorophenyl)-4-((1-(2-(trifluoromethyl)pyrimidin-5-yl)ethyl)amino)quinazolin-8-yl)oxy)acetic acid (115 mg, 0.236 mmol) (Intermediate 65), DIPEA (205 μl, 1.180 mmol), benzenesulfonamide (55.6 mg, 0.354 mmol), DMAP (43.2 mg, 0.354 mmol) in DMF (2 mL). Stirring went on for 16 h at rt. The reaction mixture was diluted with EtOAc, then formic acid (100 μl, 2.65 mmol) was added. The organic layer was washed with brine, dried over sodium solfate, filtered and concentrated under reduced pressure. Purification by column chromatography (Biotage Isolera, 30 g C18 cartridge, gradient elution from 0 to 60% B in A; A: water/acetonitrile 95:5+0.1% HCOOH, B: acetonitrile:water 95:5+0.1% HCOOH) yielded (R)-2-((6-(4-fluorophenyl)-4-((1-(2-(trifluoromethyl)pyrimidin-5-yl) ethyl)amino)quinazolin-8-yl)oxy)-N-(phenylsulfonyl)acetamide (97.3 mg, 0.155 mmol, 65.8% yield) as an off-white powder.

LCMS (Method 5): 0.96 min, 627.2 [M+H]+

$^1$H NMR (400 MHz, DMSO-d6) δ ppm 9.14 (s, 2H), 8.97 (br s, 1H), 8.44 (s, 1H), 8.24 (s, 1H), 8.10 (s, 1H), 7.72-7.88 (m, 4H), 7.30-7.55 (m, 6H), 5.65-5.74 (m, 1H), 4.85-4.99 (m, 2H), 2.64 (br s, 1H), 2.50-1.71 (d, J=7.23 Hz, 3H)

Intermediate 66

Ethyl (R)-1-(((6-(4-fluorophenyl)-4-((1-(2-(trifluoromethyl)pyrimidin-5-yl)ethyl)amino)quinazolin-8-yl)oxy)methylcyclopropane-1-carboxylate

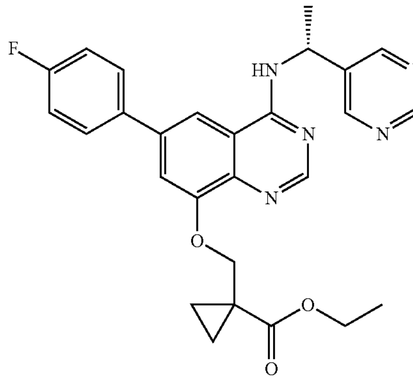

Caesium carbonate (152 mg, 0.466 mmol) was added to a stirred mixture of ethyl 1-(bromomethyl)cyclopropane-1-carboxylate (0.053 ml, 0.256 mmol) and (R)-6-(4-fluorophenyl)-4-((1-(2-(trifluoromethyl)pyrimidin-5-yl)ethyl)amino)quinazolin-8-ol (100 mg, 0.233 mmol) (Intermediate 10) in DMF (2 mL). The reaction mixture was stirred for 4 h at 60° C., then it was diluted with AcOEt and washed with brine. The organic layer was dried over sodium sulfate then filtered and concentrated under reduced pressure. Purification by chromatography (Biotage Isolera, 28 g NH cartridge, gradient elution from 0 to 10% ethyl acetate in dichloromethane in 15 CV) yielded ethyl (R)-1-(((6-(4-fluorophenyl)-4-((1-(2-(trifluoromethyl)pyrimidin-5-yl)ethyl)amino)quinazolin-8-yl)oxy)methyl)cyclopropane-1-carboxylate (68.1 mg, 0.123 mmol, 52.6% yield).

LCMS (Method 5): 0.96 min, 556.1 m/z [M+H]+

Example 41

(R)-1-(((6-(4-fluorophenyl-4-((1-(2-(trifluoromethyl)pyrimidin-5-yl)ethyl)amino)quinazolin-8-yl)oxy)methyl)cyclopropane-1-carboxylic acid

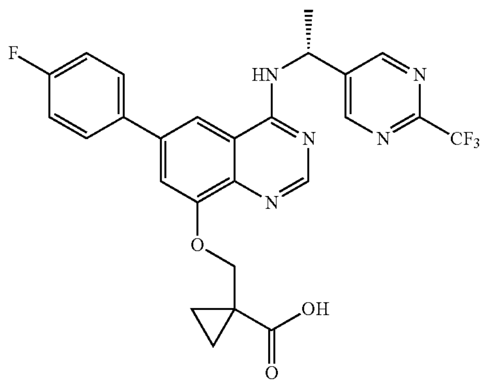 [SMILES: C[C@@H](Nc1ncnc2c(OCC3(C(=O)O)CC3)cc(-c3ccc(F)cc3)cc12)c1cnc(C(F)(F)F)nc1]

A solution of lithium hydroxide (15.2 mg, 0.635 mmol) in water (1 mL) was added to a solution of ethyl (R)-1-(((6-

(4-fluorophenyl)-4-((1-(2-(trifluoromethyl)pyrimidin-5-yl)ethyl)amino)quinazolin-8-yl)oxy)methyl)cyclopropane-1-carboxylate (68.1 mg, 0.123 mmol) in THF (3 mL). Stirring went on for 16 h at rt. Volatiles were removed under reduced pressure. Purification by chromatography (Biotage Isolera, 30 g C18 cartridge, gradient elution from 0 to 45% B in A, A: water/acetonitrile 95:5+0.1% HCOOH, B: acetonitrile: water 95:5+0.1% HCOOH in 15 CV) yielded (R)-1-(((6-(4-fluorophenyl)-4-((1-(2-(trifluoromethyl)pyrimidin-5-yl)ethyl)amino)quinazolin-8-yl)oxy)methyl)cyclopropane-1-carboxylic acid (5.1 mg, 9.67 μmol, 7.89% yield) as an off-white powder.

LCMS (Method 5): 0.80 min, 527.8 m/z [M+H]+

$^1$H NMR (400 MHz, DMSO-d6) δ ppm 12.34-12.62 (bs, 1H), 9.12 (s, 2H), 8.57 (br d, J=7.02 Hz, 1H), 8.38 (s, 1H), 8.13-8.18 (m, 1H), 7.85-7.95 (m, 2H), 7.48 (s, 1H), 7.34 (t, J=8.77 Hz, 2H), 5.64 (quin, J=6.85 Hz, 1H), 4.30 (s, 2H), 1.69 (d, J=7.02 Hz, 3H), 1.01-1.28 (m, 4H).

Example 42

Methyl 1-(2-((6-(4-fluorophenyl)-4-(((6-methylpyridazin-3-yl)methyl)amino)quinazolin-8-yl)oxy)acetamido)cyclopropane-1-carboxylate

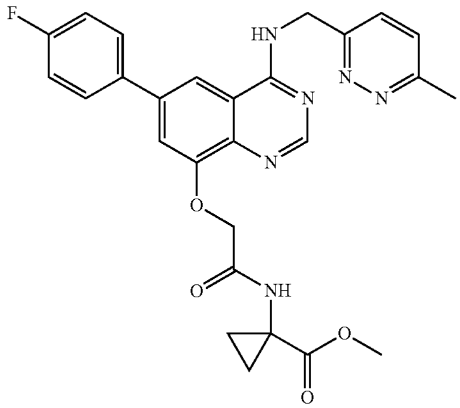 [SMILES: COC(=O)C1(NC(=O)COc2cc(-c3ccc(F)cc3)cc3c(NCc4ccc(C)nn4)ncnc23)CC1]

Methyl 1-(2-chloroacetamido)cyclopropane-1-carboxylate (49.6 mg, 0.259 mmol) was added to a stirred mixture of 6-(4-fluorophenyl)-4-(((6-methylpyridazin-3-yl)methyl)amino)quinazolin-8-ol (85 mg, 0.235 mmol) (Intermediate 19) and potassium carbonate (98 mg, 0.706 mmol) in DMF (3 ml). Stirring went on at 80° C. for 16 h, then the reaction mixture was diluted with THF and washed with saturated aqueous ammonium chloride, then with brine. The organic layer was dried over sodium sulfate, filtered and concentrated under reduced pressure. Purification by chromatography (Biotage Isolera, 28 g NH cartridge, gradient elution from 0 to 30% B in A; A: dichloromethane, B: dichloromethane/MeOH 90:10) yielded methyl 1-(2-((6-(4-fluorophenyl)-4-(((6-methylpyridazin-3-yl)methyl)amino)quinazolin-8-yl)oxy)acetamido)cyclopropane-1-carboxylate (44.0 mg, 0.085 mmol, 36.2% yield) an off-white powder.

LCMS (Method 5): 0.60 min, m/z 517.2 [M+H]+

$^1$H NMR (400 MHz, DMSO-d6) δ ppm 9.03-9.12 (m, 2H), 8.43 (s, 1H), 8.23-8.28 (m, 1H), 7.88 (dd, J=8.77, 5.48 Hz, 2H), 7.59-7.67 (m, 1H), 7.43-7.55 (m, 2H), 7.35 (t, J=8.88 Hz, 2H), 5.00 (d, J=5.48 Hz, 2H), 4.79 (s, 2H), 3.43 (s, 3H), 2.56 (s, 3H), 1.25-1.45 (m, 2H), 0.98-1.11 (m, 2H).

The following compounds were prepared via adaptations of the above procedures starting from substrate reported in table.

| Example No. | Structure | Analytical data $^1H$ NMR LC-MS | Reagents |
|---|---|---|---|
| Example 43 | Methyl (R)-1-(2-((6-(4-fluorophenyl)-4-((1-(2-(trifluoromethyl)pyrimidin-5-yl)ethyl)amino)quinazolin-8-yl)-oxy)acetamido)cyclopropane-1-carboxylate 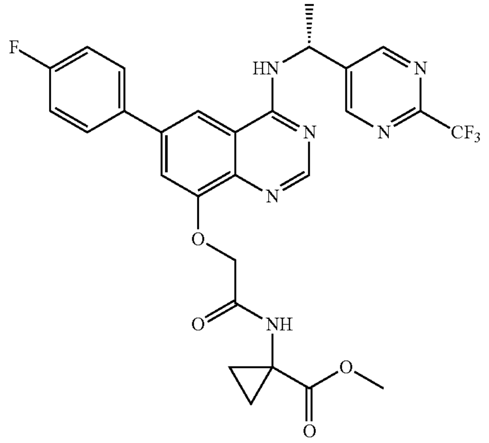 | LCMS (Method 5): 0.84 min, m/z 585.1 [M + H]+, 1H NMR (400 MHz, DMSO-d6) δ ppm 9.13 (s, 2 H), 9.02 (s, 1 H), 8.67 (d, J = 6.80 Hz, 1 H), 8.43 (s, 1 H), 8.27 (s, 1 H), 7.88 (t, J = 5.97 Hz, 2 H), 7.61 (d, J = 1.32 Hz, 1 H), 7.37 (t, J = 8.88 Hz, 2 H), 5.65 (quin, J = 6.85 Hz, 1 H), 4.77 (s, 2 H), 3.42 (s, 3 H), 1.70 (d, J = 7.23 Hz, 3 H), 1.28-1.39 (m, 2 H), 1.00-1.09 (m, 2 H). | Intermediate 10, Methyl 1-(2-chloro-acetamido)cyclo-propane-1-carbox-ylate, potassium carbonate, DMF, 80 C. |
| Intermediate 67 | | LCMS (Method 7): 2.69 min, [M + H]+ 448.4 $^1H$ NMR (300 MHz, CHLOROFORM-d) δ ppm 8.69 (s, 1 H), 7.85 (br s, 1 H), 7.50-7.61 (m, 4 H), 7.37-7.47 (m, 1 H), 7.24 (d, J = 0.92 Hz, 1 H), 7.17 (t, J = 8.62 Hz, 2 H), 5.10 (d, J = 4.03 Hz, 2 H), 5.00 (s, 2 H), 4.30 (q, J = 7.15 Hz, 2 H), 2.77 (s, 3 H), 1.29 (t, J = 7.15 Hz, 3 H). | Intermediate 19, Ethyl 2-Chloro-acetate $Cs_2CO_3$ |

Example 44

(R)-1-(2-((6-(4-fluorophenyl) 4-((1-(2-(trifluoromethyl)pyrimidin-5-yl)ethyl)amino)quinazolin-4-yl) oxy)acetamido)cyclopropane-1-carboxylic acid

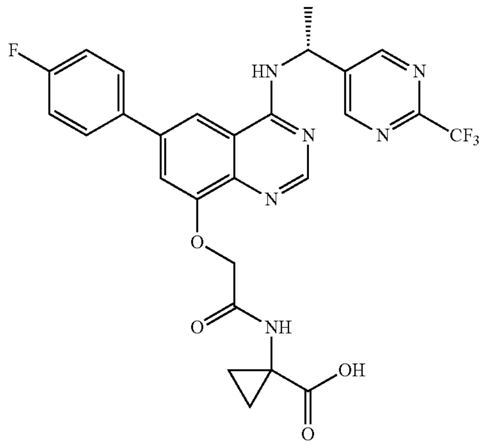 [SMILES: C[C@@H](Nc1ncnc2c(OCC(=O)NC3(C(=O)O)CC3)cc(-c3ccc(F)cc3)cc12)c1cnc(C(F)(F)F)nc1]

2N LiOH (0.2 ml, 0.400 mmol) was added to a stirred solution of methyl (R)-1-(2-((6-(4-fluorophenyl)-4-((1-(2-(trifluoromethyl)pyrimidin-5-yl)ethyl)amino)quinazolin-8-yl)oxy)acetamido)cyclopropane-1-carboxylate (50.9 mg, 0.087 mmol)(Example 43) in THF (3 ml). Stirring went on for 16 h at 80° C. Volatiles were removed under reduced pressure then DMF (2 mL) was added to the residue followed by formic acid (20 μl, 0.530 mmol). The resulting suspension was purified by chromatography (Biotage Isolera, 12 g C18 Ultra cartridge, gradient elution from 0 to 35% B in A; A: water/acetonitrile 95:5+0.1% HCOOH, B: acetonitrile:water 95:5+0.1% HCOOH) to yield (R)-1-(2-((6-(4-fluorophenyl)-4-((1-(2-(trifluoromethyl)pyrimidin-5-yl)ethyl)amino)quinazolin-8-yl)oxy)acetamido)cyclopropane-1-carboxylic acid (9.9 mg, 0.017 mmol, 19.93% yield) as a white powder.

LCMS (Method 5): 0.77 min, m/z 570.8 [M+H]+

$^1H$ NMR (400 MHz, DMSO-d6) δ ppm 11.90-12.82 (bs, 1H), 9.13 (s, 2H), 8.90 (s, 1H), 8.67 (br d, J=7.02 Hz, 1H), 8.43 (s, 1H), 8.26 (s, 1H), 7.88 (dd, J=8.77, 5.48 Hz, 2H), 7.61 (s, 1H), 7.35 (t, J=8.77 Hz, 2H), 5.66 (quin, J=6.80 Hz, 1H), 4.75 (s, 2H), 1.70 (d, J=7.23 Hz, 3H), 1.23-1.40 (m, 2H), 0.90-1.03 (m, 2H).

Intermediate 67a

2-[6-(4-fluorophenyl)-4-[(6-methylpyridazin-3-yl) methylamino]quinazolin-s-yl]oxyacetic acid, Sodium Salt

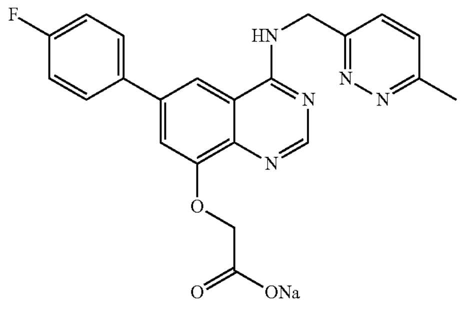

NaOH (10.5 mg, 0.26 mmol) was added to ethyl 2-[6-(4-fluorophenyl)-4-[(6-methylpyridazin-3-yl)methylamino] quinazolin-8-yl]oxyacetate (117 mg, 0.26 mmol) (Intermediate 67) in MeOH (2.2 mL). The mixture was stirred at rt for 3 days then diluted with diethyl ether and filtered to leave 2-[6-(4-fluorophenyl)-4-[(6-methylpyridazin-3-yl)methyl-amino]quinazolin-8-yl]oxyacetic acid sodium salt (87 mg, 75% yield) as a white powder.

Intermediate 68

Ethyl (1R,2S)-2-(2-((6-(4-fluorophenyl)-4-(((6-methylpyridazin-3-yl)methyl)amino)quinazolin-8-yl) oxy)acetamido)cyclopentane-1-carboxylate

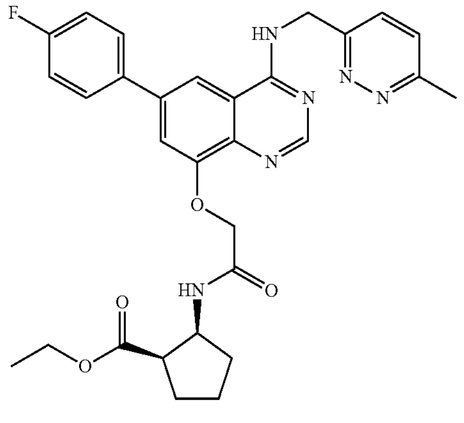 [SMILES: CCOC(=O)[C@@H]1CCC[C@@H]1NC(=O)COc1cc(-c2ccc(F)cc2)cc2c(NCc3ccc(C)nn3)ncnc12]

PyAOP (82 mg, 0.157 mmol) was added to a mixture of 2-((6-(4-fluorophenyl)-4-(((6-methylpyridazin-3-yl)methyl) amino)quinazolin-8-yl)oxy)acetic acid (55 mg, 0.131 mmol) (Intermediate 67a), ethyl (1R,2S)-2-aminocyclopentane-1-carboxylate (24.74 mg, 0.157 mmol) and DIPEA (0.069 mL, 0.393 mmol) in THF (3 mL). Stirring went on for 1 h at rt. The reaction was diluted by the addition of AcOEt, then it was washed with saturated aqueous ammonium chloride, saturated aqueous sodium bicarbonate and brine. The organic layer was dried over sodium sulfate, filtered and concentrated under reduced pressure. Purification by chromatography (Biotage Isolera, 28 g NH cartridge, gradient elution from 0 to 100% EtOAc in dichloromethane in 25 CV) followed by RP chromatography (Biotage Isolera, 12 g C18 Ultra cartridge, gradient elution from 0 to 35% B in A in 25 CV; A: water/acetonitrile 95:5+0.1% HCOOH, B: acetonitrile:water 95:5+0.1% HCOOH) yielded ethyl (1R, 2S)-2-(2-((6-(4-fluorophenyl)-4-(((6-methylpyridazin-3-yl) methyl)amino)quinazolin-8-yl)oxy)acetamido)cyclopentane-1-carboxylate (21.4 mg, 0.038 mmol, 29.2% yield) as an off-white powder.

LCMS (Method 5): 0.72 min, 559.4 [M+H]+.

$^{1}$H NMR (400 MHz, DMSO-d6) δ ppm 9.11 (t, J=5.81 Hz, 1H), 8.48 (d, J=8.55 Hz, 1H), 8.41 (s, 1H), 8.26 (d, J=1.53 Hz, 1H), 7.84-7.91 (m, 2H), 7.72 (d, J=1.53 Hz, 1H), 7.49-7.53 (m, 1H), 7.44-7.49 (m, 1H), 7.34 (t, J=8.88 Hz, 2H), 5.01 (d, J=5.70 Hz, 2H), 4.70-4.79 (m, 2H), 4.36-4.43 (m, 1H), 3.60-3.77 (m, 2H), 2.89 (q, J=7.31 Hz, 1H), 2.55 (s, 3H), 1.71-1.90 (m, 4H), 1.47-1.62 (m, 2H), 0.92 (t, J=7.13 Hz, 3H).

Example 45

(1R,2S)-2-(2-((6-(4-fluorophenyl)-4-(((6-methylpyridazin-3-yl)methyl)amino)quinazolin-8-yl)oxy) acetamido)cyclopentane-1-carboxylic acid

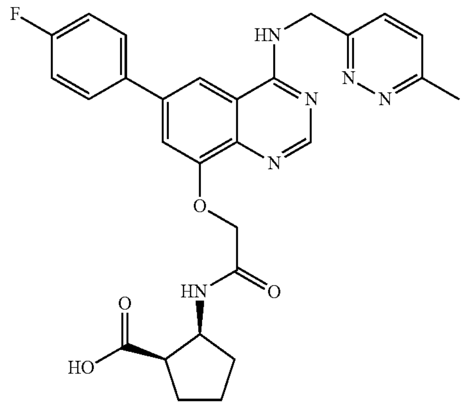 [SMILES: Cc1ccc(CNc2ncnc3c(OCC(=O)N[C@H]4CCC[C@H]4C(=O)O)cc(-c4ccc(F)cc4)cc23)nn1]

2N NaOH (0.050 mL, 0.100 mmol) was added to a stirred solution of ethyl (1R,2S)-2-(2-((6-(4-fluorophenyl)-4-(((6-methylpyridazin-3-yl)methyl)amino)quinazolin-8-yl)oxy) acetamido)cyclopentane-1-carboxylate (17.0 mg, 0.030 mmol) (Intermediate 68) in MeOH (2 mL). After 64 h. Volatiles were removed under reduced pressure. Purification by chromatography (Biotage Isolera, 12 g C18 cartridge, gradient elution from 0 to 25% B in A in 30 CV; A: water/acetonitrile 95:5+0.1% HCOOH, B: acetonitrile:water 95:5+0.1% HCOOH) yielded (1R,2S)-2-(2-((6-(4-fluorophenyl)-4-(((6-methylpyridazin-3-yl)methyl)amino)quinazolin-8-yl)oxy)acetamido)cyclopentane-1-carboxylic acid (11.5 mg, 0.022 mmol, 71.2% yield) as an off-white powder.

LCMS (Method 5): 0.72 min, 559.4 [M+H]+

$^{1}$H NMR (400 MHz, DMSO-d6) δ ppm 9.06-9.15 (m, 1H), 8.73 (d, J=7.89 Hz, 1H), 8.36-8.46 (m, 1H), 8.22-8.29 (m, 1H), 7.78-7.91 (m, 2H), 7.64-7.72 (m, 1H), 7.43-7.54 (m, 2H), 7.29-7.38 (m, 2H), 5.00 (d, J=5.48 Hz, 2H), 4.70-4.78 (m, 2H), 4.27 (t, J=7.13 Hz, 1H), 3.45-3.65 (m, 1H), 2.55 (s, 3H), 1.35-1.97 (m, 6H).

Example 46

Ethyl (1S,2R)-2-(2-((6-(4-fluorophenyl)-4-(((6-methylpyridazin-3-yl)methyl)amino)quinazolin-8-yl)oxy)acetamido)cyclopentane-1-carboxylate

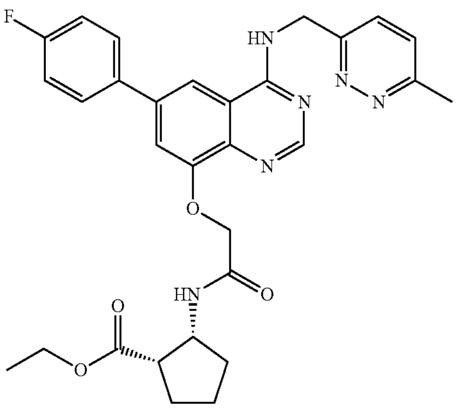 [SMILES: CCOC(=O)[C@H]1CCC[C@H]1NC(=O)COc1cc(-c2ccc(F)cc2)cc2c(NCc3ccc(C)nn3)ncnc12]

PyAOP (82 mg, 0.157 mmol) was added to a mixture of 2-((6-(4-fluorophenyl)-4-(((6-methylpyridazin-3-yl)methyl)amino)quinazolin-8-yl)oxy)acetic acid (55 mg, 0.131 mmol) (Intermediate 67a), ethyl (1S,2R)-2-aminocyclopentane-1-carboxylate (25 μL, 0.131 mmol) and DIPEA (68.5 μL, 0.393 mmol) in THF (3 mL). Stirring went on for 1 h at rt. Then formic acid (29.7 μL, 0.787 mmol) was added and volatiles were removed under reduced pressure. Purification by chromatography (Biotage Isolera, 30 g C18 cartridge, gradient elution from 0 to 30% B in A in 30 CV; A: water/acetonitrile 95:5+0.1% HCOOH, B: acetonitrile:water 95:5+0.1% HCOOH) yielded ethyl (1S,2R)-2-(2-((6-(4-fluorophenyl)-4-(((6-methylpyridazin-3-yl)methyl)amino)quinazolin-8-yl)oxy)acetamido)cyclopentane-1-carboxylate (27.5 mg, 0.049 mmol, 37.5% yield) as an off-white powder.

LCMS (Method 5): 0.72 min, 559.4 [M+H]+

$^1$H NMR (400 MHz, DMSO-d6) δ ppm 9.11 (t, J=5.81 Hz, 1H), 8.48 (d, J=8.55 Hz, 1H), 8.41 (s, 1H), 8.26 (d, J=1.53 Hz, 1H), 7.84-7.91 (m, 2H), 7.72 (d, J=1.53 Hz, 1H), 7.49-7.53 (m, 1H), 7.44-7.49 (m, 1H), 7.34 (t, J=8.88 Hz, 2H), 5.01 (d, J=5.70 Hz, 2H), 4.70-4.79 (m, 2H), 4.36-4.43 (m, 1H), 3.60-3.77 (m, 2H), 2.89 (q, J=7.31 Hz, 1H), 2.55 (s, 3H), 1.71-1.90 (m, 4H), 1.47-1.62 (m, 2H), 0.92 (t, J=7.13 Hz, 3H).

Intermediate 69

1-(tert-butyl) 4-ethyl (R)-4-(((6-(4-fluorophenyl)-4-((1-(2-(trifluoromethyl)pyrimidin-5-yl)ethyl)amino)quinazolin-8-yl)oxy)methyl)piperidine-1,4-dicarboxylate

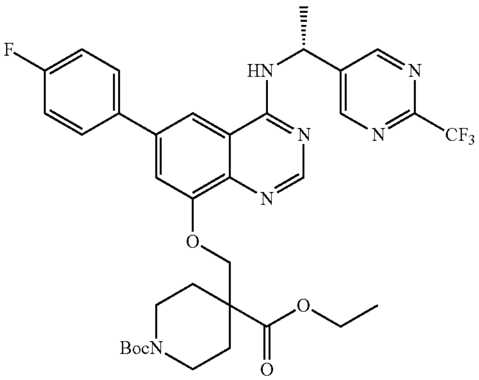 [SMILES: CCOC(=O)C1(COc2cc(-c3ccc(F)cc3)cc3c(N[C@H](C)c4cnc(C(F)(F)F)nc4)ncnc23)CCN(C(=O)OC(C)(C)C)CC1]

Caesium carbonate (152 mg, 0.466 mmol) was added to a stirred mixture of 1-(tert-butyl) 4-ethyl 4-(iodomethyl)piperidine-1,4-dicarboxylate (102 mg, 0.256 mmol) and (R)-6-(4-fluorophenyl)-4-((1-(2-(trifluoromethyl)pyrimidin-5-yl)ethyl)amino)quinazolin-8-ol (100 mg, 0.233 mmol) (Intermediate 10) in DMF (2 mL). Stirring went on at for 5 h at 100° C. The reaction mixture was diluted with AcOEt and washed with brine. The organic layer was dried over sodium sulfate then filtered and concentrated under reduced pressure. Purification by chromatography yielded 1-(tert-butyl) 4-ethyl (R)-4-(((6-(4-fluorophenyl)-4-((1-(2-(trifluoromethyl)pyrimidin-5-yl)ethyl)amino)quinazolin-8-yl)oxy)methyl)piperidine-1,4-dicarboxylate (39.9 mg, 0.057 mmol, 24.52% yield).

LCMS (Method 5): 1.07 min, 698.8 m/z [M+H]+

Intermediate 70

(R)-1-(tert-butoxycarbonyl)-4-(((6-(4-fluorophenyl)-4-((1-(2-(trifluoromethyl)pyrimidin-5-yl)ethyl)amino)quinazolin-8-yl)oxy)methyl)piperidine-4-carboxylic acid

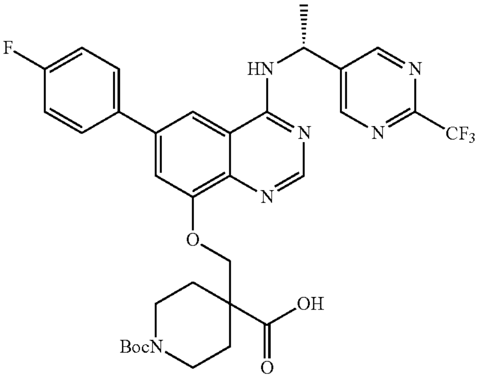 [SMILES: C[C@@H](Nc1ncnc2c(OCC3(C(=O)O)CCN(C(=O)OC(C)(C)C)CC3)cc(-c3ccc(F)cc3)cc12)c1cnc(C(F)(F)F)nc1]

A solution of lithium hydroxide (140 mg, 5.85 mmol) in water (1 mL) was added to a solution of 1-(tert-butyl) 4-ethyl (R)-4-(((6-(4-fluorophenyl)-4-((1-(2-(trifluoromethyl)pyrimidin-5-yl)ethyl)amino)quinazolin-8-yl)oxy)methyl)piperidine-1,4-dicarboxylate (39.9 mg, 0.057 mmol) in THF (3 mL). Stirring went on for 16 h at rt. Formic acid (300 μl, 7.95 mmol) was added and the volatiles were removed under reduced pressure. Purification by chromatography (Biotage Isolera, 30 g C18 cartridge, gradient elution from 0 to 55% B in A, A: water/acetonitrile 95:5+0.1% HCOOH, B: acetonitrile:water 95:5+0.1% HCOOH in 15 CV) yielded (R)-1-(tert-butoxycarbonyl)-4-(((6-(4-fluorophenyl)-4-((1-(2-(trifluoromethyl)pyrimidin-5-yl)ethyl)amino)quinazolin-8-yl)oxy)methyl)piperidine-4-carboxylic acid (17.9 mg, 0.027 mmol, 46.7% yield) as an off-white powder.

LCMS (Method 5): 0.96 min, 670.8 m/z [M+H]+, $^1$H NMR (400 MHz, DMSO-d6) δ ppm 11.91-13.22 (bs, 1H), 9.12 (s, 2H), 8.56 (br d, J=6.80 Hz, 1H), 8.38 (s, 1H), 8.17 (s, 1H), 7.90 (dd, J=8.66, 5.59 Hz, 2H), 7.53 (s, 1H), 7.34 (t, J=8.88 Hz, 2H), 5.63 (br t, J=6.91 Hz, 1H), 4.28 (s, 2H), 3.66 (br d, J=13.59 Hz, 2H), 2.94-3.20 (m, 2H), 2.01 (br d, J=13.81 Hz, 2H), 1.69 (d, J=7.02 Hz, 3H), 1.57-1.66 (m, 2H), 1.36 (s, 9H).

Example 47

(R)-4-(((6-(4-fluorophenyl)-4-((1-(2-(trifluoromethyl)pyrimidin-5-yl)ethyl)amino)quinazolin-8-yl)oxy)methyl)piperidine-4-carboxylic acid hydrochloride

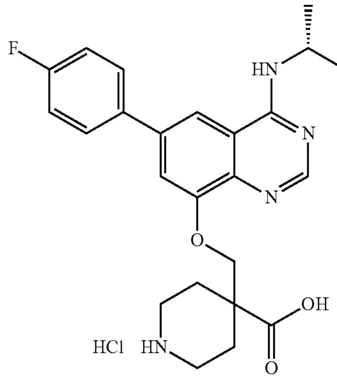

37% HCl (0.5 mL, 6.00 mmol) was added to a mixture of (R)-1-(tert-butoxycarbonyl)-4-(((6-(4-fluorophenyl)-4-((1-(2-(trifluoromethyl)pyrimidin-5-yl)ethyl)amino)quinazolin-8-yl)oxy)methyl)piperidine-4-carboxylic acid (12.3 mg, 0.018 mmol) (intermediate 65) in 1 M HCl in AcOEt (2 mL, 2.000 mmol). Stirring went on for 48 h at rt. Volatiles were removed under reduced pressure. Purification by RP chromatography (Biotage Isolera, 12 g C18 cartridge, gradient elution from 0 to 25% B in A, A: water/acetonitrile 95:5+0.1% conc HCl, B: acetonitrile:water 95:5+0.1% conc HCl in 15 CV) yielded (R)-4-(((6-(4-fluorophenyl)-4-((1-(2-(trifluoromethyl)pyrimidin-5-yl)ethyl)amino)quinazolin-8-yl)oxy)methyl)piperidine-4-carboxylic acid hydrochloride (6.1 mg, 10.05 μmol, 54.8% yield).

LCMS (Method 5): 0.59 min, 570.8 m/z [M+H]+

$^{1}$H NMR (400 MHz, DMSO-d6) 0 ppm 13.9 (br s, 0.5H), 13.1 (br s, 1H), 10.7 (br s, 0.5H), 9.19 (br s, 2H), 9.05-8.30 (m, 4H), 8.10-7.70 (m, 3H), 7.39 (t, J=8.66 Hz, 2H), 6.00-5.66 (m, 1H), 4.56-4.30 (m, 2H), 3.33 (m, 2H), 3.01 (m, 2H), 2.36-2.08 (m, 4H), 1.78 (br d, J=5.26 Hz, 3H).

Example 48

(R)-1-(((6-(4-fluorophenyl-4-((1-(2-(trifluoromethyl)pyrimidin-5-yl)ethyl)amino)quinazolin-8-yl)oxy)methyl)cyclohexane-1-carboxylic acid

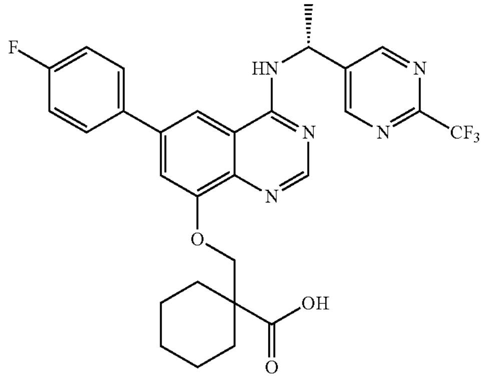 [SMILES: C[C@@H](Nc1ncnc2c(OCC3(C(=O)O)CCCCC3)cc(-c3ccc(F)cc3)cc12)c1cnc(C(F)(F)F)nc1]

Intermediate 71

Methyl (R)-1-(((6-(4-fluorophenyl)-4-((1-(2-(trifluoromethyl)pyrimidin-5-yl)ethyl)amino)quinazolin-8-yl)oxy)methyl)cyclohexane-1-carboxylate

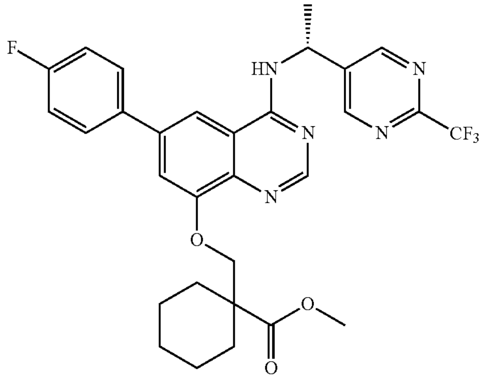 [SMILES: COC(=O)C1(COc2cc(-c3ccc(F)cc3)cc3c(N[C@H](C)c4cnc(C(F)(F)F)nc4)ncnc23)CCCCC1]

Methyl 1-(bromomethyl)cyclohexane-1-carboxylate (90 mg, 0.384 mmol) was added to a stirred mixture of (R)-6-(4-fluorophenyl)-4-((1-(2-(trifluoromethyl)pyrimidin-5-yl)ethyl)amino)quinazolin-8-ol (150 mg, 0.349 mmol) (Intermediate 10), sodium iodide (155 mg, 1.034 mmol) and cesium carbonate (240 mg, 0.737 mmol) in DMF (3 ml). Stirring went on at 110° C. for 16 h, then the reaction mixture was allowed to cool down to rt. The reaction mixture was diluted with EtOAc and washed with saturated aqueous ammonium chloride, then with brine. The organic layer was dried over sodium sulfate, filtered and concentrated under reduced pressure. Purification by chromatography (Biotage Isolera, 28 g NH cartridge, elution in dichloromethane 15 CV) yielded methyl (R)-1-(((6-(4-fluorophenyl)-4-((1-(2-(trifluoromethyl)pyrimidin-5-yl)ethyl)amino)quinazolin-8-yl)oxy)methyl)cyclohexane-1-carboxylate (50.9 mg, 0.087 mmol, 24.97% yield) a pale yellow powder.

LCMS (Method 5): 1.02 min. m/z 583.9 [M+H]+

Preparation of (R)-1-(((6-(4-fluorophenyl)-4-((1-(2-(trifluoromethyl)pyrimidin-5-yl)ethyl)amino)quinazolin-8-yl)oxy)methyl)cyclohexane-1-carboxylic acid (Example 48)

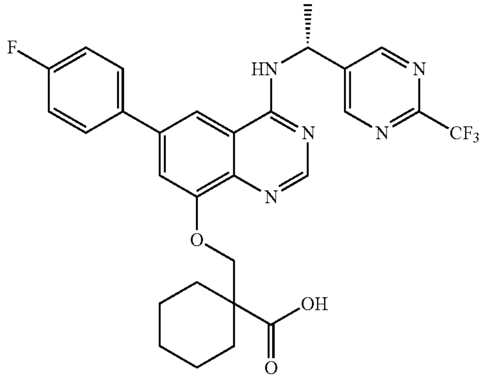 [SMILES: C[C@@H](Nc1ncnc2c(OCC3(C(=O)O)CCCCC3)cc(-c3ccc(F)cc3)cc12)c1cnc(C(F)(F)F)nc1]

A solution of lithium hydroxide (40 mg, 1.670 mmol) in water (1 mL) was added to a solution of methyl (R)-1-(((6-(4-fluorophenyl)-4-((1-(2-(trifluoromethyl)pyrimidin-5-yl)ethyl)amino)quinazolin-8-yl)oxy)methyl)cyclohexane-1-carboxylate (50.9 mg, 0.087 mmol) in THF (3 ml). Stirring went on for 48 h at 70° C. The reaction mixture was diluted with acetonitrile and volatiles were removed under reduced pressure. Purification by chromatography (Biotage Isolera, 30 g C18 cartridge, gradient elution from 0 to 20% B in A, A: water/acetonitrile 95:5+0.1% HCOOH, B: acetonitrile:water 95:5+0.1% HCOOH in 15 CV) yielded (R)-1-(((6-(4-fluorophenyl)-4-((1-(2-(trifluoromethyl)pyrimidin-5-yl)ethyl)amino)quinazolin-8-yl)oxy)methyl)cyclohexane-1-carboxylic acid (44.1 mg, 0.077 mmol, 89% yield) as a pale beige powder.

LCMS (Method 5): 0.98 min, 570.2 m/z [M+H]+

$^1$H NMR (400 MHz, DMSO-d6) δ ppm 12.16-12.43 (bs, 1H), 9.12 (s, 2H), 8.56 (br s, 1H), 8.39 (s, 1H), 8.16 (s, 1H), 7.90 (dd, J=8.77, 5.48 Hz, 2H), 7.52 (s, 1H), 7.34 (t, J=8.77 Hz, 2H), 5.63 (quin, J=6.96 Hz, 1H), 4.23 (s, 2H), 2.00 (br dd, J=11.51, 4.49 Hz, 1H), 1.95-2.06 (m, 2H), 1.69 (d, J=7.23 Hz, 3H), 1.38-1.57 (m, 6H), 1.11-1.38 (m, 2H).

Intermediate 72

2-((4-(((6-methylpyridazin-3-yl)methyl)amino)-6-(5-methylpyrimidin-2-yl)quinazolin-8-yl)oxy)acetic acid dihydrochloride

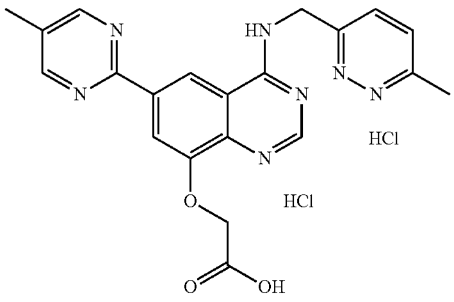

Step 1: Preparation of tert-butyl 2-((4-(((6-methylpyridazin-3-yl)methyl)amino)-6-(5-methylpyrimidin-2-yl)quinazolin-8-yl)oxy)acetate

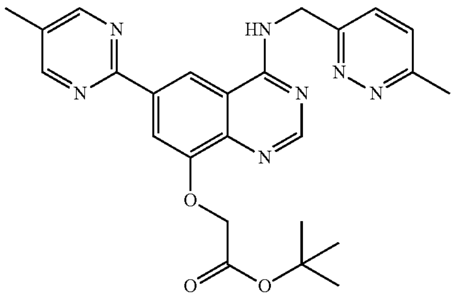

Tert-butyl 2-bromoacetate (247 μL, 1.669 mmol) was added to a stirred mixture of 4-(((6-methylpyridazin-3-yl)methyl)amino)-6-(5-methylpyrimidin-2-yl)quinazolin-8-ol (500 mg, 1.391 mmol) (intermediate 57) and potassium carbonate (456 mg, 3.30 mmol) in DMF/THF 2:1 (9 mL). Stirring went on at rt for 16 h. The reaction was quenched by the addition of formic acid (300 μL, 7.95 mmol) and volatiles were removed under reduced pressure. Purification by RP chromatography (Biotage Isolera, 60 g C18 cartridge, gradient elution from 0 to 30% B in A; A: water/acetonitrile 95:5+0.1% HCOOH, B: acetonitrile/water 95:5+0.1% HCOOH) yielded tert-butyl 2-((4-(((6-methylpyridazin-3-yl)methyl)amino)-6-(5-methylpyrimidin-2-yl)quinazolin-8-yl)oxy)acetate (451 mg, 0.952 mmol, 68.5% yield) as an orange wax.

LCMS (Method 5): 0.66 min, 473.8 [M+H]+

Step 2: Preparation of 2-((4-(((6-methylpyridazin-3-yl)methyl)amino)-6-(5-methylpyrimidin-2-yl)quinazolin-8-yl)oxy)acetic acid dihydrochloride

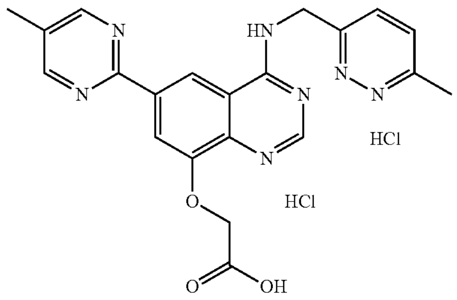

Tert-butyl 2-((4-(((6-methylpyridazin-3-yl)methyl)amino)-6-(5-methylpyrimidin-2-yl)quinazolin-8-yl)oxy)acetate was stirred in 4N HCl in 1,4-dioxane (20 ml, 80 mmol) for 16 h at rt. Volatiles were removed under reduced pressure to yield 2-((4-(((6-methylpyridazin-3-yl)methyl)amino)-6-(5-methylpyrimidin-2-yl)quinazolin-8-yl)oxy)acetic acid dihydrochloride (552 mg, 1.126 mmol, 81% yield) as a pale yellow powder.

LCMS (Method 5): 0.45 min, 418.0 [M+H]+, $^1$H NMR (400 MHz, DMSO-d6) δ ppm 11.20 (br t, J=5.48 Hz, 1H), 9.18 (s, 1H), 8.88 (s, 2H), 8.80 (s, 1H), 8.41 (s, 1H), 7.77 (d, J=8.55 Hz, 1H), 7.65 (d, J=8.55 Hz, 1H), 5.16-5.28 (m, 4H), 2.63 (s, 3H), 2.38 (s, 3H)

Example 49

Ammonium (2-((4-(((6-methylpyridazin-3-yl)methyl)amino)-6-(5-methylpyrimidin-2-yl)quinazolin-8-yl)oxy)acetyl)(phenylsulfonyl)amide

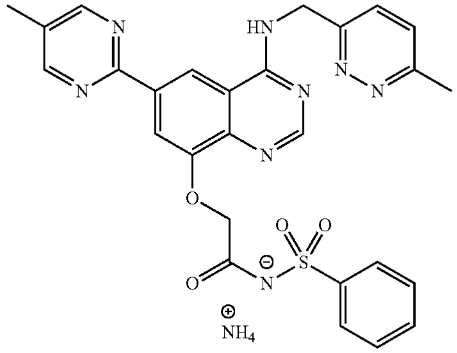

EDCI (58.6 mg, 0.306 mmol) was added to a stirred solution of 2-((4-(((6-methylpyridazin-3-yl)methyl)amino)-6-(5-methylpyrimidin-2-yl)quinazolin-8-yl)oxy)acetic acid dihydrochloride (100 mg, 0.204 mmol) (Intermediate 72, benzenesulfonamide (48.1 mg, 0.306 mmol), DMAP (100 mg, 0.816 mmol) and DIPEA (0.355 mL, 2.039 mmol) in DMF (2 mL). Stirring went on for 16 h at rt. The reaction was quenched by the addition of formic acid (0.115 mL, 3.06 mmol), then volatiles were removed under reduced pressure. Purification by RP chromatography (Biotage Isolera, 12 g C18 cartridge, gradient elution from 0 to 25% B in A; A: water/MeOH 95:5+0.1% conc. ammonia, B: MeOH/water 95:5+0.1% conc. ammonia) yielded ammonium (2-((4-(((6-methylpyridazin-3-yl)methyl)amino)-6-(5-methylpyrimidin-2-yl)quinazolin-8-yl)oxy)acetyl)(phenylsulfonyl)amide (34.8 mg, 0.061 mmol, 29.7% yield) as a white powder.

LCMS (Method 5): 0.64 min, 557.1 [M+H]+,

1H NMR (400 MHz, DMSO-d6) δ ppm 9.34 (br s, 1H), 8.84 (s, 1H), 8.80 (s, 2H), 8.39 (s, 1H), 8.03 (s, 1H), 7.72 (d, J=7.67 Hz, 2H), 7.40-7.50 (m, 2H), 7.24-7.34 (m, 1H), 7.18 (br t, J=7.45 Hz, 4H), 4.98 (br d, J=5.26 Hz, 2H), 4.60 (s, 2H), 2.55 (s, 3H), 2.35 (s, 3H)

Intermediate 73

2-((6-(4-fluorophenyl)-4-(((1-methylpiperidin-4-yl)methyl)amino)quinazolin-8-yl)oxy)acetic acid Hydrochloride

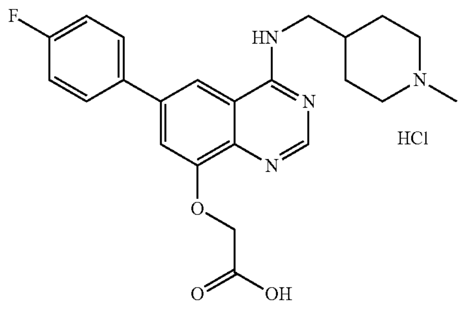 [SMILES: CN1CCC(CNc2ncnc3c(OCC(=O)O)cc(-c4ccc(F)cc4)cc23)CC1 ; Cl]

Step 1: Preparation of tert-butyl (6-(4-fluorophenyl)-8-hydroxyquinazolin-4-yl)((1-methylpiperidin-4-yl)methyl)carbamate

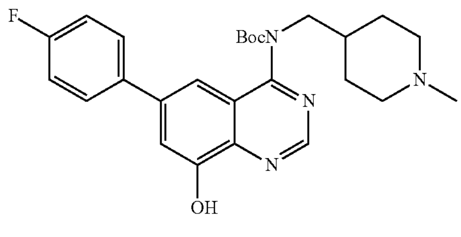 [SMILES: CN1CCC(CN(C(=O)OC(C)(C)C)c2ncnc3c(O)cc(-c4ccc(F)cc4)cc23)CC1]

A solution of di-tert-butyl dicarbonate (1.641 mL, 7.14 mmol) in THF (10 mL) was added to a stirred solution of 6-(4-fluorophenyl)-4-(((1-methylpiperidin-4-yl)methyl)amino)quinazolin-8-ol (1.19 g, 3.25 mmol)(Intermediate 5) and DIPEA (1.244 mL, 7.14 mmol) in THF (20 mL). 4-dimethylamino pyridine (0.079 g, 0.649 mmol) was then added and stirring went on for 16 h at rt. LCMS showed complete conversion to tert-butyl (8-((tert-butoxycarbonyl)oxy)-6-(4-fluorophenyl)quinazolin-4-yl)((1-methylpiperidin-4-yl)methyl)carbamate. Volatiles were removed under reduced pressure and the residue was partitioned between EtOAc/THF 1:1 and saturated aqueous ammonium chloride. The layers were separated and the organic layer was washed with brine, dried over sodium sulfate, filtered and concentrated under reduced pressure. The crude material was redissolved in dichloromethane (20 mL) and treated with 2.0 M dimethylamine in THF (4 mL). Stirring went on at rt for 4 h, then volatiles were removed under reduced pressure. Purification by column chromatography (Biotage Isolera, 55 g NH cartridge, gradient elution from 0 to 30% EtOH in dichloromethane) yielded tert-butyl (6-(4-fluorophenyl)-8-hydroxyquinazolin-4-yl)((1-methylpiperidin-4-yl)methyl)carbamate (398 mg, 0.853 mmol, 26.3% yield) as an orange powder.

LCMS (Method 5): 1.32 min, 467.4 [M+H]+.

Step 2: preparation of 2-((6-(4-fluorophenyl)-4-(((1-methylpiperidin-4-yl)methyl)amino)quinazolin-8-yl)oxy)acetic acid Hydrochloride (Intermediate 73)

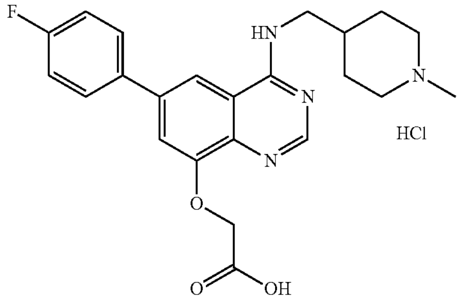 [SMILES: CN1CCC(CNc2ncnc3c(OCC(=O)O)cc(-c4ccc(F)cc4)cc23)CC1 ; Cl]

Tert-butyl 2-bromoacetate (0.075 mL, 0.509 mmol) was added to a stirred suspension of potassium carbonate (147 mg, 1.061 mmol) and tert-butyl (6-(4-fluorophenyl)-8-hydroxyquinazolin-4-yl)((1-methylpiperidin-4-yl)methyl)carbamate (198 mg, 0.424 mmol) in DMF (2 mL). Stirring went of for 16 h at rt. The reaction mixture was diluted with EtOAc and washed with brine (3×). The organic layer was dried over sodium sulfate, filtered and concentrated under reduced pressure. Purification by column chromatography (Biotage Isolera, 28 g NH cartridge, gradient elution from 0 to 20% AcOEt in dichloromethane) yielded the intermediate tert-butyl 2-((4-((tert-butoxycarbonyl)((1-methylpiperidin-4-yl)methyl)amino)-6-(4-fluorophenyl)quinazolin-8-yl)oxy)acetate. This material was dissolved rt in 1,4-dioxane (3 mL) then treated with 4N HCl for 18 h at rt. Removal of volatiles under reduced pressure yielded 2-((6-(4-fluorophenyl)-4-(((1-methylpiperidin-4-yl)methyl)amino)quinazolin-8-yl)oxy)acetic acid hydrochloride (88.1 mg, 0.191 mmol, 45.0% yield) as a pale yellow powder.

LCMS (Method 5): 0.33 min, 425.2 [M+H]+

$^{1}$H NMR (400 MHz, DMSO-d6) δ ppm 13.95-14.23 (bs, 1H), 10.65-10.55 (bs, 1H), 10.11-10.18 (m, 1H), 8.72 (s, 1H), 8.53 (s, 1H), 7.95 (br dd, J=8.33, 5.48 Hz, 2H), 7.87 (s, 1H), 7.38 (t, J=8.77 Hz, 2H), 5.19 (s, 2H), 3.60-3.50 (m, 2H), 3.17-3.34 (br s, 3H), 2.74-2.90 (m, 2H), 2.67 (s, 3H), 2.50-2.53 (m, 1H), 1.97-2.05 (m, 1H), 1.90 (br d, J=13.37 Hz, 2H), 1.40-1.61 (m, 2H)

Intermediate 74

(3-Methyl-1,2,4-oxadiazol-5-yl)methyl methanesulfonate

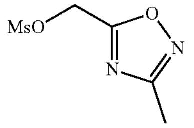

A solution of (3-methyl-1,2,4-oxadiazol-5-yl)methanol (300 mg, 2.63 mmol) and triethylamine (1.1 mL, 7.89 mmol) in DCM (6 mL) was stirred at 0° C. for 5 minutes. Methansulfonyl chloride (0.41 mL, 5.26 mmol) was added and the reaction mixture was stirred at 0° C. for 15 minutes. The reaction was then warmed to room temperature and stirred for 16 hours. The reaction was partitioned between DCM and water and the two phases were separated. The aqueous phase was extracted with DCM and the combined organic phases were passed through phase separating paper. The solvent was removed in vacuo to afford the title compound as an orange oil (290 mg, 57% yield).

$^1$H NMR (400 MHz, $CDCl_3$): δ 4.66 (s, 2H), 3.49 (s, 3H), 2.43 (s, 3H).

Intermediate 75

6-(4-Fluorophenyl)-8-[(3-methyl-1,2,4-oxadiazol-5-yl)methoxy]-N-[(6-methylpyridazin-3-yl)methyl]quinazolin-4-amine

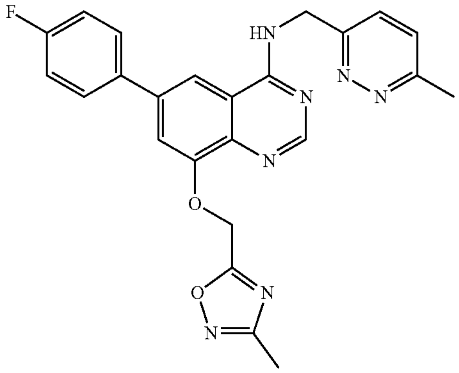 [SMILES: Cc1ccc(CNc2ncnc3c(OCc4nc(C)no4)cc(-c4ccc(F)cc4)cc23)nn1]

(3-Methyl-1,2,4-oxadiazol-5-yl)methyl methanesulfonate (176 mg, 0.46 mmol), 6-(4-fluorophenyl)-4-(((6-methylpyridazin-3-yl)methyl)amino)quinazolin-8-ol (150 mg, 0.23 mmol) and cesium carbonate (223 mg, 0.69 mmol) were dissolved in DMF (4 mL). The reaction mixture was heated at 55° C. for 16 hours. The reaction was cooled to room temperature and then it was partitioned between DCM and water. The two phases were separated and the aqueous phase was extracted with DCM (×2). The combined organic phases were passed through phase separating paper and concentrated in vacuo. Purification by preparative HPLC afforded the title compound (78.1 mg, 75%) as an off-white solid.

$^1$H NMR (400 MHz, DMSO): δ 9.13 (t, J=5.9 Hz, 1H), 8.45 (s, 1H), 8.30 (d, J=1.5 Hz, 1H), 7.95-7.90 (m, 2H), 7.75 (d, J=1.6 Hz, 1H), 7.59-7.49 (m, 2H), 7.43-7.38 (m, 2H), 5.80 (s, 2H), 5.04 (d, J=5.9 Hz, 2H), 2.61-2.60 (m, 3H), 2.39 (s, 3H). LCMS (Method 3): [$MH^+$]=458 at 4.29 min.

The following compounds were prepared via adaptations of the above procedures starting from substrate reported in table.

| Example No. | Structure | Analytical data $^1$H NMR LC-MS | Reagents |
|---|---|---|---|
| Example 50 | 6-(4-fluorophenyl)-8-[(3-methyloxetan-3-yl)methoxy]-N-[(6-methylpyridazin-3-yl)methyl]quinazolin-4-amine 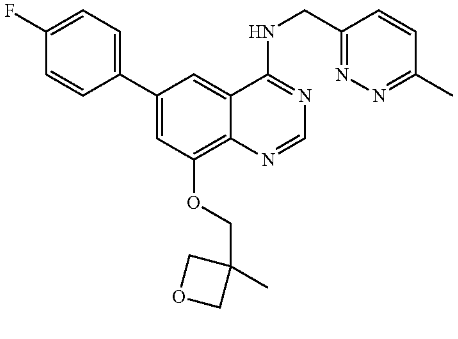 | $^1$H NMR (400 MHz, DMSO): δ 9.05 (dd, J = 5.9, 5.9 Hz, 1 H), 8.46 (s, 1 H), 8.22 (d, J = 1.6 Hz, 1 H), 7.98-7.93 (m, 2 H), 7.65 (d, J = 1.5 Hz, 1 H), 7.55 (d, J = 8.7 Hz, 1 H), 7.50 (d, J = 8.7 Hz, 1 H), 7.39 (dd, J = 8.8, 8.8 Hz, 2 H), 5.04 (d, J = 5.8 Hz, 2 H), 4.60 (d, J = 5.8 Hz, 2 H), 4.39-4.35 (m, 4 H), 2.60 (s, 3 H), 1.47 (s, 3 H). LCMS (Method 3): [$MH^+$] = 446 at 3.9 min. | Intermediate 11, 3-methyl-3-(p-toluenesulfonyloxymethyl)-oxetane, $Cs_2CO_3$ |

-continued

| Example No. | Structure | Analytical data $^1$H NMR LC-MS | Reagents |
|---|---|---|---|
| Example 51 | 6-(4-fluorophenyl)-N-[(6-methylpyridazin-3-yl)methyl]-8-[[1-(trifluoromethyl)cyclopropyl]methoxy]quinazolin-4-amine 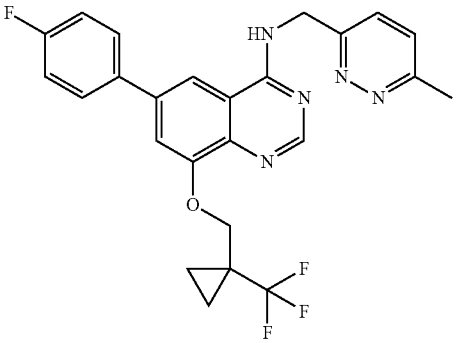 | $^1$H NMR (400 MHz, DMSO): δ 9.05 (dd, J = 5.8, 5.8 Hz, 1 H), 8.46 (s, 1 H), 8.23 (d, J = 1.5 Hz, 1 H), 7.97-7.92 (m, 2 H), 7.60 (d, J = 1.5 Hz, 1 H), 7.56 (d, J = 8.7 Hz, 1 H), 7.50 (d, J = 8.7 Hz, 1 H), 7.38 (dd, J = 8.9, 8.9 Hz, 2 H), 5.03 (d, J = 5.8 Hz, 2 H), 4.44 (s, 2 H), 2.60 (s, 3 H), 1.19-1.08 (m, 4 H). LCMS (Method 3): [MH$^+$] = 484 at 4.94 min. | Intermediate 11, (1-(trifluoro-methyl)cyclo-propyl)methyl methanesul-fonate, $Cs_2CO_3$ |
| Example 52 | tert-butyl 3-[6-(4-fluorophenyl)-4-[(6-methylpyridazin-3-yl)methylamino]quinazolin-8-yl]oxyacetidine-1-carboxylate 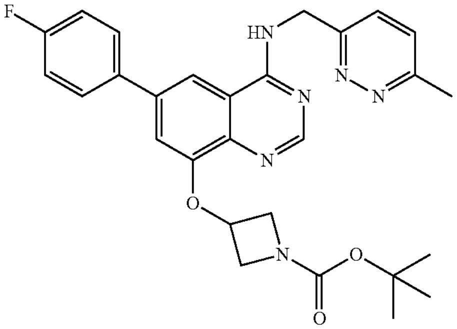 | $^1$H NMR (400 MHz, DMSO): δ 9.10 (dd, J = 5.8, 5.8 Hz, 1 H), 8.45 (s, 1 H), 8.25 (d, J = 1.5 Hz, 1 H), 7.94-7.89 (m, 2 H), 7.56 (d, J = 8.7 Hz, 1 H), 7.50 (d, J = 8.8 Hz, 1 H), 7.38 (dd, J = 8.9, 8.9 Hz, 2 H), 7.30 (d, J = 1.4 Hz, 1 H), 5.38-5.31 (m, 1 H), 5.03 (d, J = 5.6 Hz, 2 H), 4.42 (dd, J = 7.2, 7.2 Hz, 2 H), 3.95 (dd, J = 2.6, 8.9 Hz, 2 H), 2.60 (s, 3 H), 1.42 (s, 9 H). LCMS (Method 3): [MH$^+$] = 517 at 4.75 min. | Intermediate 11, tert-butyl 3-iodoazetidine-1-carboxylate, $Cs_2CO_3$ |
| Example 53 | 2-[6-(4-fluorophenyl)-4-[(6-methylpyridazin-3-yl)-methylamino]quinazolin-8-yl]oxyacetonitrile 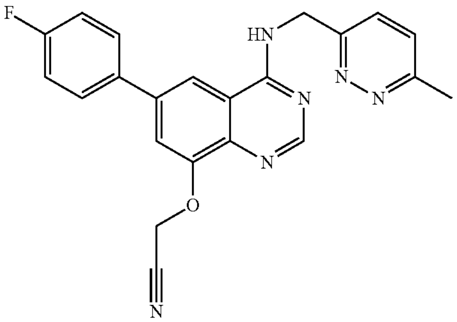 | $^1$H NMR (400 MHz, DMSO): δ 9.18 (dd, J = 5.9, 5.9 Hz, 1 H), 8.46 (s, 1 H), 8.37 (d, J = 1.6 Hz, 1 H), 7.97-7.92 (m, 2 H), 7.79 (d, J = 1.6 Hz, 1 H), 7.58 (d, J = 8.5 Hz, 1 H), 7.50 (d, J = 8.7 Hz, 1 H), 7.42 (dd, J = 8.8, 8.8 Hz, 2 H), 5.50 (s, 2 H), 5.05 (d, J = 5.8 Hz, 2 H), 2.60 (s, 3 H). LCMS (Method 3): [MH$^+$] = 401 at 4.07 min. | Intermediate 11, 2-bromoaceto-nitrile, $Cs_2CO_3$ |

-continued

| Example No. | Structure | Analytical data ¹H NMR LC-MS | Reagents |
|---|---|---|---|
| Example 54 | 2-[6-(4-fluorophenyl)-4-[(6-methylpyridazin-3-yl)methylamino]quinazolin-8-yl]oxy-N-methoxy-N-methyl-acetamide 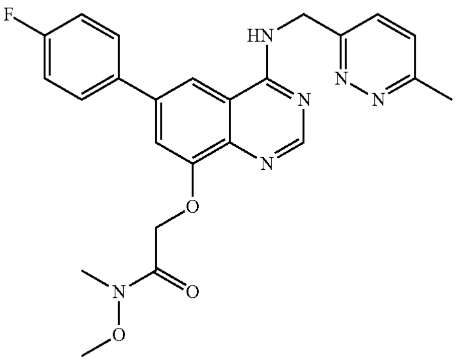 | $^1$H NMR (400 MHz, DMSO): δ 9.07 (dd, J = 6.0, 6.0 Hz, 1 H), 8.44 (s, 1 H), 8.21 (d, J = 1.6 Hz, 1 H), 7.88 (ddd, J = 3.3, 5.4, 12.2 Hz, 2 H), 7.56 (d, J = 8.5 Hz, 1 H), 7.51-7.47 (m, 2 H), 7.39 (dd, J = 8.9, 8.9 Hz, 2 H), 5.24 (s, 2 H), 5.04 (d, J = 5.8 Hz, 2 H), 3.80 (s, 3 H), 3.16 (s, 3 H), 2.60 (s, 3 H). LCMS (Method 3): [MH$^+$] = 463.5 at 4.08 min. | Intermediate 11,, 2-bromo-N-methoxy-N-methylacetamide, $Cs_2CO_3$ |
| Example 55 | 2-[2-[6-(4-fluorophenyl)-4-[(6-methylpyridazin-3-yl)-methylamino]quinazolin-8-yl]oxyethoxy]ethanol 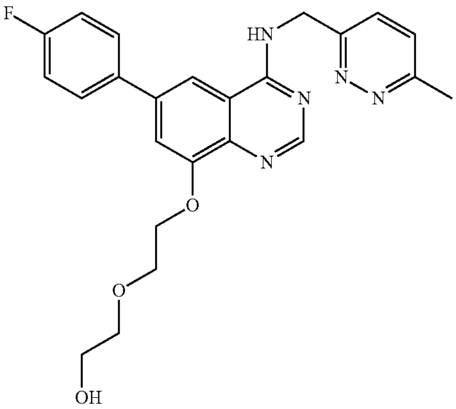 | $^1$H NMR (400 MHz, DMSO): δ 9.04 (dd, J = 5.9, 5.9 Hz, 1 H), 8.43 (s, 1 H), 8.19 (d, J = 1.6 Hz, 1 H), 7.96-7.92 (m, 2 H), 7.59-7.55 (m, 2 H), 7.50 (d, J = 8.7 Hz, 1 H), 7.38 (dd, J = 8.9, 8.9 Hz, 2 H), 5.03 (d, J = 5.8 Hz, 2 H), 4.74-4.70 (m, 1 H), 4.39 (dd, J = 4.6, 4.6 Hz, 2 H), 3.89 (dd, J = 4.6, 4.6 Hz, 2 H), 3.57 (s, 4 H), 2.60 (s, 3 H). LCMS (Method 4): [MH$^+$] = 450 at 2.86 min. | Intermediate 11, 2-(2-bromoethoxy)ethan-1-ol, $Cs_2CO_3$ |
| Example 56 | 3-[6-(4-fluorophenyl)-4-[(6-methylpyridazin-3-yl)-methylamino]quinazolin-8-yl]oxy-1-methyl-pyrrolidin-2-one 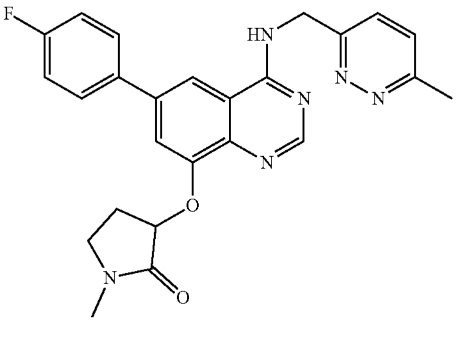 | $^1$H NMR (400 MHz, DMSO): δ 9.07 (dd, J = 5.9, 5.9 Hz, 1 H), 8.42 (s, 1 H), 8.24 (d, J = 1.5 Hz, 1 H), 7.93-7.88 (m, 2 H), 7.82 (d, J = 1.5 Hz, 1 H), 7.56 (d, J = 8.7 Hz, 1 H), 7.50 (d, J = 8.7 Hz, 1 H), 7.40 (dd, J = 8.9, 8.9 Hz, 2 H), 5.44 (dd, J = 7.3, 7.3 Hz, 1 H), 5.04 (d, J = 5.8 Hz, 2 H), 3.52-3.37 (m, 2 H), 2.84 (s, 3 H), 2.61-2.60 (m, 3 H), 2.15-2.06 (m, 2 H). LCMS (Method 4): [MH$^+$] = 459 at 2.93 min. | Intermediate 11,, 3-bromo-1-methylpyrrolidin-2-one, $Cs_2CO_3$ |

-continued

| Example No. | Structure | Analytical data $^1$H NMR LC-MS | Reagents |
|---|---|---|---|
| Example 57 | 6-(4-fluorophenyl)-N-[(6-methylpyridazin-3-yl)methyl]-8-(oxazol-2-ylmethoxy)quinazolin-4-amine 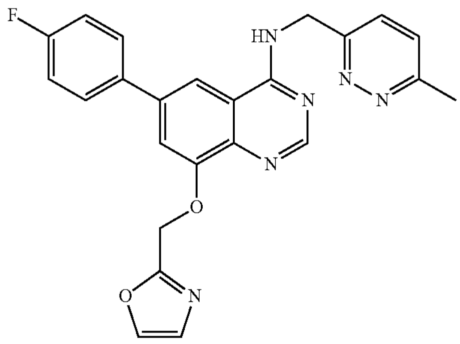 | $^1$H NMR (400 MHz, DMSO): δ 9.09 (dd, J = 5.8, 5.8 Hz, 1 H), 8.42 (s, 1 H), 8.26 (d, J = 1.6 Hz, 1 H), 8.23 (s, 1 H), 7.95-7.91 (m, 2 H), 7.76 (d, J = 1.5 Hz, 1 H), 7.56 (d, J = 8.7 Hz, 1 H), 7.50 (d, J = 8.7 Hz, 1 H), 7.40 (dd, J = 8.9, 8.9 Hz, 2 H), 7.32 (s, 1 H), 5.55 (s, 2 H), 5.03 (d, J = 5.8 Hz, 2 H), 2.60 (s, 3 H). LCMS (Method 3): [MH$^+$] = 443 at 4.12 min. | Intermediate 11, 2-(chloromethyl)-oxazole, $Cs_2CO_3$ |
| Example 58 | 6-(4-fluorophenyl)-8-[(5-methyl-1,2,4-oxadiazol-3-yl)methoxy]-N-[(6-methylpyridazin-3-yl)methyl]-quinazolin-4-amine 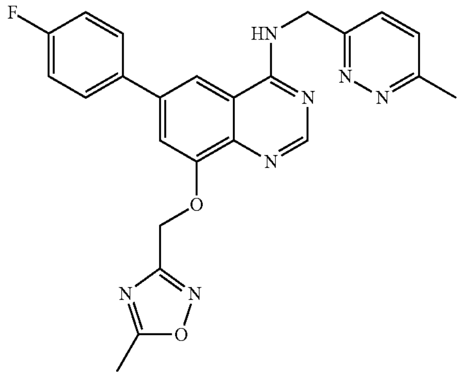 | $^1$H NMR (400 MHz, DMSO): δ 9.09 (dd, J = 5.9, 5.9 Hz, 1 H), 8.43 (s, 1 H), 8.26 (d, J = 1.6 Hz, 1 H), 7.96-7.92 (m, 2 H), 7.76 (d, J = 1.5 Hz, 1 H), 7.57 (d, J = 8.5 Hz, 1 H), 7.50 (d, J = 8.8 Hz, 1 H), 7.40 (dd, J = 8.8, 8.8 Hz, 2 H), 5.55 (s, 2 H), 5.04 (d, J = 5.8 Hz, 2 H), 2.65 (s, 3 H), 2.60 (s, 3 H). LCMS (Method 4): [MH$^+$] = 458 at 3.15 min. | Intermediate 11, 3-(chloromethyl)-5-methyl-1,2,4-oxadiazole, $Cs_2CO_3$ |
| Example 59 | 8-[(3-ethyl-1,2,4-oxadiazol-5-yl)methoxy]-6-(4-fluorophenyl)-N-[(6-methylpyridazin-3-yl)methyl]quinazolin-4-amine 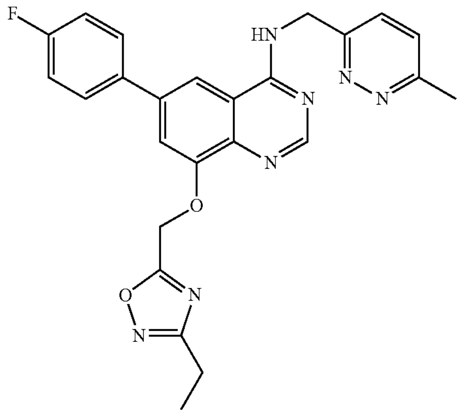 | $^1$H NMR (400 MHz, DMSO): δ 9.13 (dd, J = 5.8, 5.8 Hz, 1 H), 8.45 (s, 1 H), 8.30 (d, J = 1.6 Hz, 1 H), 7.95-7.90 (m, 2 H), 7.75 (d, J = 1.5 Hz, 1 H), 7.57 (d, J = 8.5 Hz, 1 H), 7.50 (d, J = 8.7 Hz, 1 H), 7.40 (dd, J = 8.9, 8.9 Hz, 2 H), 5.79 (s, 2 H), 5.04 (d, J = 5.8 Hz, 2 H), 2.78 (q, J = 7.5 Hz, 2 H), 2.60 (s, 3 H), 1.25 (dd, J = 7.5, 7.5 Hz, 3 H). LCMS (Method 4): [MH$^+$] = 472 at 3.36 min. | Intermediate 11, 5-(chloromethyl)-3-ethyl-1,2,4-oxadiazole, $Cs_2CO_3$ |

-continued

| Example No. | Structure | Analytical data $^1H$ NMR LC-MS | Reagents |
|---|---|---|---|
| Example 60 | 8-[(5-cyclopropyl-1,3,4-thiadiazol-2-yl)methoxy]-6-(4-fluorophenyl)-N-[(6-methylpyridazin-3-yl)methyl]-quinazolin-4-amine 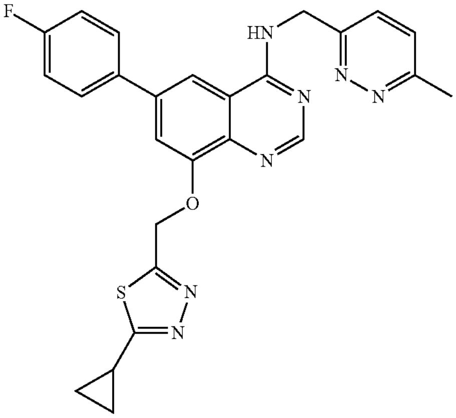 | $^1H$ NMR (400 MHz, DMSO): δ 9.11 (dd, J = 5.9, 5.9 Hz, 1 H), 8.45 (s, 1 H), 8.29 (d, J = 1.5 Hz, 1 H), 7.97-7.92 (m, 2 H), 7.80 (d, J = 1.5 Hz, 1 H), 7.57 (d, J = 8.7 Hz, 1 H), 7.50 (d, J = 8.7 Hz, 1 H), 7.40 (dd, J = 8.9, 8.9 Hz, 2 H), 5.82 (s, 2 H), 5.04 (d, J = 5.8 Hz, 2 H), 2.60 (s, 3 H), 2.59-2.54 (m, 1 H), 1.26-1.20 (m, 2 H), 1.08-1.03 (m, 2 H). LCMS (Method 4): [$MH^+$] = 500 at 3.23 min. | Intermediate 11, 2-(chloromethyl)-5-cyclopropyl-1,3,4-thiadiazole, $Cs_2CO_3$ |
| Example 61 | 2-[6-(4-fluorophenyl)-4-[(6-methylpyridazin-3-yl)-methylamino]quinazolin-8-yl]oxy-N-(2,2,2-trifluoro-ethyl)acetamide 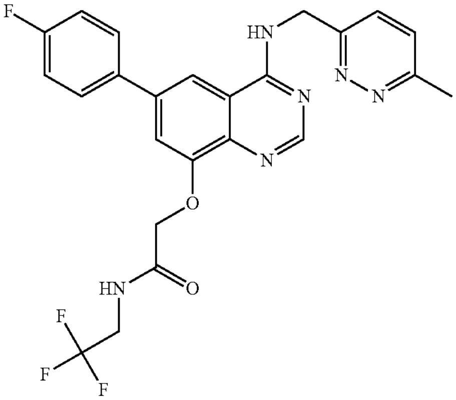 | $^1H$ NMR (400 MHz, DMSO): δ 9.28-9.15 (m, 2 H), 8.47 (s, 1 H), 8.32 (d, J = 1.6 Hz, 1 H), 7.93-7.88 (m, 2 H), 7.72 (d, J = 1.6 Hz, 1 H), 7.57 (d, J = 8.7 Hz, 1 H), 7.51 (d, J = 8.7 Hz, 1 H), 7.39 (dd, J = 8.9, 8.9 Hz, 2 H), 5.05 (d, J = 5.8 Hz, 2 H), 4.95 (s, 2 H), 4.09-3.98 (m, 2 H), 2.60 (s, 3 H). LCMS (Method 4): [$MH^+$] = 501 at 3.22 min. | Intermediate 11, 2-chloro-N-(2,2,2-trifluoro-ethyl)acetamide, $Cs_2CO_3$ |
| Example 62 | 8-((5-cyclopropyl-1,3,4-oxadiazol-2-yl)methoxy)-6-(4-fluorophenyl)-N-((6-methylpyridazin-3-yl)methyl)-quinazolin-4-amine 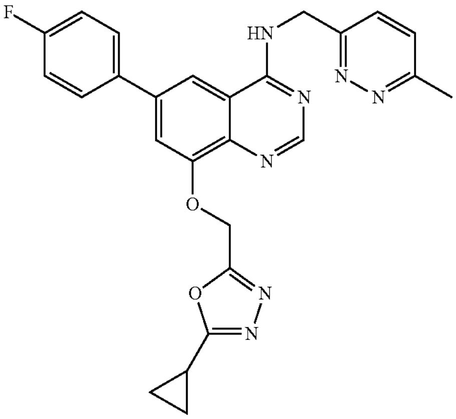 | $^1H$ NMR (400 MHz, DMSO): δ 9.12 (dd, J = 5.8, 5.8 Hz, 1 H), 8.43 (s, 1 H), 8.30 (d, J = 1.5 Hz, 1 H), 7.96-7.92 (m, 2 H), 7.79 (d, J = 1.6 Hz, 1 H), 7.57 (d, J = 8.7 Hz, 1 H), 7.50 (d, J = 8.7 Hz, 1 H), 7.41 (dd, J = 8.9, 8.9 Hz, 2 H), 5.64 (s, 2 H), 5.04 (d, J = 5.8 Hz, 2 H), 2.60 (s, 3 H), 2.35-2.26 (m, 1 H), 1.20-1.14 (m, 2 H), 1.04-0.99 (m, 2 H). LCMS (Method 4): [MH+] = 484 at 3.06 min. | Intermediate 11, 2-(chloromethyl)-5-cyclopropyl-1,3,4-oxadiazole, $Cs_2CO_3$ |

-continued

| Example No. | Structure | Analytical data $^1$H NMR LC-MS | Reagents |
|---|---|---|---|
| Example 63 | 6-(4-fluorophenyl)-N-((6-methylpyridazin-3-yl)methyl)-8-(oxetan-3-yloxy)quinazolin-4-amine 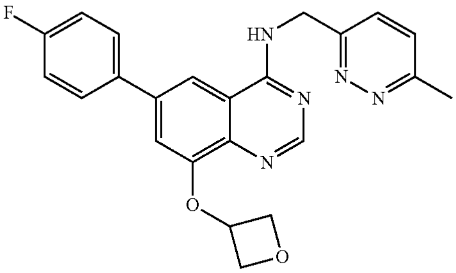 | $^1$H NMR (400 MHz, DMSO): δ 8.29 (s, 1 H), 8.17 (s, 1 H), 8.03 (d, J = 1.6 Hz, 1 H), 7.80-7.75 (m, 2 H), 7.68 (d, J = 8.5 Hz, 1 H), 7.55-7.51 (m, 2 H), 7.32 (dd, J = 8.9, 8.9 Hz, 2 H), 5.07 (s, 2 H), 4.43-4.37 (m, 2 H), 4.02-3.95 (m, 1 H), 3.83-3.72 (m, 2 H), 2.61 (s, 3 H). LCMS (Method 4): [MH+] = 418 at 2.69 min. | Intermediate 11, 3-iodooxetane, $Cs_2CO_3$ |
| Example 64 | Methyl 4-[[6-(4-fluorophenyl)-4-[(6-methylpyridazin-3-yl)methylamino]quinazolin-8-yl]oxymethyl]piperidine-1-carboxylate 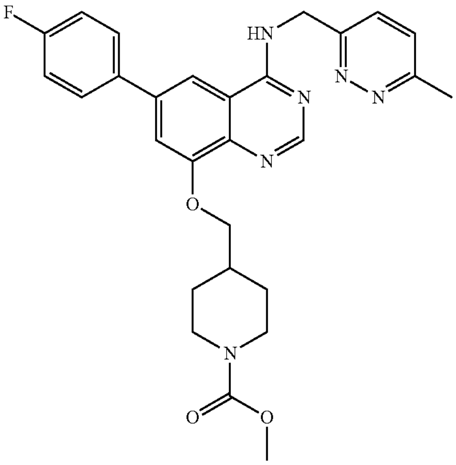 | $^1$H NMR (400 MHz, DMSO): δ 9.03 (dd, J = 5.8, 5.8 Hz, 1 H), 8.44 (s, 1 H), 8.17 (d, J = 1.4 Hz, 1 H), 7.95-7.90 (m, 2 H), 7.55 (d, J = 8.7 Hz, 2 H), 7.50 (d, J = 8.7 Hz, 1 H), 7.38 (dd, J = 8.9, 8.9 Hz, 2 H), 5.03 (d, J = 5.8 Hz, 2 H), 4.10 (dd, J = 6.5, 16.4 Hz, 2 H), 4.06-3.93 (m, 4 H), 3.59 (s, 3 H), 3.18 (s, 3 H), 2.13-2.06 (m, 1 H), 1.93-1.84 (m, 1 H), 1.70-1.66 (m, 1 H), 1.34-1.07 (m, 2 H). LCMS (Method 4): [$MH^+$] = 517.5 at 3.36 min. | Intermediate 11, Methyl 4-(((methylsulfonyl)oxy)-methyl)piperidine-1-carboxylate, $Cs_2CO_3$ |
| Example 65 | Methyl 4-[6-(4-fluorophenyl)-4-[(6-methylpyridazin-3-yl)-methylamino]qinazolin-8-yl]oxypiperidine-1-carboxylate 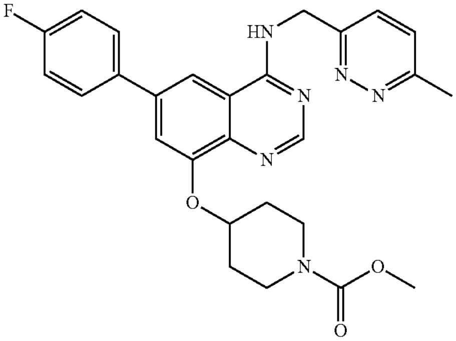 | $^1$H NMR (400 MHz, DMSO): δ 9.08 (s, 1 H), 8.45-8.44 (m, 1 H), 8.23 (d, J = 1.6 Hz, 1 H), 7.94-7.90 (m, 2 H), 7.69 (d, J = 1.5 Hz, 1 H), 7.58-7.49 (m, 2 H), 7.41-7.36 (m, 2 H), 5.04-4.99 (m, 3 H), 3.80-3.72 (m, 2 H), 3.62 (s, 3 H), 3.33-3.29 (m, 2H), 2.60 (s, 3 H), 2.01-1.92 (m, 2 H), 1.75-1.65 (m, 2 H). LCMS (Method 3): [$MH^+$] = 503 at 3.98 min. | Intermediate 11, Methyl 4-((methylsulfonyl)oxy)-piperidine-1-carboxylate, $Cs_2CO_3$ |

-continued

| Example No. | Structure | Analytical data $^1H$ NMR LC-MS | Reagents |
|---|---|---|---|
| Example 66 | Methyl 3-[[6-(4-fluorophenyl)-4-[(6-methylpyridazin-3-yl)methylamino]quinazolin-8-yl]oxymethyl]piperidine-1-carboxylate 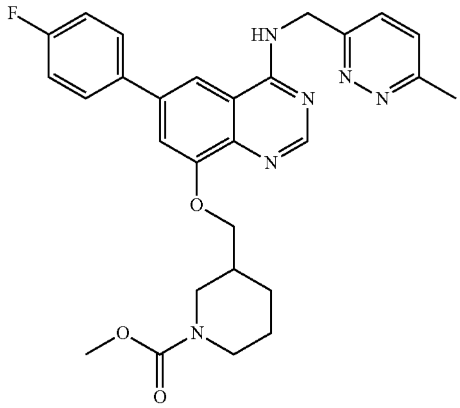 | $^1H$ NMR (400 MHz, DMSO): δ 9.04 (t, J = 5.9 Hz, 1 H), 8.46 (s, 1 H), 8.19 (d, J = 1.5 Hz, 1 H), 7.96-7.91 (m, 2 H), 7.57-7.49 (m, 3 H), 7.41-7.36 (m, 2 H), 5.03 (d, J = 5.8 Hz, 2 H), 4.18-4.11 (m, 3 H), 3.89 (d, J = 12.9 Hz, 1 H), 3.61-3.56 (m, 3 H), 2.92-2.87 (m, 2 H), 2.60 (s, 3 H), 2.10-2.01 (m, 1 H), 1.97-1.91 (m, 1 H), 1.74-1.69 (m, 1 H), 1.49-1.32 (m, 2 H). LCMS (Method 3): [$MH^+$] = 517 at 4.34 min. | Intermediate 11, Methyl 3-(((methylsulfonyl)oxy)methyl)piperidine-1-carboxylate, $Cs_2CO_3$ |
| Example 67 | Methyl 3-[[6-(4-fluorophenyl)-4-[(6-methylpyridazin-3-yl)methylamino]quinazolin-8-yl]oxymethyl]pyrrolidine-1-carboxylate 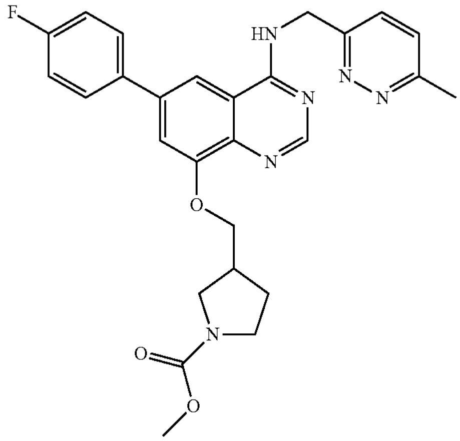 | $^1H$ NMR (400 MHz, DMSO): δ 9.04 (t, J = 5.9 Hz, 1 H), 8.45 (s, 1 H), 8.19 (d, J = 1.5 Hz, 1 H), 7.96-7.91 (m, 2 H), 7.60-7.49 (m, 3 H), 7.41-7.35 (m, 2 H), 5.03 (d, J = 5.8 Hz, 2 H), 4.30-4.16 (m, 2 H), 3.59 (s, 3 H), 3.57-3.53 (m, 1 H), 3.51-3.45 (m, 1 H), 3.32-3.26 (m, 1 H), 2.84-2.67 (m, 2 H), 2.61-2.60 (m, 3 H), 2.15-2.04 (m, 1 H), 1.91-1.81 (m, 1 H). LCMS (Method 3): [$MH^+$] = 503 at 3.95 min. | Intermediate 11, Methyl 3-(((methylsulfonyl)oxy)methyl)pyrrolidine-1-carboxylate, $Cs_2CO_3$ |
| Example 68 | Methyl 3-[6-(4-fluorophenyl)-4-[(6-methylpyridazin-3-yl)methylamino]quinazolin-8-yl]oxypyrrolidine-1-carboxylate 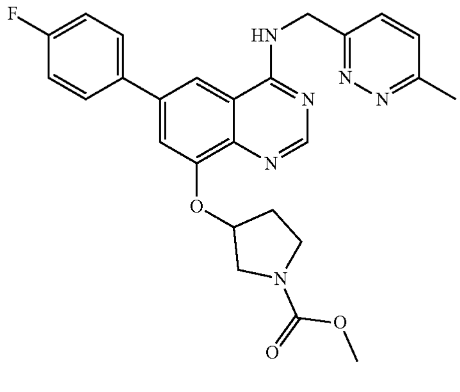 | $^1H$ NMR (400 MHz, DMSO): δ 9.08 (t, J = 5.9 Hz, 1 H), 8.43-8.43 (m, 1 H), 8.25 (d, J = 1.6 Hz, 1 H), 7.95-7.91 (m, 2 H), 7.63-7.48 (m, 3 H), 7.41-7.36 (m, 2 H), 5.05-5.01 (m, 2 H), 3.64-3.59 (m, 6 H), 3.52-3.44 (m, 5 H), 2.21-2.19 (m, 2 H). LCMS (Method 3): [MH+] = 489 at 3.78 min. | Intermediate 11, Methyl 3-((methylsulfonyl)oxy)pyrrolidine-1-carboxylate, $Cs_2CO_3$ |

-continued

| Example No. | Structure | Analytical data $^1H$ NMR LC-MS | Reagents |
|---|---|---|---|
| Example 69 | Methyl 3-[6-(4-fluorophenyl)-4-[(6-methylpyridazin-3-yl)-methylamino]quinazolin-8-yl]-oxypiperidine-1-carboxylate 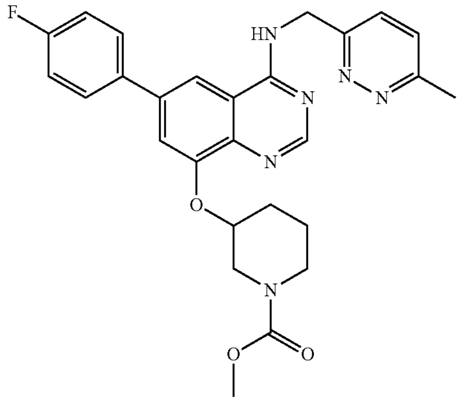 | $^1H$ NMR (400 MHz, DMSO): δ 9.08 (t, J = 5.5 Hz, 1 H), 8.43 (s, 1 H), 8.25 (s, 1 H), 7.93 (dd, J = 5.5, 8.6 Hz, 2 H), 7.68 (s, 1 H), 7.58-7.48 (m, 2 H), 7.42-7.36 (m, 2 H), 5.05-5.01 (m, 2 H), 4.80 (s, 1 H), 3.85-3.79 (m, 1 H), 3.63-3.44 (m, 5 H), 2.60 (s, 3 H), 2.06-2.02 (m, 1 H), 1.90-1.81 (m, 2 H), 1.59-1.48 (m, 1 H). LCMS (Method 4): $[MH^+]$ = 503 at 3.23 min. | Intermediate 11, Methyl 3-((methylsulfonyl)oxy)-piperidine-1-carboxylate, $Cs_2CO_3$ |

Pharmacological Activity of the Compounds of the Invention.

In Vitro Electrophysiology Assay for $P2X_3$

Cells expressing $P2X_3$ receptors were grown according to standard practice and maintained at 37° C. in a 5% humidified $CO_2$ atmosphere. The cells were seeded into T175 flask 2 days prior to the day of the assay and dissociated from the flasks using TrypLE when grown to confluence of 80-90%. The dissociated cells were resuspended in serum free media at a cell density of $3\times10^6$ cells/ml and loaded onto the Sophion Qube automated patch-clamp system. The extracellular assay buffer contained 145 mM NaCl, 4 mM KCl, 2 mM $CaCl_2$, 1 mM $MgCl_2$, 10 mM HEPES, and 10 mM glucose at pH 7.4. The intracellular assay solution contained 140 mM CsF, 10 mM NaCl, 10 mM EGTA, 10 mM HEPES at pH 7.2. Agonist stock solutions were prepared in H2O and diluted in bath solution prior to use. All antagonists were prepared as 10 mM stock solutions in DMSO and diluted in bath solution prior to use. All experiments were performed under the whole-cell patch clamp configuration at room temperature with 384 individual cells being voltage clamped at −60 mV simultaneously on the Sophion Qube instrument. Two baseline responses were established with the application of α,β-MeATP (800 nM), with the subsequent agonist applications being washed out using extracellular assay buffer containing 0.5 U/ml apyrase. Following the second agonist application, antagonist was incubated in the absence of α,β-MeATP for 10 minutes. After antagonist preincubation, 800 nM α,β-MeATP and antagonist were co-administered to determine the inhibitory effect of the antagonist. One concentration of an antagonist was assessed against a single cell, with different concentrations of the antagonist applied to other cells on the 384 recording substrate. The control $P2X_3$ current amplitude was taken from the peak current amplitude from the second agonist response prior to preincubation with antagonist. The peak $P2X_3$ current amplitude in the presence of antagonist was used to calculate the inhibitory effect at each concentration of the antagonist according to the following equation:

$$\text{Percentage inhibition of } P2X_3 = (P2X_3 \text{ control peak amplitude} - P2X_3 \text{ antagonist peak amplitude}) / P2X_3 \text{ control peak amplitude}) * 100$$

Concentration-response curves were constructed from ten different concentrations with each concentration of antagonist tested on at least two individual cells. The concentration of the antagonist to inhibit $P2X_3$ current by 50% ($IC_{50}$) was determined by fitting the data with the following equation:

$$Y = a + [(b - a)/(1 + 10\char`^((\log c - x)d)]$$

Where 'a' is minimum response, 'b' is maximum response, 'c' is $IC_{50}$ and 'd' is Hill slope.

The results for individual compounds are provided below in Table 2 and are expressed as range of activity.

TABLE 2

| Example No. | h $P2X_3$ |
|---|---|
| 1 | +++ |
| 2 | +++ |
| 4 | ++ |
| 5 | ++ |
| 6 | +++ |
| 7 | + |
| 8 | +++ |
| 9 | +++ |
| 10 | ++ |
| 11 | +++ |
| 12 | +++ |
| 13 | +++ |
| 14 | +++ |
| 15 | +++ |
| 16 | +++ |
| 17 | +++ |
| 18 | ++ |
| 19 | ++ |
| 20 | +++ |
| 21 | +++ |
| 22 | +++ |
| 23 | ++ |
| 24 | ++ |
| 25 | ++ |
| 26 | ++ |
| 27 | +++ |
| 28 | + |
| 29 | + |
| 30 | ++ |
| 31 | ++ |
| 32 | ++ |
| 33 | ++ |
| 34 | +++ |

TABLE 2-continued

| Example No. | h $P2X_3$ |
|---|---|
| 35 | ++ |
| 36 | ++ |
| 37 | +++ |
| 38 | +++ |
| 39 | +++ |
| 40 | +++ |
| 41 | ++ |
| 42 | ++ |
| 43 | ++ |
| 44 | ++ |
| 45 | +++ |
| 46 | ++ |
| 47 | ++ |
| 48 | ++ |
| 49 | +++ |
| 50 | +++ |
| 51 | ++ |
| 52 | ++ |
| 53 | +++ |
| 54 | +++ |
| 55 | +++ |
| 56 | ++ |
| 57 | +++ |
| 58 | +++ |
| 59 | +++ |
| 60 | +++ |
| 61 | ++ |
| 62 | +++ |
| 63 | ++ |
| 64 | ++ |
| 65 | ++ |
| 66 | ++ |
| 67 | ++ |
| 68 | ++ |

wherein the compounds are classified in term of potency with respect to their inhibitory activity on $P2X_3$ according to the following classification criterion:

+++: $pIC_{50}$ h $P2X_3$>6.5

++: 6.5<$pIC_{50}$ h $P2X_3$>5.5

+: 5.5<$pIC_{50}$ h $P2X_3$>4.5

In vitro Electrophysiology Assay for $P2X_{2/3}$

Representative compound of the present invention have been also tested for $P2X_{2/3}$ receptor.

The same assay protocol was used for the $P2X_{2/3}$ assay as the $P2X_3$ assay with two modifications: 1) 10 μM ATP was used as the agonist; and 2) the mean current amplitude was measured seven seconds after the application of agonist.

The results of Table 3 indicate that representative compounds of the present invention are selective $P2X_3$ antagonist.

TABLE 3

| Example No. | h $P2X_3$ | h $P2X_{2/3}$ |
|---|---|---|
| 1 | +++ | + |
| 2 | +++ | ++ |
| 6 | +++ | + |
| 9 | +++ | ++ |
| 15 | +++ | ++ |
| 16 | +++ | ++ |
| 17 | +++ | ++ |
| 21 | +++ | + |
| 22 | +++ | + |
| 27 | +++ | ++ |
| 34 | +++ | ++ |
| 42 | ++ | + |
| 43 | ++ | + |
| 47 | ++ | + |
| 62 | +++ | ++ |
| 65 | ++ | + |
| 68 | ++ | + |

wherein the compounds are classified in term of potency with respect to their inhibitory activity on $P2X_3$ or $P2X_2$/3 isoforms according to the following classification criterion:

+++: $pIC_{50}$ h $P2X_3$ or h $P2X_{2/3}$>6.5

++: 6.5<$pIC_{50}$ h $P2X_3$ or h $P2X_{2/3}$>5.5

+: 5.5<$pIC_{50}$ h $P2X_3$ or h $P2X_{2/3}$>4.5

Comparative Example A

N-(6-(4-fluorophenyl)chroman-4-yl)-2-(trifluoromethyl)pyrimidine-5-carboxamide

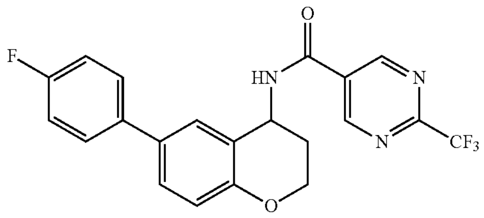 [SMILES: O=C(NC1CCOc2ccc(-c3ccc(F)cc3)cc21)c1cnc(C(F)(F)F)nc1]

The activity of comparative Example A as has been tested in the in vitro assay for the determination of activity on $P2X_3$ receptor as described above.

Differently from the compounds of formula (I) of the present invention, the comparative Example A do not show a proper inhibitory activity on $P2X_3$, in fact the activity on receptor $P2X_3$ expressed as $pIC_{50}$ is <4.5.

The above results demonstrate that the amino quinazoline scaffold in combination with a proper substituents, in particular in $R_2$ position, unexpectedly lead to a series of compounds that is active against the receptor $P2X_3$.

The invention claimed is:

1. A compound selected from the group consisting of:

8-(2,2-difluoroethoxy)-6-(4-fluorophenyl)-N-((6-methylpyridazin-3-yl)methyl)quinazolin-4-amine, (R)-8-(2,2-difluoroethoxy)-6-(4-fluorophenyl)-N-(1-(2-(trifluoromethyl)pyrimidin-5-yl)ethyl)quinazolin-4-amine, 8-(2,2-difluoroethoxy)-6-(5-fluoropyridin-2-yl)-N-((6-methylpyridazin-3-yl)methyl)quinazolin-4-amine, (R)-8-(2,2-difluoroethoxy)-6-(5-fluoropyridin-2-yl)-N-(1-(6-methylpyridazin-3-yl)ethyl)quinazolin-4-amine, Single enantiomer 1 of 8-(2,2-difluoroethoxy)-6-(5-fluoro-2-pyridyl)-N-[1-(5-methyl-1,3,4-thiadiazol-2-yl)ethyl]quinazolin-4-amine, Single enantiomer 2 of 8-(2,2-difluoroethoxy)-6-(5-fluoro-2-pyridyl)-N-[1-(5-methyl-1,3,4-thiadiazol-2-yl)ethyl]quinazolin-4-amine, 8-(2,2-Difluoroethoxy)-N-((6-methylpyridazin-3-yl) methyl)-6-(5-methylpyridin-2-yl) quinazolin-4-amine, 8-(2,2-difluoroethoxy)-N-[(6-methylpyridazin-3-yl) methyl]-6-(5-methylpyrimidin-2-yl)quinazolin-4-amine, (R)-8-((3,3-difluoropyrrolidin-1-yl)sulfonyl)-6-(4-fluorophenyl)-N-(1-(6-methylpyridazin-3-yl)ethyl)quinazolin-4-amine, (R)-8-((3,3-difluoropyrrolidin-1-yl)sulfonyl)-6-(4-fluorophenyl)-N-(1-(5-methyl-1,2,4-oxadiazol-3-yl)ethyl) quinazolin-4-amine, 8-((3,3-difluoropyrrolidin-1-yl)sulfonyl)-6-(4-fluorophenyl)-N-(1-(5-methyl-1,3,4-thiadiazol-2-yl)ethyl)quinazolin-4-amine, (R)-1-((6-(4-fluorophenyl)-4-((1-(6-methylpyridazin-3-yl)ethyl)amino)quinazolin-8-yl)sulfonyl)piperidin-4-ol, (R)-1-((6-(4-fluorophenyl)-4-((1-(5-methyl-1,2,4-oxadiazol-3-yl)ethyl)amino)quinazolin-8-yl)sulfonyl)piperidin-4-ol, (R)-6-(4-fluorophenyl)-N-(1-(6-methylpyridazin-3-yl)ethyl)-8-(methylthio) quinazolin-4-amine, 6-(4-fluorophenyl)-N—((R)-1-(6-methylpyridazin-3-yl)ethyl)-8-(methylsulfinyl) quinazolin-4-amine, (R)-6-(4-fluorophenyl)-N-(1-(6-methylpyridazin-3-yl)ethyl)-8-(oxetan-3-ylthio)quinazolin-4-amine, 6-(4-fluorophenyl)-N—((R)-1-(6-methylpyridazin-3-yl)ethyl)-8-(oxetan-3-ylsulfinyl)quinazolin-4-amine, N-((1S,4s)-4-((6-(4-fluorophenyl)-4-(((R)-1-(2-(trifluoromethyl)pyrimidin-5-yl)ethyl)amino)quinazolin-8-yl)oxy)cyclohexyl)acetamide, 6-(4-fluorophenyl)-8-((1-(2,2,2-trifluoroethyl)pyrrolidin-3-yl)oxy)-N—((R)-1-(2-(trifluoromethyl)pyrimidin-5-yl)ethyl)quinazolin-4-amine, 3-((6-(4-fluorophenyl)-4-(((R)-1-(2-(trifluoromethyl)pyrimidin-5-yl)ethyl)amino)quinazolin-8-yl)oxy)pyrrolidin-2-one, (R)-6-(4-fluorophenyl)-8-((1-(2,2,2-trifluoroethyl) piperidin-4-yl)oxy)-N-(1-(2-(trifluoromethyl)pyrimidin-5-yl)ethyl)quinazolin-4-amine, (R)-3-(((6-(4-fluorophenyl)-4-((1-(2-(trifluoromethyl)pyrimidin-5-yl)ethyl)amino)quinazolin-8-yl)oxy)methyl)oxetan-3-ol, (R)-5-(((6-(4-fluorophenyl)-4-((1-(2-(trifluoromethyl)pyrimidin-5-yl)ethyl)amino)quinazolin-8-yl)oxy)methyl)isoxazol-3-ol, (R)-2-((6-(4-fluorophenyl)-4-((1-(2-(trifluoromethyl)pyrimidin-5-yl)ethyl)amino)quinazolin-8-yl)oxy)-N-(phenylsulfonyl)acetamide, (R)-1-(((6-(4-fluorophenyl)-4-((1-(2-(trifluoromethyl)pyrimidin-5-yl)ethyl)amino)quinazolin-8-yl)oxy)methyl)cyclopropane-1-carboxylic acid, Methyl 1-(2-((6-(4-fluorophenyl)-4-(((6-methylpyridazin-3-yl)methyl)amino)quinazolin-8-yl)oxy)acetamido)cyclopropane-1-carboxylate, Methyl (R)-1-(2-((6-(4-fluorophenyl)-4-((1-(2-(trifluoromethyl)pyrimidin-5-yl)ethyl)amino)quinazolin-8-yl)oxy)acetamido)cyclopropane-1-carboxylate, (R)-1-(2-((6-(4-fluorophenyl)-4-((1-(2-(trifluoromethyl)pyrimidin-5-yl)ethyl)amino)quinazolin-8-yl)oxy)acetamido)cyclopropane-1-carboxylic acid, (1R,2S)-2-(2-((6-(4-fluorophenyl)-4-(((6-methylpyridazin-3yl)methyl)amino)quinazolin-8-yl)oxy)acetamido)cyclopentane-1-carboxylic acid, Ethyl (1S,2R)-2-(2-((6-(4-fluorophenyl)-4-(((6-methylpyridazin-3-yl)methyl)amino)quinazolin-8-yl)oxy)acetamido)cyclopentane-1-carboxylate, (R)-4-(((6-(4-fluorophenyl)-4-((1-(2-(trifluoromethyl)pyrimidin-5-yl)ethyl)amino)quinazolin-8-yl)oxy)methyl)piperidine-4-carboxylic acid hydrochloride, (R)-1-(((6-(4-fluorophenyl)-4-((1-(2-(trifluoromethyl)pyrimidin-5-yl)ethyl)amino)quinazolin-8-yl)oxy)methyl)cyclohexane-1-carboxylic acid, Ammonium (2-((4-(((6-methylpyridazin-3-yl)methyl)amino)-6-(5-methylpyrimidin-2-yl)quinazolin-8-yl)oxy)acetyl)(phenylsulfonyl)amide, 6-(4-fluorophenyl)-N-[(6-methylpyridazin-3-yl)methyl]-8-[[1-(trifluoromethyl)cyclopropyl]methoxy]quinazolin-4-amine, tert-butyl 3-[6-(4-fluorophenyl)-4-[(6-methylpyridazin-3-yl)methylamino]quinazolin-8-yl]oxyazetidine-1-carboxylate, 2-[6-(4-fluorophenyl)-4-[(6-methylpyridazin-3-yl)methylamino]quinazolin-8-yl]oxyacetonitrile, 2-[6-(4-fluorophenyl)-4-[(6-methylpyridazin-3-yl)methylamino]quinazolin-8-yl]oxy-N-methoxy-N-methylacetamide, 2-[2-[6-(4-fluorophenyl)-4-[(6-methylpyridazin-3-yl)methylamino]quinazolin-8-yl]oxyethoxy]ethanol, 3-[6-(4-fluorophenyl)-4-[(6-methylpyridazin-3-yl)methylamino]quinazolin-8-yl]oxy-1-methyl-pyrrolidin-2-one, 6-(4-fluorophenyl)-N-[(6-methylpyridazin-3-yl)methyl]-8-(oxazol-2-ylmethoxy)quinazolin-4-amine, 6-(4-fluorophenyl)-8-[(5-methyl-1,2,4-oxadiazol-3-yl)methoxy]-N-[(6-methylpyridazin-3-yl)methyl]quinazolin-4-amine, 8-[(3-ethyl-1,2,4-oxadiazol-5-yl)methoxy]-6-(4-fluorophenyl)-N-[(6-methylpyridazin-3-yl)methyl]quinazolin-4-amine, 8-[(5-cyclopropyl-1,3,4-thiadiazol-2-yl)methoxy]-6-(4-fluorophenyl)-N-[(6-methylpyridazin-3-yl)methyl]quinazolin-4-amine, 2-[6-(4-fluorophenyl)-4-[(6-methylpyridazin-3-yl)methylamino]quinazolin-8-yl]oxy-N-(2,2,2-trifluoroethyl)acetamide, 8-((5-cyclopropyl-1,3,4-oxadiazol-2-yl)methoxy)-6-(4-fluorophenyl)-N-((6-methylpyridazin-3-yl)methyl)quinazolin-4-amine, Methyl 4-[[6-(4-fluorophenyl)-4-[(6-methylpyridazin-3-yl)methylamino]quinazolin-8-yl]oxymethyl]piperidine-1-carboxylate, Methyl 4-[6-(4-fluorophenyl)-4-[(6-methylpyridazin-3-yl)methylamino]quinazolin-8-yl]oxypiperidine-1-carboxylate, Methyl 3-[[6-(4-fluorophenyl)-4-[(6-methylpyridazin-3-yl)methylamino]quinazolin-8-yl]oxymethyl]piperidine-1-carboxylate, Methyl 3-[[6-(4-fluorophenyl)-4-[(6-methylpyridazin-3-yl)methylamino]quinazolin-8-yl]oxymethyl]pyrrolidine-1-carboxylate, and Methyl 3-[6-(4-fluorophenyl)-4-[(6-methylpyridazin-3-yl)methylamino]quinazolin-8-yl]oxypyrrolidine-1-carboxylate.

2. A pharmaceutical composition comprising the compound of claim 1, either alone or in combination with another one or more active ingredients, in admixture with one or more pharmaceutically acceptable carriers or excipients.

3. The pharmaceutical composition according to claim 2, formulated for oral administration.

4. A method of treating a disease involving one or more P2X3 receptors, comprising administering to a subject in need thereof the pharmaceutical composition of claim 2.

5. A method of treating one or more respiratory diseases selected from the group consisting of cough, sub-acute or chronic cough, treatment-resistant cough, idiopathic chronic cough, post-viral cough, iatrogenic cough, asthma, idiopathic pulmonary fibrosis (IPF), chronic obstructive pulmonary disease (COPD) and cough associated with respiratory diseases, the method comprising administering to a subject in need thereof the pharmaceutical composition of claim 2.

6. A method of treating chronic cough, comprising administering to a subject in need thereof the pharmaceutical composition of claim 2.

7. The method according to claim 4, wherein the pharmaceutical composition is orally administered.

8. The method according to claim 5, wherein the pharmaceutical composition is orally administered.

9. The method according to claim 6, wherein the pharmaceutical composition is orally administered.

* * * * *